(12) United States Patent
Thompson et al.

(10) Patent No.: US 11,766,495 B2
(45) Date of Patent: *Sep. 26, 2023

(54) METHOD OF STERILIZING MEDICAL DEVICES, ANALYZING BIOLOGICAL INDICATORS, AND LINKING MEDICAL DEVICE STERILIZATION EQUIPMENT

(71) Applicant: ASP Global Manufacturing GmbH, Schaffhausen (CH)

(72) Inventors: Brian J. Thompson, Aliso Viejo, CA (US); Jacob S. Childs, Huntington Beach, CA (US); Chunhui Xie, Hebei (CN); Marco A. Mangiaterra, La Habra, CA (US); Darius D. Eghbal, Sierra Madre, CA (US); Margaret D. Shaffer, San Clemente, CA (US); Jeremy M. Yarwood, Aliso Viejo, CA (US); Benjamin M. Fryer, Lake Forest, CA (US); Howell B. Schwartz, Irvine, CA (US); Philippe Kanh Dang, San Diego, CA (US); Yaeer Lev, Redondo Beach, CA (US); Venkata Danam, Irvine, CA (US)

(73) Assignee: ASP Global Manufacturing GMBH

( * ) Notice: Subject to any disclaimer, the term of this patent is extended or adjusted under 35 U.S.C. 154(b) by 601 days.

This patent is subject to a terminal disclaimer.

(21) Appl. No.: 16/786,276

(22) Filed: Feb. 10, 2020

(65) Prior Publication Data

US 2020/0179549 A1 Jun. 11, 2020

Related U.S. Application Data

(63) Continuation of application No. 15/441,786, filed on Feb. 24, 2017, now Pat. No. 10,561,753.

(Continued)

(51) Int. Cl.
*A61L 2/28* (2006.01)
*A61L 2/24* (2006.01)
(Continued)

(52) U.S. Cl.
CPC ............... *A61L 2/28* (2013.01); *A61L 2/04* (2013.01); *A61L 2/14* (2013.01); *A61L 2/16* (2013.01);
(Continued)

(58) Field of Classification Search
CPC ........... A61L 2/28; A61L 2202/14; A61L 2/24
See application file for complete search history.

(56) References Cited

U.S. PATENT DOCUMENTS 5,863,790 A 1/1999 Bolea
5,955,296 A 9/1999 Roll
(Continued)

FOREIGN PATENT DOCUMENTS

CN 1492769 A 4/2004
CN 1663618 A 9/2005
(Continued)

OTHER PUBLICATIONS

Chinese Office Action dated Dec. 25, 2020, for Application No. 201710120893.7, 17 pages.
(Continued)

*Primary Examiner* — Kevin Joyner
(74) *Attorney, Agent, or Firm* — Lerner David LLP

(57) ABSTRACT

A biological indicator analyzer includes a plurality of wells, a plurality of organism detector features, and a user input feature such as a touch screen. Each well is configured to receive a respective biological indicator. Each organism detector feature is configured to detect whether a biological indicator disposed in a corresponding well of the plurality of wells contains a living organism. The touch screen is configured to receive user input and provide information to the (Continued)

user indicating a status of biological indicator analysis. The biological indicator analyzer may be used to analyze a biological indicator that was positioned in a sterilization chamber of a sterilizing cabinet along with at least one medical device that is to be sterilized. The analysis may indicate whether the sterilization cycle in the sterilization chamber as successful.

22 Claims, 45 Drawing Sheets

Related U.S. Application Data

(60) Provisional application No. 62/376,517, filed on Aug. 18, 2016, provisional application No. 62/316,722, filed on Apr. 1, 2016, provisional application No. 62/302,257, filed on Mar. 2, 2016.

(51) Int. Cl.
*A61L 2/16* (2006.01)
*A61L 2/04* (2006.01)
*A61L 2/14* (2006.01)
*A61L 2/20* (2006.01)

(52) U.S. Cl.
CPC .................. *A61L 2/20* (2013.01); *A61L 2/24* (2013.01); *A61L 2202/14* (2013.01); *A61L 2202/24* (2013.01)

(56) References Cited

U.S. PATENT DOCUMENTS

| | | | |
|---|---|---|---|
| 6,063,591 A | 5/2000 | Bolea | |
| 6,325,972 B1 | 12/2001 | Jacobs et al. | |
| 6,365,102 B1 | 4/2002 | Wu et al. | |
| 6,447,719 B1 | 9/2002 | Agamohamadi et al. | |
| 6,485,978 B1 | 11/2002 | Kirckof et al. | |
| 6,852,277 B2 | 2/2005 | Platt, Jr. et al. | |
| 6,852,279 B2 | 2/2005 | Williams et al. | |
| 6,936,434 B2 | 8/2005 | McDonnell et al. | |
| 6,939,519 B2 | 9/2005 | Agamohamadi et al. | |
| 6,986,736 B2 | 1/2006 | Williams et al. | |
| 7,138,087 B1 | 11/2006 | Malkin et al. | |
| 7,479,257 B2 | 1/2009 | Nguyen et al. | |
| 7,686,761 B2 | 3/2010 | Jackson et al. | |
| 7,899,681 B2 | 3/2011 | Katzenmaier et al. | |
| 8,246,909 B2 | 8/2012 | Williams et al. | |
| 9,056,147 B2 | 6/2015 | Ma | |
| 9,068,976 B2 | 6/2015 | Putnam et al. | |
| 9,216,440 B2 | 12/2015 | Ma et al. | |
| 9,410,180 B2 | 8/2016 | Pederson et al. | |
| 10,201,269 B2 | 2/2019 | Yang et al. | |
| 10,443,083 B2 | 10/2019 | Eghbal et al. | |
| 10,561,753 B2 | 2/2020 | Thompson et al. | |
| 10,596,287 B2 | 3/2020 | Dang et al. | |
| 10,668,180 B2 | 6/2020 | Thompson et al. | |
| 2002/0009015 A1 | 1/2002 | Laugharn, Jr. et al. | |
| 2003/0083902 A1 | 5/2003 | Hehenberger et al. | |
| 2003/0170901 A1 | 9/2003 | Kippenhan et al. | |
| 2004/0197848 A1 | 10/2004 | Behun et al. | |
| 2013/0217107 A1 | 8/2013 | Pederson et al. | |
| 2013/0323117 A1 | 12/2013 | Ma et al. | |
| 2013/0323120 A1 | 12/2013 | Ma | |
| 2014/0053871 A1 | 2/2014 | Ma et al. | |
| 2014/0235975 A1 | 8/2014 | Carnes | |
| 2014/0264039 A1 | 9/2014 | Kurkowski et al. | |
| 2016/0022852 A1* | 1/2016 | Sakaki ...................... A61L 2/20 422/119 |
| 2016/0235879 A1 | 8/2016 | Andersson et al. | |
| 2017/0252472 A1 | 9/2017 | Dang et al. | |
| 2017/0252473 A1 | 9/2017 | Thompson et al. | |
| 2017/0252474 A1 | 9/2017 | Thompson et al. | |
| 2017/0253845 A1 | 9/2017 | Amin | |
| 2017/0253905 A1 | 9/2017 | Eghbal et al. | |
| 2020/0063179 A1 | 2/2020 | Eghbal et al. | |
| 2020/0330636 A1 | 10/2020 | Thompson et al. | |

FOREIGN PATENT DOCUMENTS

| | | |
|---|---|---|
| CN | 101095961 A | 1/2008 |
| CN | 101189519 A | 5/2008 |
| CN | 102245217 A | 11/2011 |
| CN | 102256631 A | 11/2011 |
| CN | 102364485 A | 2/2012 |
| CN | 102498218 A | 6/2012 |
| CN | 102740898 A | 10/2012 |
| CN | 103119173 A | 5/2013 |
| CN | 103201391 A | 7/2013 |
| CN | 103559572 A | 2/2014 |
| CN | 103606118 A | 2/2014 |
| CN | 104056292 A | 9/2014 |
| CN | 104380333 A | 2/2015 |
| CN | 104567982 A | 4/2015 |
| CN | 204671599 U | 9/2015 |
| CN | 105120906 A | 12/2015 |
| EP | 0629410 A1 | 12/1994 |
| EP | 1617878 A1 | 1/2006 |
| EP | 0981641 B1 | 5/2006 |
| EP | 2340853 A1 | 7/2011 |
| EP | 2792294 A1 | 10/2014 |
| JP | 2000-175995 A | 6/2000 |
| JP | 2003-506156 A | 2/2003 |
| JP | 2008-200126 A | 9/2008 |
| JP | 2009-095502 A | 5/2009 |
| JP | 2009-532090 A | 9/2009 |
| JP | 2010-119491 A | 6/2010 |
| JP | 2012-071029 A | 4/2012 |
| JP | 2012-105713 A | 6/2012 |
| JP | 2014-166209 A | 9/2014 |
| JP | 2014-179973 A | 9/2014 |
| JP | 2016-533251 A | 10/2016 |
| KR | 2018-0038868 A | 4/2018 |
| RU | 2302000 C2 | 7/2007 |
| RU | 2522203 C3 | 7/2014 |
| WO | WO 96/25214 A1 | 8/1996 |
| WO | WO 2001/010475 A1 | 2/2001 |
| WO | WO 2004/093925 A1 | 11/2004 |
| WO | WO 2005/048041 A2 | 5/2005 |
| WO | WO 2006/086547 A2 | 8/2006 |
| WO | WO 2013/181393 A1 | 12/2013 |
| WO | WO 2014/159696 A1 | 10/2014 |
| WO | WO 2015/049002 A1 | 4/2015 |
| WO | WO 2015/080777 A1 | 6/2015 |

OTHER PUBLICATIONS

Tanaka, K., et al., "Evaluation of Perioperative Management Using Information Communication Technology—Construction of a Management System for Sterilization of Medical Instruments, Reservations System for Surgery, and Operation Workflow Management System-," Journal of the Japanese Society of Environmental Infections, 2008, 23(2):104-110, 10 pgs.

Noboru, K., "Sterilization indicator," Japanese Journal of Operating Room Nursing, Special Edition "The basics of sterilization that you should know now," Mar. 2003, (Sequential serial No. 227), 18(3):274-280. (Article not available, Bibliographic material attached. Please consider as prior art until proven otherwise.) 1 pg.

Chinese Search Report dated Jun. 11, 2021 for Application No. CN 201710120894.1, 1 pg.

Japanese Office Action, Notice of Reasons for Refusal, and First Search, dated Dec. 8, 2020 for Application No. JP 2017-038014, 18 pgs.

Japanese Search Report dated Oct. 23, 2020 for Application No. JP2017-038026, 32 pgs.

Japanese Office Action, Notice of Reasons for Refusal, dated Apr. 27, 2021 for Application No. JP 2017-038032, 5 pgs.

Japanese Notification of Reasons for Refusal dated Dec. 8, 2020 for Application No. 2017-038026, 4 pages.

(56) References Cited

OTHER PUBLICATIONS

Russian Office Action and Search Report dated Jun. 27, 2018 for Application No. 2017106748, 10 pages.
Chinese Office Action and Search Report dated Jan. 5, 2021 for Application No. 201710120894.1, 10 pages.
Chinese Final Office Action dated Jan. 22, 2021, for Application No. 201710120892.2, 9 pages.
Chinese Office Action and Search report dated Apr. 14, 2020 for Application No. 201710120892.2, 13 pages.
Chinese Office Action and Search report dated May 7, 2020 for Application No. 201710120893.7, 16 pages.
European Search Report and Written Opinion, Extended, dated Jul. 27, 2017 for Application No. EP 17158975.7, 9 pages.
European Search Report and Written Opinion, Partial, dated Aug. 1, 2017 for Application No. EP 17158813.0, 13 pages.
Extended European Search Report and Written Opinion dated Aug. 2, 2017 for Application No. EP 17158962.5, 8 pages.
European Search Report and Written Opinion, Extended, dated Nov. 9, 2017 for Application No. EP 17158813.0, 11 pages.
U.S. Appl. No. 62/302,257, filed Mar. 2, 2016.
U.S. Appl. No. 62/316,722, filed Apr. 1, 2016.
U.S. Appl. No. 62/376,517, filed Aug. 18, 2016.
Chinese Office Action, The Second Office Action, dated Sep. 30, 2020 for Application No. CN 201710120892.2, 12 pgs.
Chinese Office Action, The First Office Action, and First Search Report dated Jul. 31, 2020 for Application No. CN 201710120894.1, 20 pgs.
European Examination Report dated Sep. 16, 2020 for Application No. EP 17158962.5, 4 pgs.
European Examination Report dated Sep. 16, 2020 for Application No. EP 17158975.7, 4 pgs.
Japanese Search Report dated Jul. 27, 2020 for Application No. JP 2017-038032, 159 pgs.
U.S. Appl. No. 16/868,683, filed May 7, 2020 by Thompson et al., entitled: "Apparatus and Method for Sterilizing Medical Devices."

* cited by examiner

Cycle Information

◁ Back

FLEX CYCLE: 42 minutes*

○ Single channel flexible endoscopes
○ Flexible endoscopes without lumens

Instruments include, but are not limited to:

○ Bronchscopes
○ Hysteroscopes
○ Cystoscopes
○ Flexible ureteroscopes
○ Choledochoscopes
○ Thoracoscopes
○ Intubation fiberscopes

618

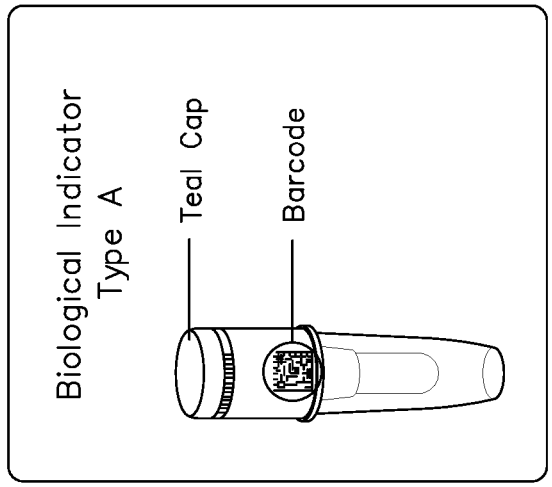

Biological Indicator Type A
— Teal Cap
— Barcode

Please reference the user's guide for complete cycle information regarding recommended items, material, and some typical devices that can be sterilized in each cycle.
*Cycle times are approximate. Load conditioning may increase processing time by approximately 5 minutes.

Fig.9

```
Cycle Completed
┌─────────────────────────────────────────────────┐
│ ✓ Cycle Completed Successfully                   │
│                                                  │
│   Cycle Data:        --                          │
│   Cycle Number:      230              ╱―666      │
│   Cycle Name:        Express                     │
│   Start Time:        05/19/14 02:10:31PM         │
│   Completion Time:   05/19/14 02:34:53PM         │
│   Elapsed Time:      00:24:22                    │
│   Operator:          a                           │
│                                                  │
│   [  View Details  ]        [     Done      ]    │
└─────────────────────────────────────────────────┘
```

Fig.16

```
Positive Biological Indicator Alert
    668                      ⚠
         Biological Indicator Failed (Positive)
                Biological indicator number: 12345 ← 670
              Time of Failed Biological Indicator: 01/21/2015 11:13AM ← 672
Cycles affected:
```

| Cycle # | Cycle Completion Time | Cycle Type | Biological Indicator Result |
|---|---|---|---|
| 78 | 01/21/2015 at 3:13PM | STANDARD | Positive |
| 77 | 01/21/2015 at 1:13PM | DUO | None |
| 76 | 01/21/2015 at 11:13PM | EXPRESS | None |
| 75 | 01/21/2015 at 9:13PM | STANDARD | None |

674   676   678   680 Confirm

Fig.17

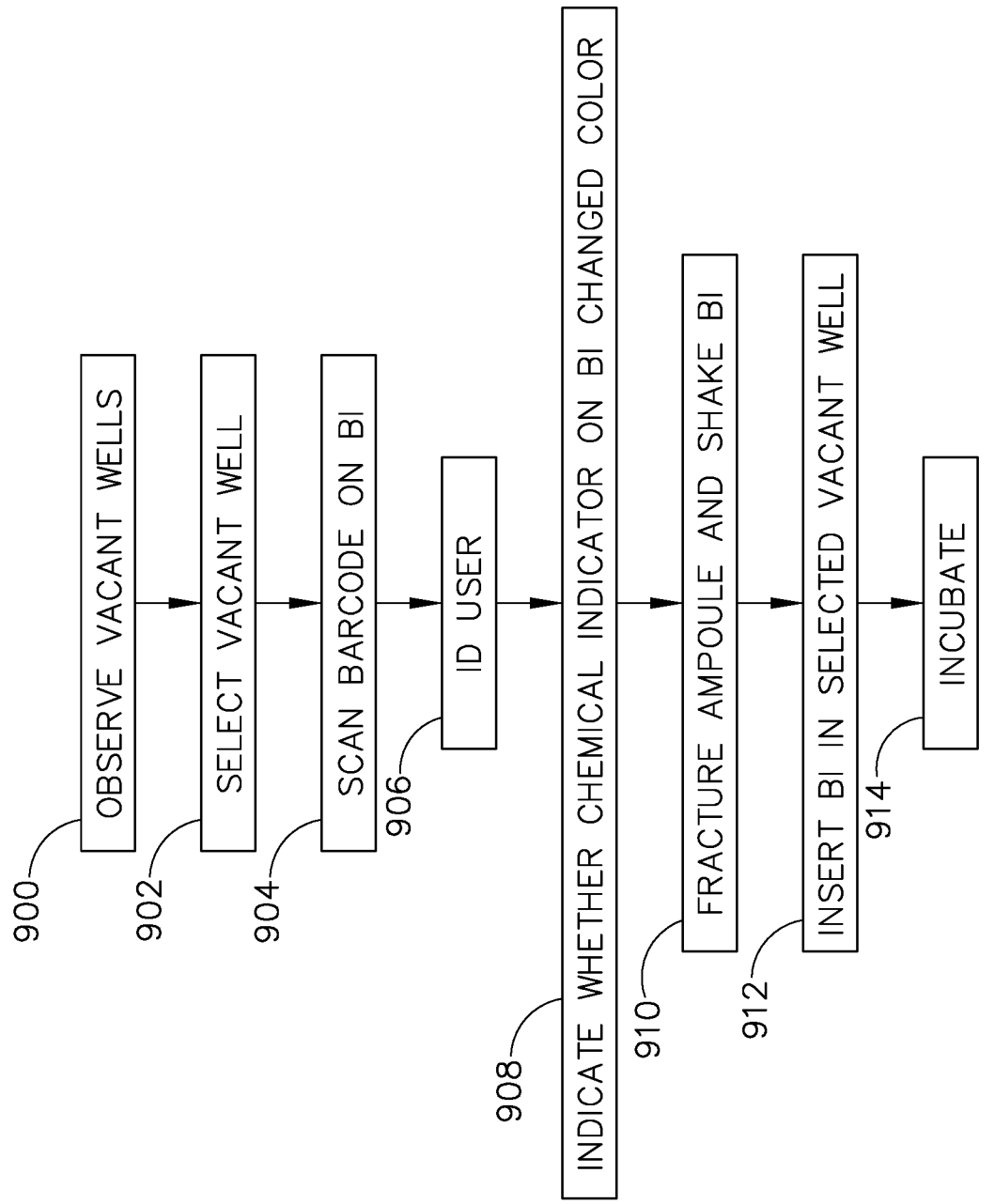

In-Progress Test Summary, Well No.6

Biological Indicator Info:

| | |
|---|---|
| Biological Indicator: | Test |
| Lot Number: | 123456-01 |
| Serial Number: | 987654321 |
| Expiration Date: | 01/2017 |
| Added By: | John Smith |
| Time Added: | 10:53 AM |
| Date: | 09/23/2015 |
| Chemical Indicator Color Change: | Yes |
| Temperature: | 60.0° C |

←── 450

STERRAD Cycle Info:

| | |
|---|---|
| STERRAD ID: | 1-100NX 123456 |
| Cycle Type: | Standard |
| Cycle #: | 123 |
| Cycle Start Time: | 9:50 AM |
| Cycle End Time: | 10:40 AM |
| Cycle End Date: | 09/23/2015 |

◁ ▷

Done

Cycle #20, #001, CSSD

STERRAD Cycle Info ← 1432

| | |
|---|---|
| Cycle Status: | ☑ Completed |
| STERRAD ID: | #001 |
| Cycle #: | 20 |
| Cycle Type: | STANDARD |
| Load Conditioning: | Disabled |
| Operator: | D.Thomas |
| Cycle Date: | 09-Feb-2016 |
| Cycle Start Time: | 12:01 PM |
| Cycle End Time: | 12:55 PM |
| Elapsed Time: | 55 Mins |
| Facility Name: | -- |
| Department Name: | CSSD |
| Cassette lot Number: | 123456-01 |
| Biological Indicator: | Processed |
| Cycle Notes: | -- |

Test Biological Indicator Info ← 1434

| | |
|---|---|
| Biological Indicator Result: | ◯ Failed (Positive) |
| Biological Indicator Reader: | Velocity 1 |
| Biological Indicator: | Test |
| Lot Number: | 123456-01 |
| Serial Number: | 987654321 |
| Expiration Date: | 01/20/17 |
| Added By: | J.Smith |
| Time Added: | 01:45 AM |
| Date Added: | 20-Oct-2015 |
| Result Time: | 02:15 PM |
| Chemical Indicator Color Change: | Yes |
| Temperature: | 60°C |

Cycle Summary | Cycle Files

Device Management ✕

Device Pairing — STERRAD 1  1502

1501 → Connect one end of an Ethernet cable to the device and the other end to the hospital network port.

IP Address*  10.20.171.86

Test Connection

Share Settings  ⓘ Input this in formation into STERRAD 1.

1500

Folder Name*  Share Settings    Username*  STERRAD

Password*

1504

ITS DTI Settings ⓘ

ITS  STERRAD 100NX    Folder Name  10033-103423

Submit

List of Devices        Add Device

Fig.60

Device Management ✕

Device Pairing — Velocity 1

Connect one end of an Ethernet cable to the device and the other end to the hospital network port.

IP Address*  10.20.171.86        Test Connection

Pairing Code*  87DFg00L          Regenerate Code 1506                              1508

Submit

List of Devices        Add Device ately; U.S. Pat. No. 11,766,495 B2

METHOD OF STERILIZING MEDICAL DEVICES, ANALYZING BIOLOGICAL INDICATORS, AND LINKING MEDICAL DEVICE STERILIZATION EQUIPMENT

This application is a continuation of U.S. patent application Ser. No. 15/441,786, entitled "Method of Sterilizing Medical Devices, Analyzing Biological Indicators, and Linking Medical Device Sterilization Equipment," filed Feb. 24, 2017, and issued as U.S. Pat. No. 10,561,753 on Feb. 18, 2020.

PRIORITY

This application claims priority to U.S. Provisional Patent Application No. 62/302,257, entitled "System and Method for Sterilizing Medical Devices," filed Mar. 2, 2016, the disclosure of which is incorporated by reference herein.

This application also claims priority to U.S. Provisional Patent Application No. 62/316,722, entitled "System and Method for Sterilizing Medical Devices," filed Apr. 1, 2016, the disclosure of which is incorporated by reference herein.

This application also claims priority to U.S. Provisional Patent Application No. 62/376,517, entitled "Apparatus and Method to Link Medical Device Sterilization Equipment," filed Aug. 18, 2016, the disclosure of which is incorporated by reference herein.

BACKGROUND

Re-usable medical devices such as certain surgical instruments, endoscopes, etc., may be sterilized before re-use in order to minimize the likelihood that a contaminated device might be used on a patient, which could cause an infection in the patient. Various sterilization techniques may be employed, such as steam, hydrogen peroxide, and vapor phase sterilization, either with or without a gas plasma and ethylene oxide (EtO). Each of these methods may depend to a certain extent on the diffusion rates of the sterilization fluids (e.g., gases) upon the medical devices to be sterilized.

Before sterilization, medical devices may be packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device.

Although the packaging may help prevent contamination of a sterile medical device, the packaging may increase the difficulty of achieving a successful sterilization cycle because the packaging may impede the sterilant from reaching the medical device contained therein. This may be particularly problematic for medical devices that have diffusion-restricted spaces therein because these diffusion-restricted spaces may reduce the likelihood that a sterilization cycle may be effective. For example, some endoscopes have a long narrow lumen into which the sterilant must diffuse in sufficient concentration for sufficient time to achieve a successful sterilization cycle.

Sterilization of medical devices may be performed with an automated sterilization system such as a STERRAD® System by Advanced Sterilization Products of Irvine, Calif. Examples of automated sterilization systems are described in U.S. Pat. No. 6,939,519, entitled "Power System for Sterilization Systems Employing Low Frequency Plasma," issued Sep. 6, 2005, the disclosure of which is incorporated by reference herein; U.S. Pat. No. 6,852,279, entitled "Sterilization with Temperature-Controlled Diffusion Path," issued Feb. 8, 2005, the disclosure of which is incorporated by reference herein; U.S. Pat. No. 6,852,277, entitled "Sterilization System Employing a Switching Module Adapter to Pulsate the Low Frequency Power Applied to a Plasma," issued Feb. 8, 2005, the disclosure of which is incorporated by reference herein; and U.S. Pat. No. 6,447,719, entitled "Power System for Sterilization Systems Employing Low Frequency Plasma," issued Sep. 10, 2002, the disclosure of which is incorporated by reference herein. Medical devices must be carefully arranged and controlled within the sterilization system to maintain an environment that allows for effective sterilization. Each different medical device may require a different arrangement and sterilization process, meaning that use of a sterilization system can still be error prone and may heavily rely upon operator training and knowledge, or related documentation.

In addition, re-use of the same sterilizing chamber of a sterilization system may result in cross contamination, particularly when the sterilization system is not operated correctly. Operator error may result in medical devices that are erroneously believed to be decontaminated being returned to service. Confirming that a sterilization cycle has been efficacious may help medical personnel avoid using a contaminated medical device on a patient. The sterilized medical device might not itself be checked for contaminating organisms because such an activity may introduce other contaminating organisms to the medical device, thereby re-contaminating it. Thus, an indirect check may be performed using a sterilization indicator. A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms may be placed into a sterilization chamber alongside a medical device and subject to a sterilization cycle. After the cycle is complete, the microorganisms in the biological indicator may be cultured to determine whether any of the microorganisms survived the cycle.

In view of the foregoing, it may be desirable to provide a sterilization system that minimizes opportunities for operator error, thereby maximizing the likelihood of successful sterilization cycles, thereby minimizing the risk of patient infection. While a variety of systems and methods have been made and used for surgical instrument sterilization, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 9 depicts a screenshot of an exemplary user interface that could be presented via the sterilizing cabinet of the system of FIG. 1, to provide information to a user for configuring a "flex" sterilization cycle;

FIG. 16 depicts a screenshot of an exemplary user interface that could be presented via the sterilizing cabinet of the system of FIG. 1, to deliver results to a user for a completed sterilization cycle;

FIG. 17 depicts a screenshot of an exemplary user interface that could be presented via the sterilizing cabinet of the system of FIG. 1, to identify cycles associated with a positive biological indicator result as communicated from an indicator analyzer of the system of FIG. 1 via a communication hub of the system of FIG. 1;

FIG. 22 depicts a flowchart of exemplary steps that may be performed by the indicator analyzer of FIG. 20 in preparation for analysis of the biological indicator assembly of FIG. 19;

FIG. 32 depicts a screenshot of an exemplary user interface that could be presented via a display of the indicator analyzer of FIG. 20 to provide a detailed status of an indicator during incubation and analysis;

FIG. 46 shows an example of an interface that may be used to view information about a medical device processing component and its tasks via a user device coupled with the communication hub of FIG. 39 or directly via the communication hub of FIG. 40;

FIG. 47 shows an example of an interface that may be used to view additional information on a medical device processing component's tasks via a user device coupled with the communication hub of FIG. 39 or directly via the communication hub of FIG. 40;

FIG. 48 shows an example of an interface that may be used to view additional information on a medical device processing component's tasks via a user device coupled with the communication hub of FIG. 39 or directly via the communication hub of FIG. 40;

FIG. 59 shows an example of an interface that may be used to provide guidance to a user while adding a medical device processing component to a network via a user device coupled with the communication hub of FIG. 39 or directly via the communication hub of FIG. 40; and FIG. 60 shows an example of an interface that may be used to provide guidance to a user while adding a medical device processing component to a network via a user device coupled with the communication hub of FIG. 39 or directly via the communication hub of FIG. 40.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Sterilization System and Devices

Figure 1:
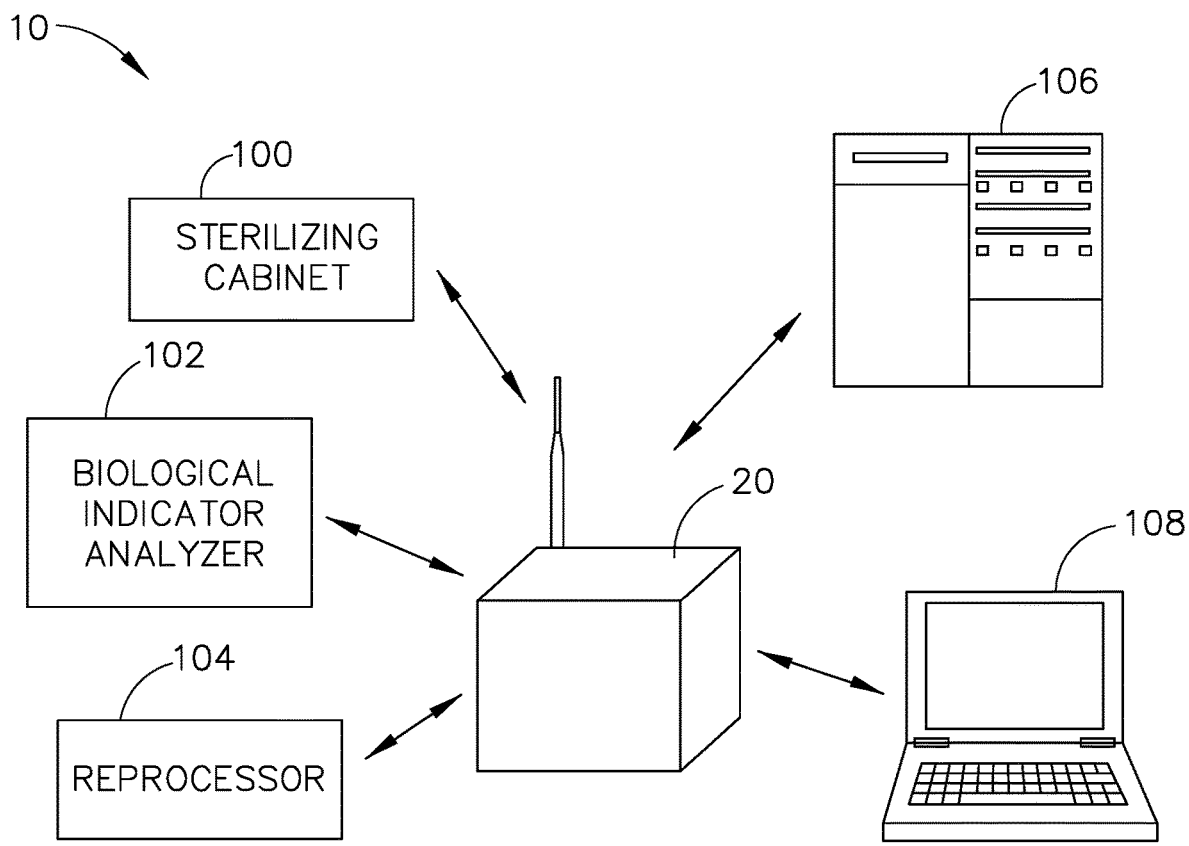
FIG. 1 depicts a schematic view of an exemplary sterilization system.

FIG. 1 depicts a schematic view of an exemplary system (10) of interconnected devices that may be configured to perform methods for sterilizing medical devices. System (10) of this example includes a sterilizing cabinet (100), a biological indicator analyzer (102), a medical device reprocessor (104), a communication hub (20), a server (106), and a user device (108). As will be described in greater detail below, sterilizing cabinet (100) may have a sealable sterilization chamber where contaminated medical devices may be placed. A user may interact with sterilizing cabinet (100) via a set of user inputs, such as physical buttons, a keyboard, a touch pad or mouse, other controls, and/or a touch screen display interface. A display of sterilizing cabinet (100) may provide users with information, configuration options, status and duration of sterilization cycles and preparation, and other similar information.

Sterilizing cabinet (100) is in communication with a server (106), such as a hospital record server or hospital local area network server. Server (106) may receive information from sterilizing cabinet (100) relating to sterilization procedures performed by the sterilizing cabinet (100), such as sterilization procedure durations and results; whether a particular sterilization procedure provided a subsequent indication of biological contamination; the identification of a user or technician who initiated, canceled, or complete a sterilization procedure; consumable materials or supplies used during a sterilization procedure; diagnostic information and systems errors; and/or other information. Server (106) may also provide information to the sterilizing cabinet (100) such as software updates, configuration updates, user authentication information, biological indicator use protocols, and other information. Communication between sterilizing cabinet (100) and server (106) may be accomplished via any suitable wired and/or wireless communication technology, such as Ethernet, Wi-Fi, Bluetooth, USB, infrared, NFC, and/or other technologies.

In system (10) of the present example, sterilizing cabinet (100) is also in communication with a communication hub (20), which itself is in communication with one or more biological indicator analyzers (102). As will be described in greater detail below, biological indicator analyzer (102) may comprise a desktop or wall mounted device that receives a biological indicator and measures one or more characteristics of the biological indicator in order to gather data that may be used to determine whether the biological indicator tests positive, indicating that contamination is present after a sterilization procedure; or negative, indicating that no contamination is present after the sterilization procedure.

In some versions, biological indicator analyzer (102) will measure and transmit data to communication hub (20), which will process the data to determine if there is contamination. In other versions, biological indicator analyzer (102) itself may both measure and analyze the data to determine whether there is contamination, and communication hub (20) may be used to receive, gather, and transmit such information to sterilizing cabinet (100) and/or other devices as will be described in greater detail below. In still other versions, biological indicator analyzer (102) and communication hub (20) may be different components of a single device; or may be components of sterilizing cabinet (100). Such variations may be desirable depending upon a particular implementation environment and user needs, such that a single device incorporating sterilizing cabinet (100), communication hub (20), and/or biological indicator analyzer (102) may be desirable in a semi-portable unit; while an implementation supporting a one-to-many relationship between sterilizing cabinet (100) and biological indicator analyzer (102) may be more advantageous for permanent installation in a large hospital with many users.

As will be described in greater detail below and as alluded to above, communication hub (20) is configured to process and relay information from biological indicator analyzer (102) to sterilizing cabinet (100). Biological indicator analyzer (102) and sterilizing cabinet (100) may each be coupled with communication hub (20) via any suitable wired and/or wireless communication technology, such as Ethernet, Wi-Fi, Bluetooth, USB, infrared, NFC, and/or other technologies. It should also be understood that communication hub (20) may be in communication with various other components, via wire or wirelessly, including but not limited to various user devices (108) such as desktop computers, laptop computers, mobile computing devices, smartphones, etc. Moreover, communication hub (20) may be in communication with server (106) via wire or wirelessly.

In versions where communication hub (20) is in communication with server (106), communication hub (20) may relay data, etc., between sterilizing cabinet (100) and server (106), such that communication hub (20) serves as an intermediary between sterilizing cabinet (100) and server (106). It should therefore be understood that, in some versions, sterilizing cabinet (100) may be in communication with server (106) via communication hub (20) instead of being directly in communication with server (106). Similarly, communication hub (20) may serve as an intermediary between sterilizing cabinet (100) and biological indicator analyzer (102); between sterilizing cabinet (100) and user device (108); between biological indicator analyzer (102) and server (106); between biological indicator analyzer (102) and user device (108); between reprocessor (104) and server (106); between reprocessor (104) and user device (108); and/or between user device (108) and server (106). Various suitable components and configurations that may be used to form communication hub (20) will be apparent to those of ordinary skill in the art in view of the teachings herein.

II. Exemplary Sterilization Processes and Interfaces

A. Overview of Sterilization Process

Figure 2:
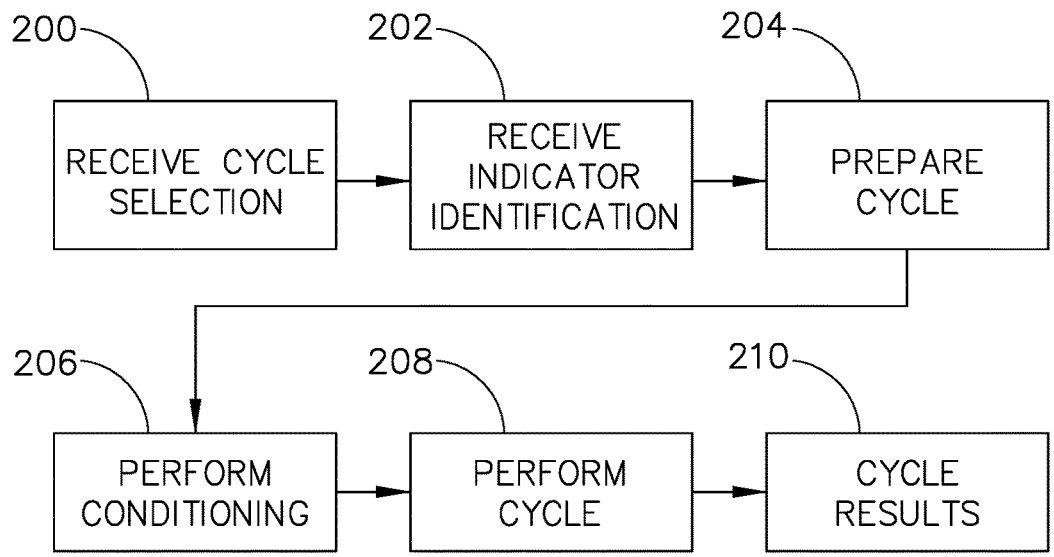
FIG. 2 depicts a high level flowchart of an exemplary set of steps that a sterilizing cabinet of the system of FIG. 1 could perform to sterilize a medical device.

FIG. 2 depicts a high level flowchart of an exemplary set of steps that system (10) could perform to sterilize a medical device. A user may interact with the system via a user interface such as a keyboard or touch screen of sterilizing cabinet (100), as will be described in greater detail below; or via an input device in communication with sterilizing cabinet (100). Initially, sterilizing cabinet (100) may display one or more sterilization cycles via a display and then receive a sterilization cycle selection (block 200) from the user. Sterilizing cabinet (100) may be configured to perform one or more sterilization cycles, with different sterilization cycles being appropriate for different types and quantities of medical devices.

Sterilizing cabinet (100) may also display instructions indicating whether a biological indicator should be used with the selected sterilization cycle, and receive a biological indicator identification (block 202). A biological indicator may be placed inside a sterilization chamber of sterilizing cabinet (100) before the sterilization cycle begins and may remain in the sterilization chamber during a sterilization cycle. The user may thus identify the particular biological indicator (block 202) before the biological indicator is placed in the sterilization chamber. The biological indicator may contain microorganisms that are responsive to a particular sterilization cycle. Upon completion of the sterilization cycle, the biological indicator may be tested for the microorganisms in order to provide a measure of the effectiveness of the sterilization cycle. A biological indicator may not necessarily be required for all sterilization cycles, but may be required based on hospital rules or local regulations. When used, a biological indicator may be identified by manual input, such as keyboard entry of a biological indicator type or identifier; or may be identified automatically, such as by an optical scan of an optical identifier or a wireless scan of an RFID or other unique identifier.

Selection of a sterilization cycle (block 200) and identification of a biological indicator (block 202) may define one or more requirements for the configuration and arrangement of medical devices within sterilizing cabinet (100). A door of the sterilization chamber of sterilizing cabinet (100) may be opened and instructions may be displayed to guide a user through preparation of the sterilization cycle (block 204), including placement of the biological indicator, placement of medical devices, closing the door of the sterilization chamber of the sterilization cabinet (100), and/or other changes in preparation. Before initiating the actual sterilization cycle (block 208), sterilization cabinet (100) may also perform load conditioning (block 206) of the medical devices that are loaded in the sterilization chamber of the sterilization cabinet (100). Such load conditioning (block 206) may include verifying that the sterilization chamber is sealed; verifying contents of the sterilization chamber; checking physical characteristics of the contents of the sterilization chamber such as moisture levels, content volume, content weight, internal temperature, or other characteristics; and/or performing one or more conditioning steps that may include heat treatment, chemical treatment, plasma treatment, or other types of treatment to reduce moisture, raise temperature, and/or otherwise prepare the medical devices in the sterilization chamber for the sterilization cycle.

Once the load conditioning (block 206) has been completed, the selected sterilization cycle itself may be performed (block 208). The sterilization cycle (block 208) may include exposing the medical device(s) in the sterilizing chamber to pressurized sterilant gas, further heat treatment, chemical treatment, plasma treatment, vacuum treatment, and/or other types of sterilization procedures. After the sterilization cycle (block 208) is completed, the complete sterilization results may be displayed to a user via a display of the sterilization cabinet; transmitted to server (106); printed locally; and/or displayed, transmitted, and/or stored via other devices as may be desirable.

Sterilization cabinet (100) may also provide results (block 210) of the sterilization cycle. This provision of results (block 210) may include results from analysis of a biological indicator via biological indicator analyzer (102) as described below. These results may include a positive or negative indication of contamination present in the biological indicator at the completion of the sterilization cycle (block 208). In cases where the biological indicator suggests that contamination is present after completion of the sterilization cycle (block 208), additional actions may be taken such as alerting a user of the positive test and analysis of sterilization cycle history in order to determine if other past cycles may be the cause of the contamination; and/or if subsequently sterilized medical devices may need to be re-sterilized.

Figure 3:
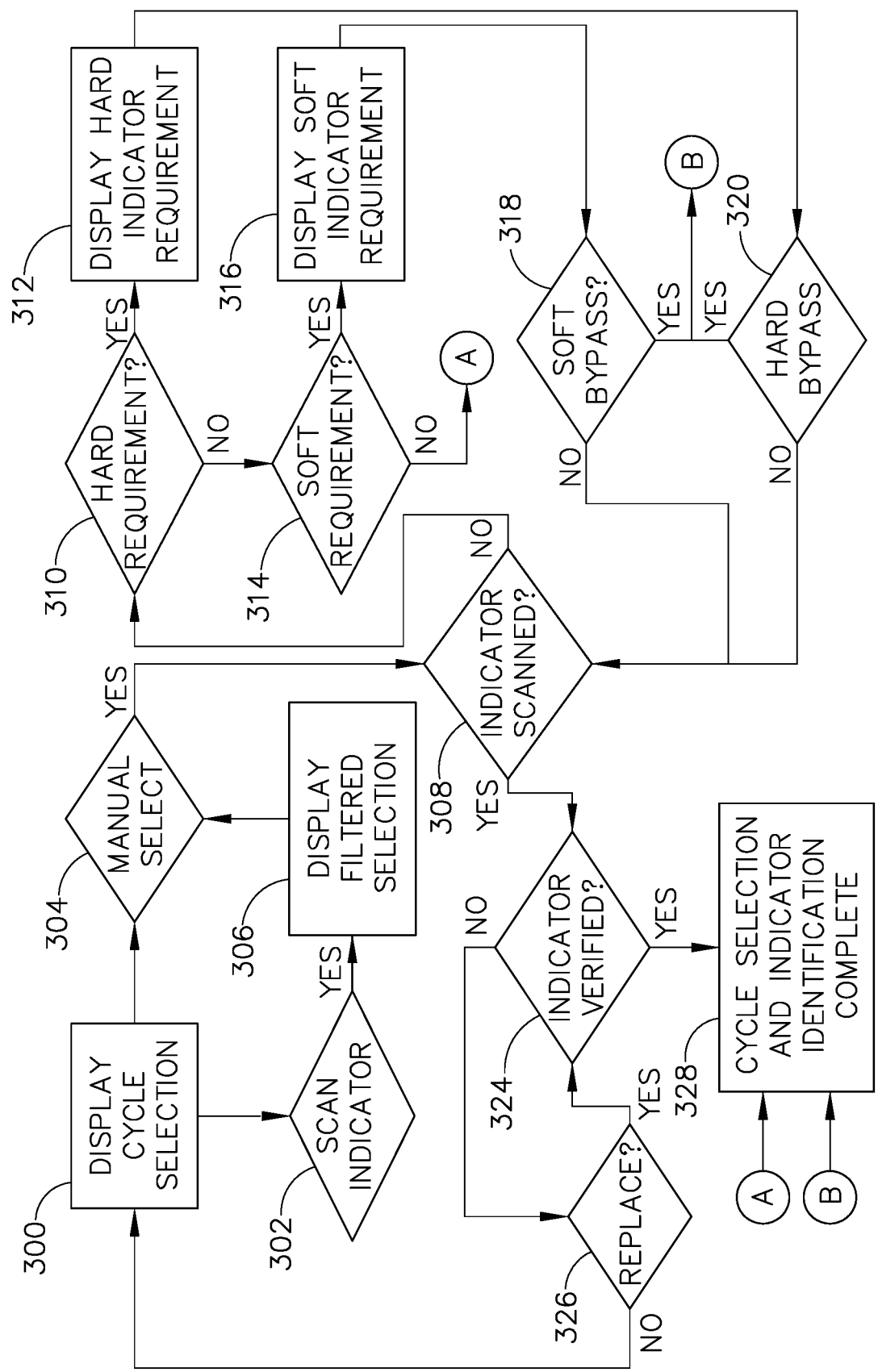
FIG. 3 depicts a flowchart of an exemplary set of steps that the sterilizing cabinet of the system of FIG. 1 could perform to determine a sterilization cycle and associated configuration.

B. Exemplary Sterilization Cycle Selection and Biological Indicator Identification FIG. 3 shows an exemplary set of steps that sterilizing cabinet (100) could perform to receive a sterilization cycle selection (block 200) and receive a biological indicator identification (block 202). In other words, the method shown in FIG. 3 may be viewed as showing several sub-steps that may be performed as part of the sterilization cycle selection step (block 200) and the biological indicator identification step (block 202) of FIG. 2.

Figure 6:
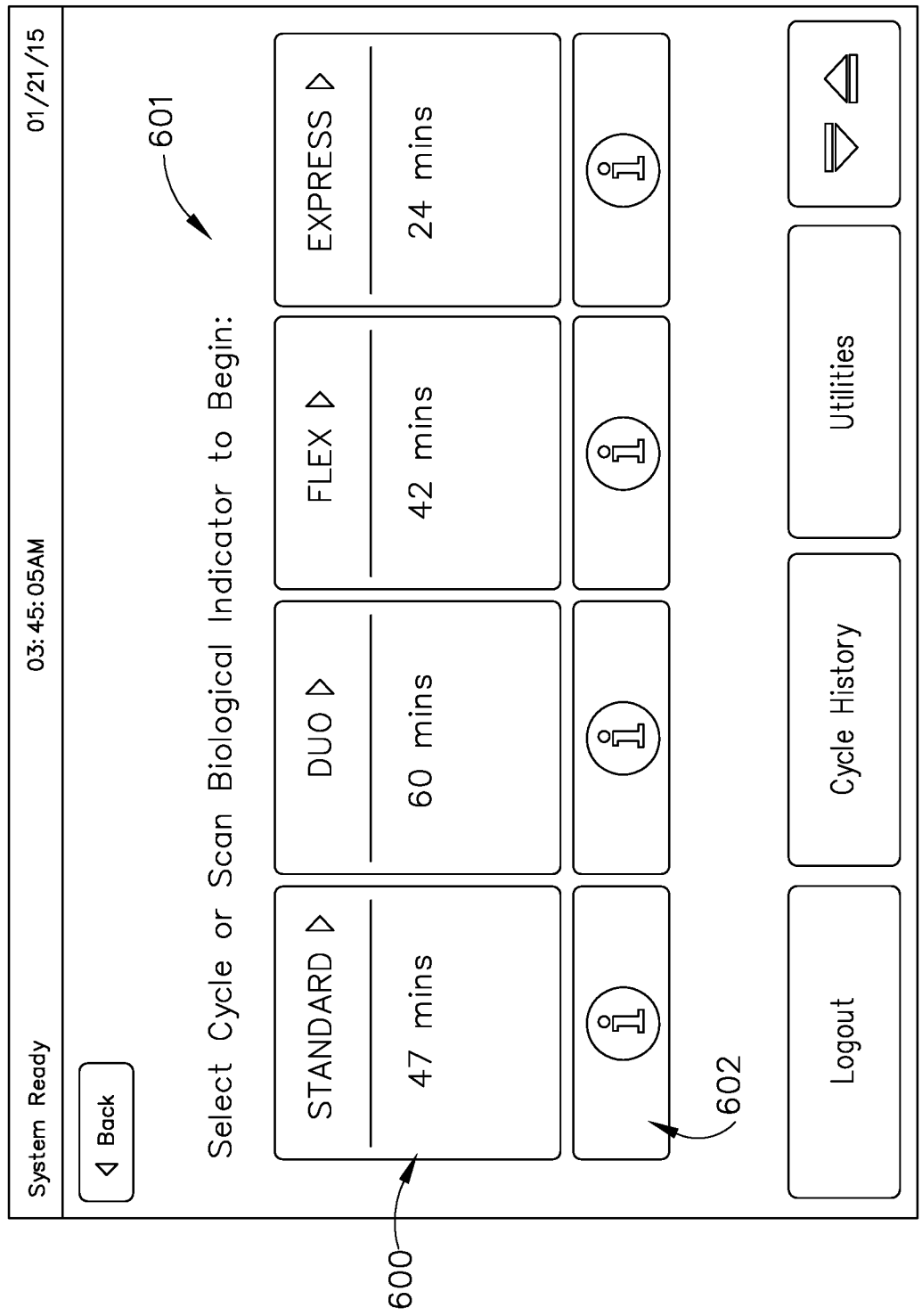
FIG. 6 depicts a screenshot of an exemplary user interface that could be presented via the sterilizing cabinet of the system of FIG. 1, to select a sterilization cycle.

When a user initially interacts with sterilizing cabinet (100), after logging in or otherwise authenticating their use of the sterilizing cabinet (100), sterilizing cabinet (100) may display a sterilization cycle selection (block 300) to the user via a graphical user interface such as the one shown in FIG. 6. As shown in FIG. 6, a sterilization cycle selection button (600) is a touch screen element that shows the sterilization cycle type, such as "standard," "duo," "flex," and "express;" and may show additional information such as sterilization cycle duration, a type of biological indicator associated with a sterilization cycle, and other information, for each sterilization cycle selection, as well as instructions for either selecting a cycle or scanning a biological indicator (601). The sterilization cycle selection screen of FIG. 6 also includes a sterilization cycle information button (602) for each sterilization cycle selection, which may be selected by a user to display additional information that may help a user make a sterilization cycle choice. It should be understood that the "standard," "duo," "flex," and "express" sterilization cycles of the present example are merely illustrative. Sterilization cabinet (100) may alternatively offer any other suitable number and types of sterilization cycles for selection.

While FIG. 6 shows each sterilization cycle being associated with a specific type of biological indicator, such as Biological Indicator Apollo Type A, or Biological Indicator Apollo Type B, different embodiments may support different configurations of biological indicator type. In some embodiments, each sterilization cycle may have a different type of biological indicator, such that there may be four or more different types of biological indicator each with a specific application. However, in other embodiments, a single biological indicator may be adapted for use with any sterilization cycle, such that only one type of biological indicator is needed. The number and type of biological indicator required for different sterilization cycle may vary depending upon the desired cost, shelf life, market of sale, or other factors. While the embodiment shown in FIGS. 6 through 17 requires a Type A and Type B indicator, the technology and interfaces shown could be modified to support as few as one type of biological indicator, or as many of a plurality of biological indicator as may be needed.

Figure 7:
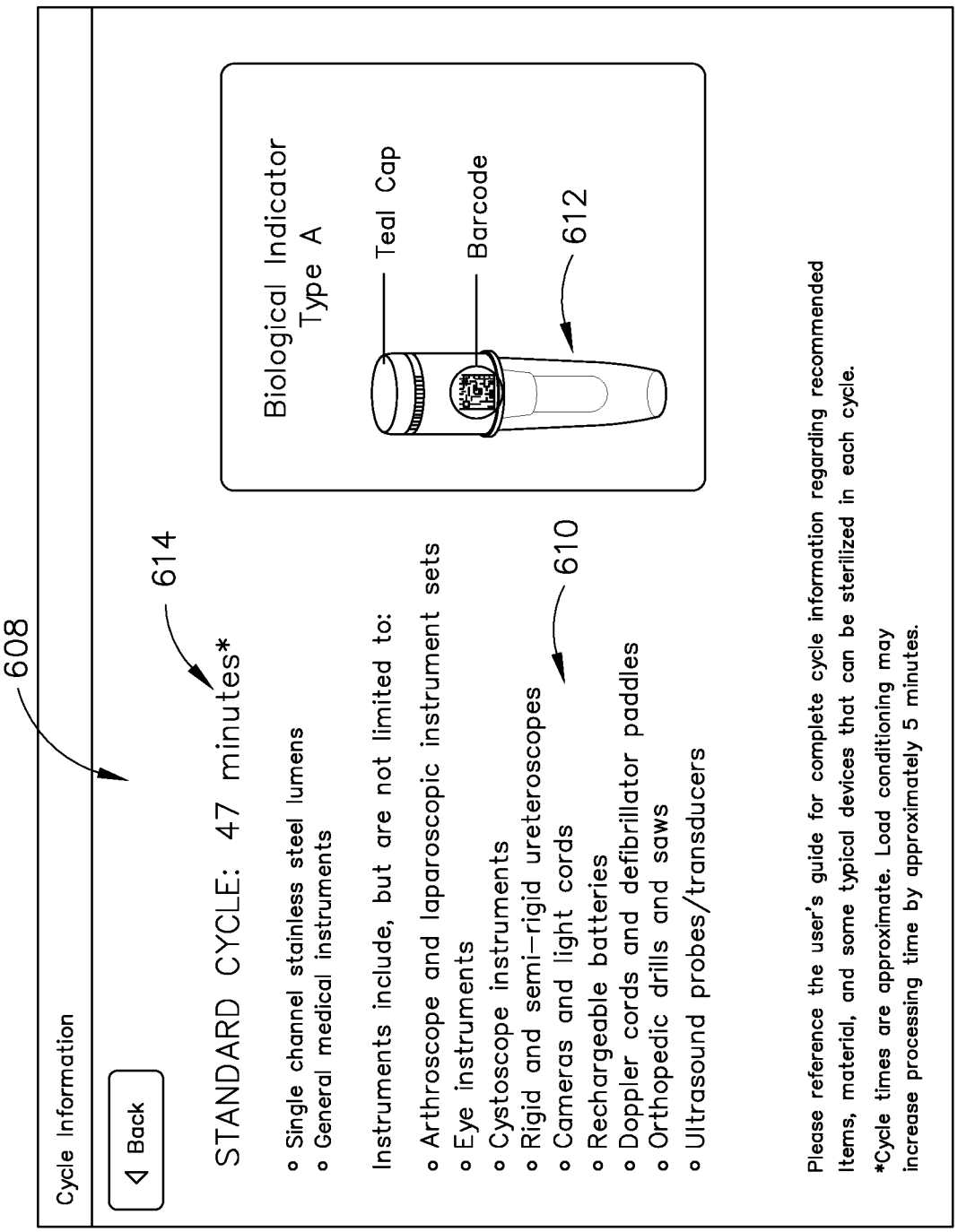
FIG. 7 depicts a screenshot of an exemplary user interface that could be presented via the sterilizing cabinet of the system of FIG. 1, to provide information to a user for configuring a "standard" sterilization cycle.

FIGS. 7-10 show examples of sterilization cycle information screens that may be displayed after interaction with a sterilization cycle information button (602). FIG. 7 shows an exemplary cycle information screen for a "standard" sterilization cycle, which includes a sterilization cycle description (608); a sterilization cycle duration estimate (614); a listing of medical devices (610) suitable for that particular sterilization cycle; and a biological indicator visual aid (612) identifying the type, color, and barcode or identifier location for a biological indicator that is compatible with that particular sterilization cycle. In this particular example, the sterilization cycle description (608) indicates that the "standard" sterilization cycle has a cycle time of approximately 47 minutes; and is intended for instruments including single channel stainless steel lumens and general medical instruments. The listing of medical devices (610) includes the examples of arthroscope and laparascopic instrument sets, eye instruments, cystoscope instruments, rigid and semi-rigid ureteroscopes, cameras and light cords, rechargeable batteries, Doppler cords and defibrillator paddles, orthopedic drills and saws, and ultrasound probes/transducers. The biological indicator visual aid (612) shows that the biological indicator for the "standard" sterilization cycle is a "Type A" biological indicator with a teal cap, though it should be understood that other types, colors, and configurations may also be shown.

Figure 8:
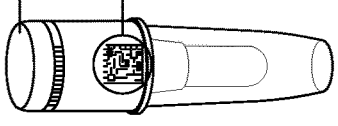
FIG. 8 depicts a screenshot of an exemplary user interface that could be presented via the sterilizing cabinet of the system of FIG. 1, to provide information to a user for configuring a "duo" sterilization cycle.
Figure 10:
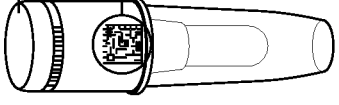
FIG. 10 depicts a screenshot of an exemplary user interface that could be presented via the sterilizing cabinet of the system of FIG. 1, to provide information to a user for configuring a "express" sterilization cycle.

FIGS. 8-10 show similar information for a "duo" sterilization cycle (616), "flex" sterilization cycle (618), and "express" sterilization cycle (620). In particular, in FIG. 8, the sterilization cycle description (616) indicates that the "duo" sterilization cycle has a cycle time of approximately 60 minutes; and is intended for instruments including single channel flexible endoscopes, flexible endoscopes without lumens, cameras, and accessory light cords. The listing of medical devices for the "duo" sterilization cycle includes the examples of bronchoscopes, hysteroscopes, cystoscopes, flexible ureteroscopes, choledochoscopes, thoracoscopes, intubation fiberscopes, light cords, and cameras. The biological indicator visual aid for the "duo" sterilization cycle shows that the biological indicator for the "duo" sterilization cycle is a "Type A" biological indicator with a teal cap, though it should be understood that other types, colors, and configurations may also be shown.

In FIG. 9, the sterilization cycle description (618) indicates that the "flex" sterilization cycle has a cycle time of approximately 42 minutes; and is intended for instruments including single channel flexible endoscopes and flexible endoscopes without lumens. The listing of medical devices for the "flex" sterilization cycle includes the examples of bronchoscopes, hysteroscopes, cystoscopes, flexible ureteroscopes, choledochoscopes, thoracoscopes, and intubation fiberscopes. The biological indicator visual aid for the "flex" sterilization cycle shows that the biological indicator for the "flex" sterilization cycle is a "Type A" biological indicator with a teal cap, though it should be understood that other types, colors, and configurations may also be shown.

In FIG. 10, the sterilization cycle description (620) indicates that the "express" sterilization cycle has a cycle time of approximately 24 minutes; and is intended for general medical devices requiring surface sterilization, sterilization of mated stainless steel, and titanium surfaces. The listing of medical devices for the "express" sterilization cycle includes the examples of da Vinci endoscopes, rigid or semi-rigid endoscopes without lumens, general surgery devices without lumens, rechargeable batteries, eye instruments without lumens, and ultrasound probes/transducers. The biological indicator visual aid for the "express" sterilization cycle shows that the biological indicator for the "flex" sterilization cycle is a "Type B" biological indicator with a dark gray, though it should be understood that other types, colors, and configurations may also be shown.

Sterilization cycle information screens such as those illustrated in FIGS. 7-10 may show additional information, such as pictures and images of medical devices that may be sterilized by the sterilization cycle, sterilization methods used during the sterilization cycle, maximum heat or pressure reached within the sterilization chamber during the sterilization cycle, the number of times the sterilization cycle has been run during a period of time, the last time the sterilization cycle was run, and/or any other information that a user may find useful.

Referring to FIGS. 3 and 6 together, the sterilization cycle selection screen of FIG. 6 may additionally instruct a user to manually select (block 304) a sterilization cycle and/or select and scan a biological indicator (block 302). If a user chooses to scan a biological indicator (block 302) (e.g., using an optical or wireless scanner to scan a barcode, QR code, optical identifier, RFID, or other wireless identifier of a biological indicator), the display may be updated to instead show a filtered selection (block 306) of sterilization cycles that may be selected because they are compatible with the selected and scanned biological indicator (block 302). In some implementations, interface may be shown with sterilization cycle selections that have been filtered (block 306) based upon a scanned or selected biological indicator (block 302). One example is a screen that has a sterilization cycle associated with a "type B" biological indicator grayed out and being rendered un-selectable. This particular screen is presented in response to a "type A" biological indicator being selected or scanned (block 304), such that the screen only enables selection of filtered sterilization cycles that are particularly associated with the "type A" biological indicator. Another example is a screen that has the sterilization cycles associated with a "type A" biological indicator grayed out and being rendered un-selectable. This particular screen is presented in response to a "type B" biological indicator being selected or scanned (block 304), such that the screen only enables selection of the filtered sterilization cycle that is particularly associated with the "type B" biological indicator. However, in embodiments that support or require only one type of biological indicator, the process of filtering by supported sterilization cycle type after selecting a biological indicator would not be required.

Referring back to FIGS. 3 and 6 together, a user may not always scan a biological indicator (block 302) before making a sterilization cycle selection. The user may instead make a manual selection (block 304) from any of the displayed sterilization cycle selection buttons (600). After making a manual selection (block 304) of a sterilization cycle, if the user also scanned or selected a biological indicator (block 308) earlier in the process, then the biological indicator may be verified (block 324) for the selected sterilization cycle. Verification (block 324) may include verifying compatibility with system (10) generally, compatibility with the sterilization cycle selected, verifying that the biological indicator is not expired, and/or other verifications.

A number of exemplary interfaces may be used to indicate to a user that there is a warning or error related to the biological indicator based upon the verification (block 324). A warning message may be displayed when the biological indicator is from a third party manufacturer where the compatibility of the biological indicator with sterilizing cabinet (100), biological indicator analyzer (102), and/or other devices of system (10) has not been verified or validated. The warning message may include buttons to cancel the use of the biological indicator to give the user a chance to replace the biological indicator with a verified biological indicator (block 326); or bypass the warning and continue to complete the sterilization cycle and indicator selection (block 328).

A warning message may be displayed when the identified biological indicator is incompatible with the selected sterilization cycle, such as when a "type A" biological indicator is selected and an "express" sterilization cycle is selected. The warning message may be accompanied by buttons that allow a user to cancel the biological indicator and sterilization cycle selections entirely; or to replace the mismatched biological indicator with a new biological indicator that is compatible with the selected sterilization cycle (block 326). Other warning message may be displayed to indicate to a user that the selected "type B" biological indicator is not valid for use with the selected "standard," "flex," or "duo" sterilization cycle. Again, this warning message may be accompanied by buttons allowing the user to cancel the biological indicator and sterilization cycle selections entirely; or to replace the mismatched biological indicator with a new biological indicator that is compatible with the selected sterilization cycle (block 326). However, in embodiments where only a single type of biological indicator is supported or required, the warning messages described above would not be required to indicate a mismatch between a selected cycle and a selected biological indicator.

Some exemplary interfaces may be displayed when a user selects or scans a biological indicator that is unidentifiable or entirely incompatible with sterilizing cabinet (100), biological indicator analyzer (102), and/or other devices. These warning messages indicate to the user that the currently selected biological indicator is known to be incompatible and must be replaced with a compatible biological indicator before continuing. These messages may be displayed along with buttons allowing a user to cancel the biological indicator and sterilization cycle selections entirely; or to replace the current biological indicator with a new biological indicator that is compatible with the selected sterilization cycle (block 326).

Other exemplary interfaces may be displayed when a user selects or scans a biological indicator that is expired or has been discontinued or recalled. These messages may be accompanied by buttons allowing a user to cancel the biological indicator and sterilization cycle selections entirely; or to replace the expired/discontinued/recalled biological indicator with a new biological indicator (block 326). However, in embodiments where only a single type of biological indicator is supported or required, the warning messages of described above could be consolidated to only require a single biological indicator type.

If, after any of the above described warning and error messages, a user selects to continue or bypass the warning, sterilization cabinet (10) will count the biological indicator as having been verified (block 324) despite the warning; and the sterilization cycle selection and biological indicator identification will be complete (block 328). If, after a warning or error, a user chooses to replace (block 326) the previously selected biological indicator with another biological indicator, that newly selected biological indicator may be verified (block 324). If there are no warnings or errors based on the newly selected biological indicator, the sterilization cycle selection and biological indicator identification is complete (block 328).

If no biological indicator is scanned (block 308) prior to a manual selection (block 304) of a sterilization cycle, sterilization cabinet (100) will determine if there is a hard requirement (block 310) or soft requirement (block 314) for using a biological indicator. Determination of whether there is a hard requirement (block 310) or soft requirement (block 314) may depend upon a variety of configurable factors that may vary depending upon a particular hospital where system (10) is used, a particular geographical region in which system (10) is used, a user's insurance carrier requirements, and/or various other factors.

For example, in some versions there may be a hard requirement (block 310) that requires that a biological indicator be used in certain circumstances in order to comply with a rule, law, or other regulation. If such a hard requirement applies to the current sterilization cycle that is being configured (block 310), the hard indicator requirements may be displayed (block 312) since a user has not yet scanned or selected a biological indicator (308). Other exemplary interfaces may be displayed when a hard requirement applies (block 310) to the selected sterilization cycle. An exemplary interface may have a hard requirement description that indicates to the user the circumstances of the particular hard requirement that applies (block 310); and a biological indicator guide shows a graphical representation of the biological indicator that is required to continue. Such an interface may be accompanied by a button that allows a user to cancel the selection process entirely. However, the interface may not have a button that would allow the user to bypass the requirement or continue in the absence of an appropriate biological indicator.

Another interface may be similar to that described above, but which requires a "type B" biological indicator in order to continue the process. The hard requirement warning screens described above may show additional information, such as a contact number or information for individuals that can provide support, such as technical support personnel for sterilizing cabinet (100), the biological indicator, the hospital where sterilizing cabinet (100) is located, and/or other individuals that might be able to provide assistance when a user unexpectedly receives a hard requirement (block 310). However, in embodiments that only support or require a single biological indicator type, only a single interface requiring a single biological indicator may be implemented.

While the particular hard requirement description discussed previously may be a "once per 24 hours" requirement, other requirements may exist. For example, in some versions there may be a hard requirement to use a biological indicator for every cycle, every other cycle, every X number of cycles, a certain number of times per day, a certain number of times per period of hours, and/or other scenarios as may be configured.

While a hard requirement is intentionally designed to appear as being impassable without the selection of an appropriate biological indicator, some versions of system (10) may also be configured to display a set of hard requirement bypass screens to allow users to bypass (block 320) even a hard requirement in case of emergency or other substantial need. An exemplary interface may be configured to receive a pass code, supplied by support personnel or hospital administrators that will allow the hard requirement to be bypassed. An exemplary interface may be displayed to indicate to a user that the pass code was accepted, and may disable hard requirements during sterilization cycle configuration for a certain number of sterilization cycles; or for a certain period of time.

Referring back to FIG. 3, if the hard bypass is successful (block 320), the sterilization cycle selection and biological indicator identification is complete (block 328). Bypassing a hard requirement may result in additional alerts or notifications being sent to hospital administrators or other responsible individuals, and may transmit additional information to server (106) indicating the particular circumstances of the hard bypass (block 320) so that the event can be examined at a later time. A code bypass is one example of a hard requirement bypass (block 320), but other embodiments exist. For example, hard requirement bypass (block 320) may also be accomplished by scanning of an optical barcode, RFID tag, or other indicator that may be held by a small group of individuals within a hospital; or scanning of a dummy indicator that allows for a single bypass or limited number of bypasses.

Figure 11:
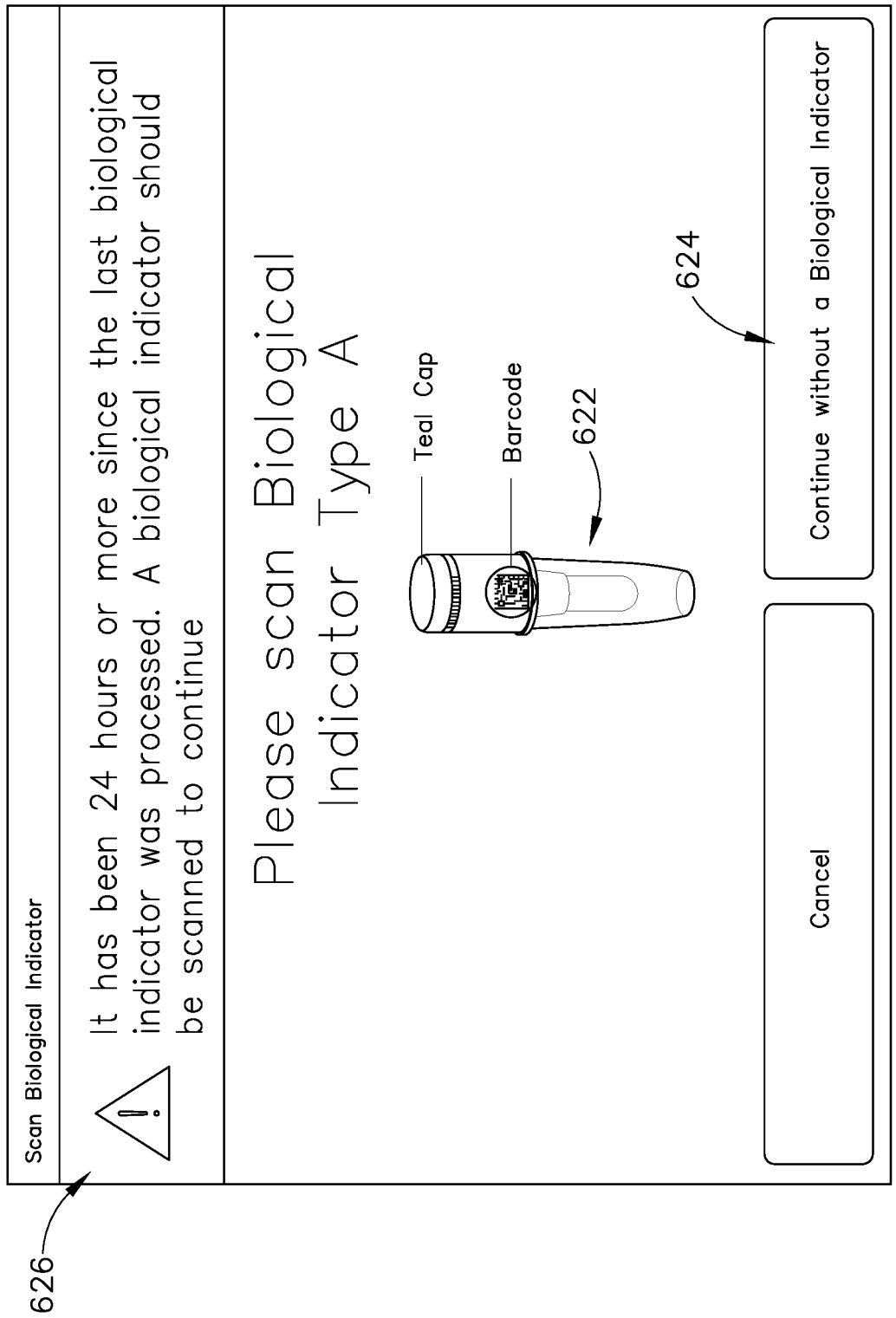
FIG. 11 depicts a screenshot of an exemplary user interface that could be presented via the sterilizing cabinet of the system of FIG. 1, to present a user with a soft requirement for selecting a biological indicator for use with a selected sterilization cycle.

If there is no hard requirement (block 310), sterilization cabinet (100) will determine if there is a soft requirement (block 314). A soft requirement may conditionally apply in similar circumstances as the hard requirement, such as for every sterilization cycle, intermittent sterilization cycles, intermittent time periods, or other scenarios. If a soft requirement exists (block 314), the soft biological indicator requirement may be displayed (block 316) via a screen such as that shown in FIG. 11. FIG. 11 shows a soft requirement description (626), a biological indicator visual guide (622), and a soft bypass (624) button. The soft requirement description (626) indicates that it has been 24 hours or more since the last biological indicator was processed, such that a new biological indicator should be scanned to continue. A user may cancel the cycle, or may choose the soft bypass (624) button if they do not wish to select a biological indicator. If the soft bypass is selected block (318), the sterilization cycle selection and indicator identification is complete (block 328). Additionally, if there is no hard requirement (block 310) and no soft requirement (block 314), the user may proceed with no biological indicator and no need for bypass; and the sterilization cycle selection and biological indicator identification is complete (block 328).

If no biological indicator is scanned prior manual selection of the sterilization cycle (block 304), and a hard or soft requirement exists (block 310, block 314) and is not bypassed (block 318, block 320), the user must scan a biological indicator (block 308) before sterilization cabinet (100) will proceed. Once a biological indicator is scanned (block 308), biological indicator verification (block 324) will proceed as previously described. In the event that either a soft or hard bypass is used (block 318, block 320), an additional warning may be displayed to notify the user of the requirement for using a biological indicator.

C. Exemplary Medical Device Placement and Load Conditioning Process

Figure 4:
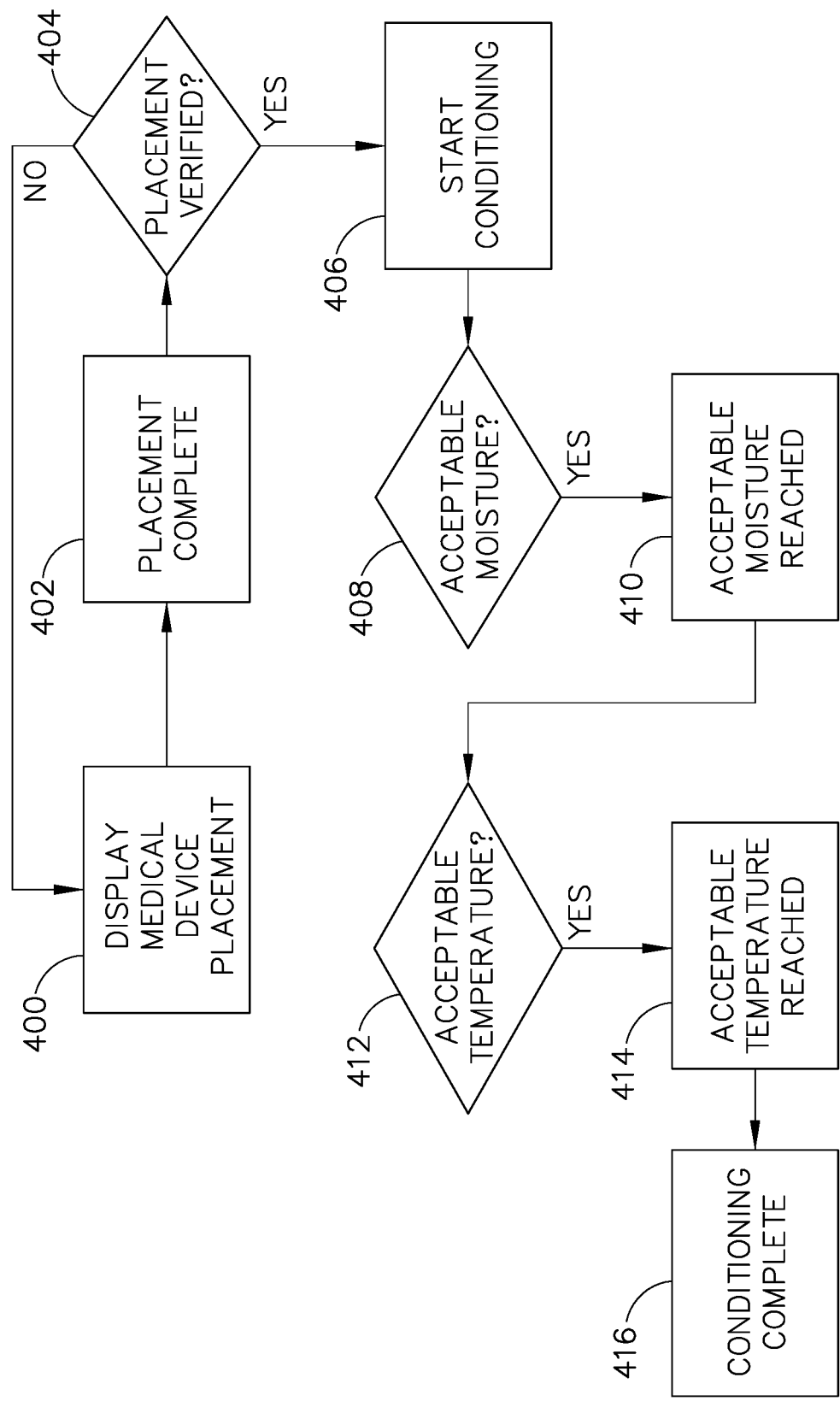
FIG. 4 depicts a flowchart of an exemplary set of steps that the sterilizing cabinet of the system of FIG. 1 could perform to prepare medical devices for a sterilization cycle.

FIG. 4 depicts an exemplary set of steps that sterilizing cabinet (100) could perform to guide a user through placement of medical devices in the sterilizing chamber of sterilizing cabinet (100) and prepare the medical devices for a sterilization cycle. It should be understood that the method shown in FIG. 4 may be viewed as showing several sub-steps that may be performed as part of the sterilization cycle preparation step (block 204) and the load conditioning step (block 206) of FIG. 2.

Figure 12:
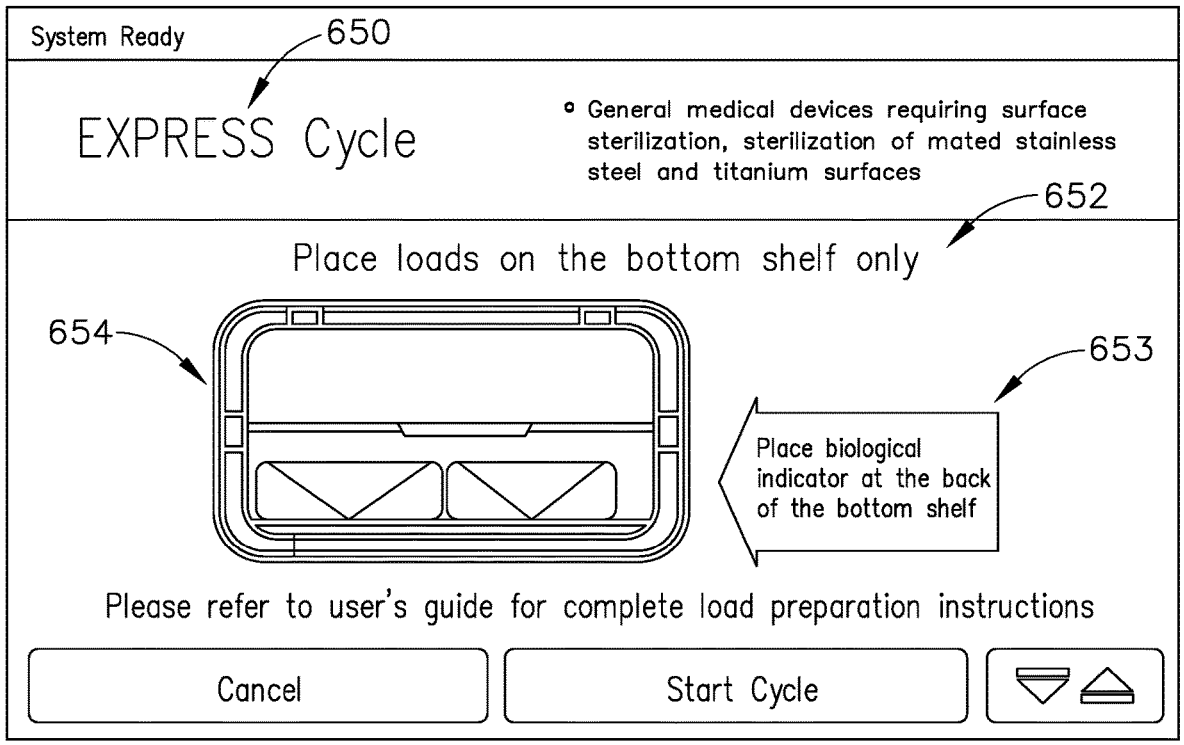
FIG. 12 depicts a screenshot of an exemplary user interface that could be presented via the sterilizing cabinet of the system of FIG. 1, to guide a user through placement and configuration of medical devices for an "express" sterilization cycle.
Figure 13:
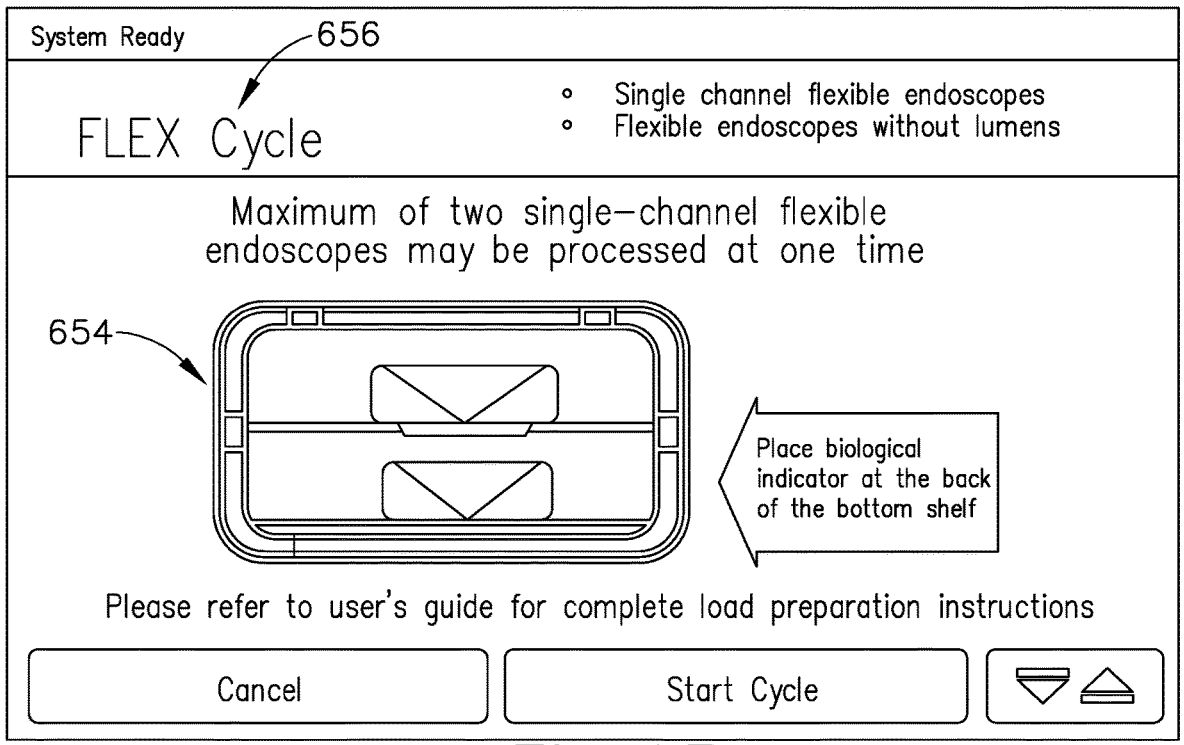
FIG. 13 depicts a screenshot of an exemplary user interface that could be presented via the sterilizing cabinet of the system of FIG. 1, to guide a user through placement and configuration of medical devices for a "flex" sterilization cycle.
Figure 14:
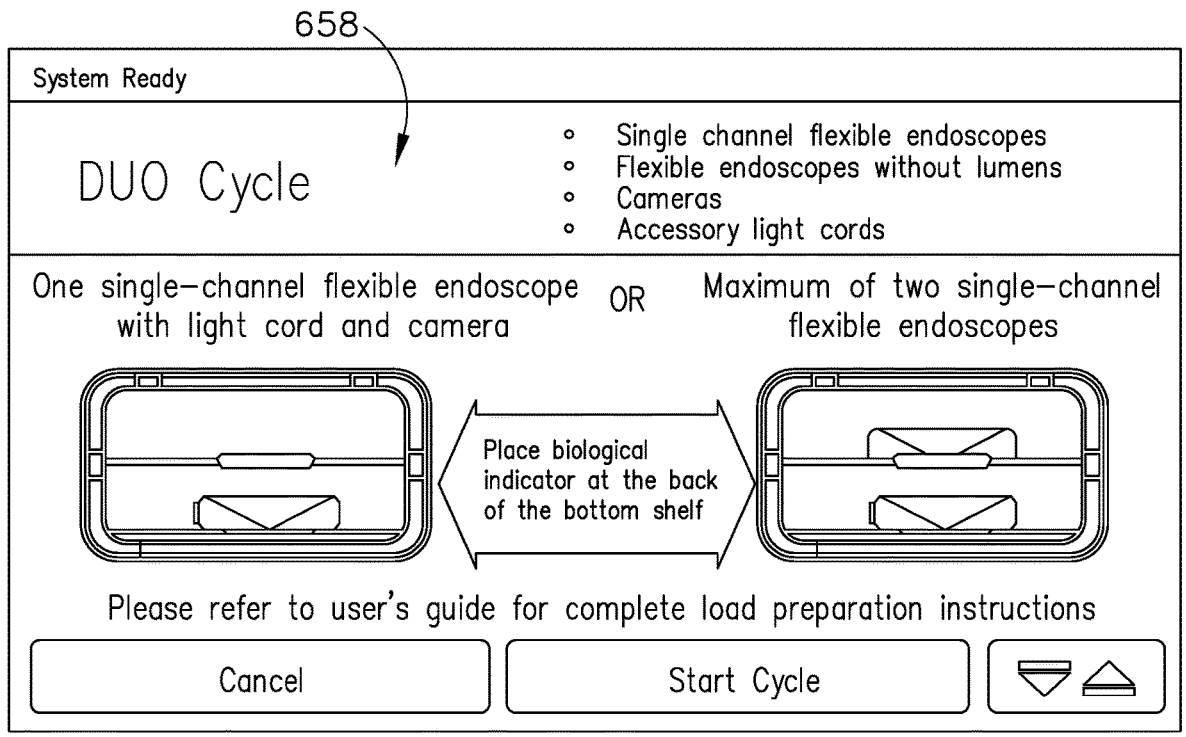
FIG. 14 depicts a screenshot of an exemplary user interface that could be presented via the sterilizing cabinet of the system of FIG. 1, to guide a user through placement and configuration of medical devices for a "duo" sterilization cycle.
Figure 15:
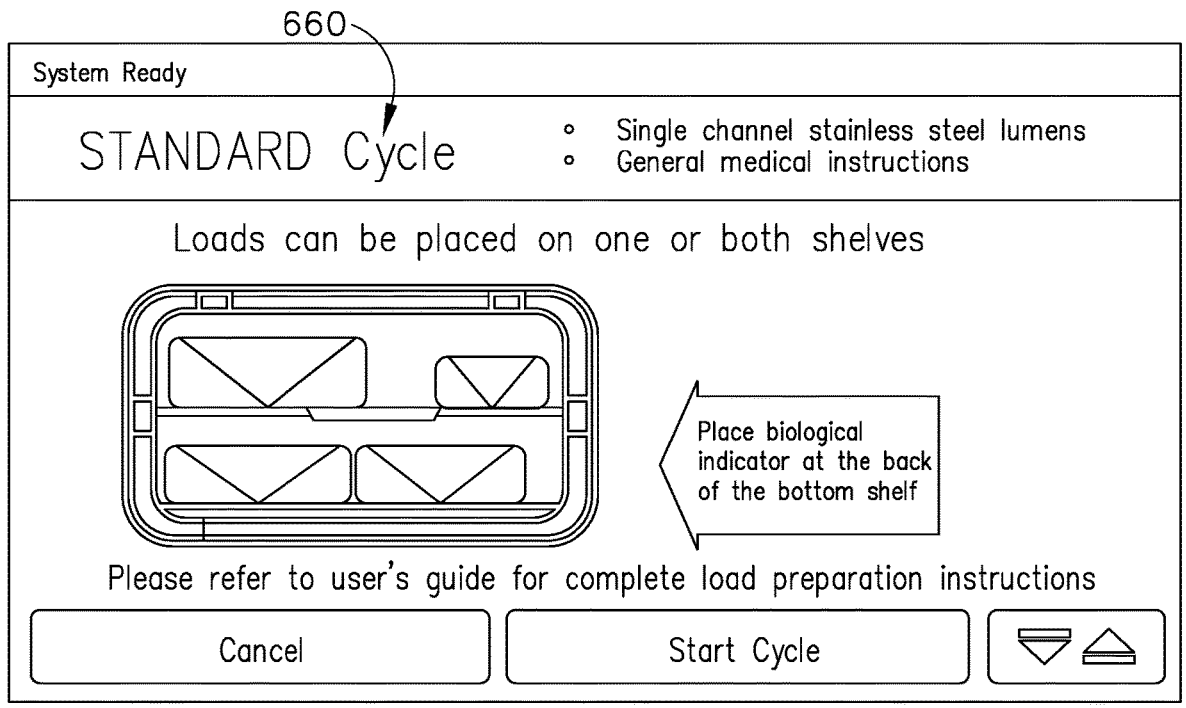
FIG. 15 depicts a screenshot of an exemplary user interface that could be presented via the sterilizing cabinet of the system of FIG. 1, to guide a user through placement and configuration of medical devices for a "standard" sterilization cycle.

Once the sterilization cycle has been selected (block 200) and the biological indicator has been identified (block 202), sterilizing cabinet (100) may display (block 400) a medical device placement that serves as a visual guide to a user's placement of medical devices within the sterilizing chamber of sterilizing cabinet (100), based on the selected sterilization cycle (block 200). FIGS. 12-15 show examples of screens that may be used to display (block 400) medical device placement. FIG. 12 shows an interface having a cycle description (650) that may describe one or more characteristics of the medical sterilization devices sterilized by the sterilization cycle, materials sterilized by the sterilization cycle, or processes used during the sterilization cycle. The interface may also have one or more placement instructions (652) that provide the user with instructions on where to place medical instruments that are to be sterilized (e.g., in relation to a shelf in the sterilization chamber), as well as where to place the biological indicator (653), if applicable to the selected sterilization cycle. The interface may also have a graphical indication (654) of placement of medical devices that may have a shape or appearance that is visually similar to a sterilization chamber of sterilizing cabinet (100). FIG. 13 shows a similar interface that provides a visual placement guide for a "flex" cycle (656), while FIG. 14 shows a similar interface for a "duo" cycle (658), and FIG. 15 shows a similar interface for a "standard" cycle (660).

Referring back to FIG. 4, once medical device placement is complete (block 402), the user may press a start button or other button indicating that medical device placement is complete and sterilizing cabinet (100) may verify medical device placement (block 404). Placement verification may occur in varying ways depending upon a particular embodiment. In some versions, placement verification may simply be a final display and confirmation of the visual placement guide (654). In other versions, placement verification may be by way of imaging devices or photo sensors, weight sensors, two-dimensional or three-dimensional camera image capture and comparison, or similar types of sensors that may detect the physical presence of an object within a defined space by way of recognizing one or more physical characteristics of its presence. Placement verification (block 404) could also be accomplished by way of a wireless RFID or NFC scanner and placement of an RFID or NFC chip on medical devices, either at the time of manufacture, the time of use, or sterilization. One or more wireless scanners could be placed in walls of sterilizing cabinet (100) and could be configured to, at the time of verification (block 404), identify the locations of medical devices within the sterilization chamber and verify that they are within a configured distance of the scanner. Versions having a wireless scanner could further be configured to identify placement of medical devices as well as types of medical devices, which could be used as an additional confirmation that the proper sterilization cycle is selected for the types of medical devices placed in the sterilization chamber.

If medical device placement cannot be verified (block 404), the cycle placement guide may be displayed again (block 400). If medical device placement is verified (block 404), sterilizing cabinet (100) may start a load conditioning process (block 406). The load conditioning process (406) prepares the sterilization chamber and the medical devices within the sterilization chamber for optimal sterilization during a sterilization cycle. Conditioning may include controlling and optimizing one or more characteristics of the sterilization chamber. For example, during load conditioning, sterilizing cabinet (100) may continuously monitor the level of moisture (block 408) within the sterilization chamber while reducing the level of moisture by, for example, circulating and dehumidifying the air of the sterilization chamber, creating a vacuum within the sterilization chamber, heating the sterilization chamber, and/or other methods for dehumidifying a sealed chamber. This may continue until sterilizing cabinet (100) determines that an acceptable level of moisture has been reached (block 410).

Sterilizing cabinet (100) may also continuously detect the temperature (block 412) within the sterilization chamber while heating the sterilization chamber by, for example, convection of heated air, conduction through an interior surface of the sterilization chamber, and/or using other techniques. This may continue until sterilizing cabinet (100) determines that an acceptable internal temperature has been reached (block 414). Various conditioning actions such as controlling temperature or humidity may be performed in parallel or in sequence. While the one or more conditioning actions are being performed, sterilizing cabinet (100) may display an interface indicating to a user the duration of time before the sterilization cycle performance may begin. Once all load conditioning criteria have been successfully met, load conditioning is complete (block 416) and the sterilization cycle may then be performed (block 208). It should therefore be understood that sterilizing cabinet (100) is configured such that the sterilization cycle (block 208) is not actually initiated until after the load conditioning process (block 206) is complete.

Load conditioning (block 206) may not always be possible, due to system error, abnormally high moisture levels, or abnormally low temperatures. An exemplary interface may be displayed when attempts to reduce moisture fail or other general errors occur during load conditioning. The interface provides additional guidance to a user so that further attempts to conditioning may be made. Another exemplary interface may be displayed when sterilization chamber temperatures are not able to be raised to an acceptable range; and indicates to a user the reason for the failure.

As noted above, sterilization cabinet (100) may begin performing the sterilization cycle (block 208) automatically and immediately after load conditioning (block 206) has been completed. During performance of the sterilization cycle (block 208), an interface may be displayed that shows a duration remaining for cycle, an overall cycle completion, and a current cycle stage, which describes what part of the sterilization cycle is currently being performed (e.g. plasma, vacuum, injection, heat, chemical treatment), in addition to buttons for canceling the sterilization cycle and viewing further information on the sterilization cycle. It should be understood that a screen like the one described above may automatically replace other interfaces after load conditioning (block 206) has been completed.

D. Exemplary Reporting of Sterilization Cycle Results

Figure 5:
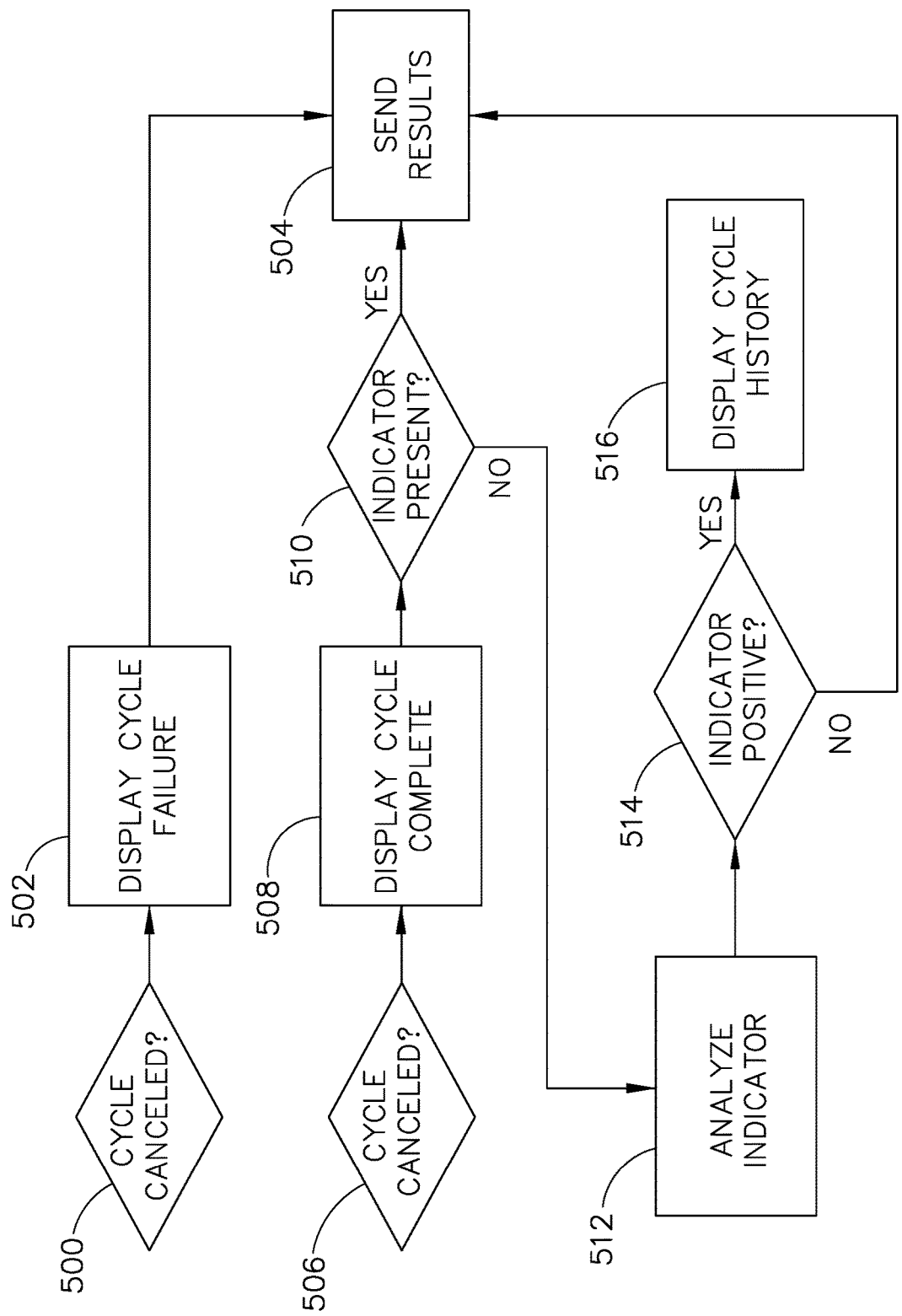
FIG. 5 depicts a flowchart of an exemplary set of steps that the sterilizing cabinet of the system of FIG. 1 could perform to complete and report results for a sterilization cycle.

FIG. 5 depicts an exemplary set of steps that sterilizing cabinet (100) could perform to complete and report results of a sterilization cycle upon completion of the cycle (block 208). In other words, the method shown in FIG. 5 may be viewed as showing several sub-steps that may be performed as part of the provision of results step (block 210) of FIG. 2. If the sterilization cycle was canceled or unable to complete due to error or by a user action (block 500), sterilizing cabinet (100) may remain sealed and may also display (block 502) an interface that shows a sterilization cycle cancellation message as well as various details relating to the sterilization cycle, such as date, time, configuration, elapsed time, sterilization cycle operator, the stage at which the sterilization cycle failed, and other information that may be used to identify why the sterilization cycle failed. Such displayed information and other information relating to the sterilization cycle may also be sent (block 504) to the server (106) or to a printer, or both, for further use or analysis.

If the sterilization cycle completes (block 506), sterilization cabinet (100) may display a sterilization cycle complete (block 508) interface such as that shown in FIG. 16, which may include information such as sterilization cycle identifier, sterilization cycle type, start time, duration, operator, and other information (666). If a biological indicator is not present (block 510) during the sterilization cycle, the displayed information and other information associated with the sterilization cycle may be sent (block 504) to the server (106) or to a printer, or both, for further use or analysis. If a biological indicator was selected and used (block 510) during the sterilization cycle, the biological indicator may be removed by the user and placed in biological indicator analyzer (102) to determine the efficacy of the sterilization treatment (block 512), as described in greater detail below. If data provided by biological indicator analyzer (102) indicates that the biological indicator tests negative for contamination (block 514), the results of the sterilization cycle as well as the results of the indicator analysis (block 512) are sent (block 504) to server (106) or a printer, or both. If data provided by biological indicator analyzer (102) suggests that the biological indicator tests positive for contamination (block 514), sterilization cabinet (100) may display the sterilization cycle history (block 516) for sterilization cycles occurring before the immediate sterilization cycle so that a user may determine if any prior performed sterilization cycles may need to be re-run to ensure the sterility of the medical devices involved. If subsequent sterilization cycles were performed after the above-described sterilization cycle and before the biological indicator analysis (block 512) is complete, those subsequent sterilization cycles may also need to be re-run.

FIG. 17 shows an example of an interface for displaying sterilization cycle history of potentially affected sterilization cycles to a user in the event of a positive biological indicator result (block 514). The example interface of FIG. 17 shows the biological indicator result (668); a biological indicator identifier (670), which relates a unique biological indicator to the sterilization cycle for which it was selected or scanned, a time at which the biological indicator was analyzed (672); as well as a previous sterilization cycle window, which shows a sequential listing of the previously performed sterilization cycles (674) that may be affected, which goes back at least as far as the previously performed sterilization cycle which included a biological indicator; a sterilization cycle completion time for each affected sterilization cycle (676); a sterilization cycle type for each affected sterilization cycle (678); and a biological indicator result for each affected sterilization cycle (680). The interface of FIG. 17 could be used by a user to identify a set of affected sterilization cycles, which in some cases will be each sterilization cycle that was performed (i) prior to the sterilization cycle that generated a positive indication of contamination and (ii) subsequent to the most recent sterilization cycle that generated a negative indication of contamination. This set of affected sterilization cycles provides a narrow listing of each sterilization cycle that may not have been fully effective as a result of a change in performance of sterilizing cabinet (100) or other error or contamination that also may have caused the current positive indication of contamination. Medical devices that were believed to be sterilized during the affected sterilization cycles may be reexamined and/or re-sterilized in order to ensure safe use.

III. Exemplary Sterilizing Cabinet

Figure 18:
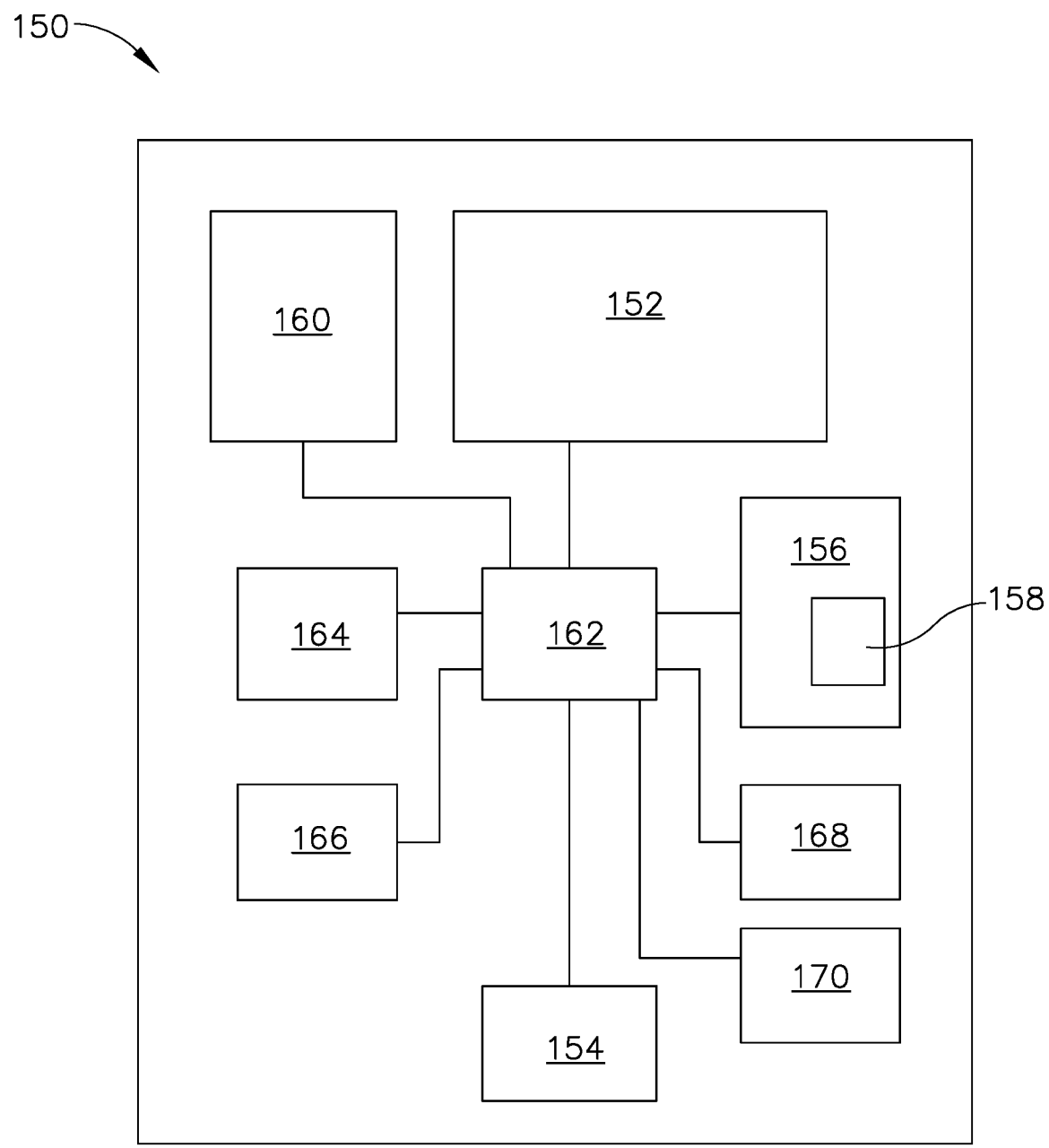
FIG. 18 depicts a schematic view of an exemplary sterilizing cabinet that may be used with the system of FIG. 1.

FIG. 18 depicts an exemplary set of components that may be incorporated into sterilizing cabinet (100) of system (10). In particular, FIG. 18 shows an exemplary sterilizing cabinet (150) that is operable to perform the various methods described above and shown in FIGS. 2-5. Sterilizing cabinet (150) of the present example includes a sterilization chamber (152), which is configured to receive one or more medical devices for sterilization. While not shown, sterilizing cabinet (150) also includes a door that opens and closes sterilization chamber (152) in response to actuation of a kick plate (154). An operator may thereby open and close sterilization chamber (152) in a hands-free fashion. Sterilizing cabinet (100) also includes a sterilization module (156) that is operable to dispense a sterilant into sterilization chamber (152) in order to sterilize medical devices contained in sterilization chamber (152) as described above. In the present example, sterilization module (156) is configured to receive replaceable sterilant cartridges (158) containing a certain amount of sterilant. By way of example only, each sterilant cartridge (158) may contain enough sterilant to perform five sterilization procedures.

Sterilizing cabinet (150) of the present example further includes a touch screen display (160). Touch screen display (160) is operable to render the various user interface display screens described above and shown in FIGS. 6-17. Of course, touch screen display (160) may display various other screens as well. Touch screen display (160) is further configured to receive user input in the form of the user contacting touch screen display (160) in accordance with conventional touch screen technology. In addition or in the alternative, sterilizing cabinet (150) may include various other kinds of user input features, including but not limited to buttons, keypads, keyboards, a mouse, a trackball, etc.

Sterilizing cabinet (150) of the present example further includes a processor (162), which is in communication with sterilization module (156) and with touch screen display (160). Processor (162) is operable to execute control algorithms to drive sterilization module (156) in accordance with user input. Processor (162) is further operable to execute instructions to display the various screens on touch screen display (160); and to process instructions received from a user via touch screen display (160) (and/or via other user input features). As will be described in greater detail below and as shown in FIG. 18, processor (162) is also in communication with various other components of sterilization cabinet (150) and is thereby operable to drive those components and/or process input and/or other data from those components. Various suitable components and configurations that may be used to form processor (162) will be apparent to those of ordinary skill in the art in view of the teachings herein.

Sterilizing cabinet (150) of the present example further includes a communication module (164). Communication module (164) is configured to enable bidirectional communication between sterilizing cabinet (150) and communication hub (20). In addition or in the alternative, communication module (164) may be configured to enable bidirectional communication between sterilizing cabinet (150) and server (106). By way of example only, communication module (164) may be configured to provide wired and/or wireless communication via as Ethernet, Wi-Fi, Bluetooth, USB, infrared, NFC, and/or other technologies. Various suitable components and configurations that may be used to form communication module (164) will be apparent to those of ordinary skill in the art in view of the teachings herein. Communications that are sent from or received through communication module (164) are processed through processor (162).

Sterilizing cabinet (150) of the present example further includes a reader (166), which is operable to read an identification tag of a biological indicator as described herein. It should be understood that reader (166) may be used to perform the steps of indicator scanning (block 302, block 308) described above with reference to FIG. 3. By way of example only, reader (166) may comprise an optical reader that is operable to read an optical identification tag (e.g., barcode, QR code, etc.) of a biological indicator. In addition or in the alternative, reader (166) may comprise RFID reader that is operable to read an RFID identification tag (e.g., barcode, QR code, etc.) of a biological indicator. Various suitable components and configurations that may be used to form reader (166) will be apparent to those of ordinary skill in the art in view of the teachings herein. Data received through reader (166) is processed through processor (162).

Sterilizing cabinet (150) of the present example further includes a memory (168), which is operable to store control logic and instructions and that are executed by processor (162) to drive components such as sterilization module (156), touch screen display (160), communication module (164), and reader (166). Memory (168) may also be used to store results associated with setup of a sterilization cycle, performance of a load conditioning cycle, performance of a sterilization cycle, and/or various other kinds of information. Various suitable forms that memory (168) may take, as well as various ways in which memory (168) may be used, will be apparent to those of ordinary skill in the art in view of the teachings herein.

Sterilizing cabinet (150) of the present example further includes a printer (170), which is operable to print information such as results associated with setup of a sterilization cycle, performance of a load conditioning cycle, performance of a sterilization cycle, and/or various other kinds of information. By way of example only, printer (170) may comprise a thermal printer, though of course any other suitable kind of printer may be used. Various suitable forms that printer (170) may take, as well as various ways in which printer (170) may be used, will be apparent to those of ordinary skill in the art in view of the teachings herein. It should also be understood that printer (170) is merely optional and may be omitted in some versions.

In addition to the foregoing, sterilizing cabinet (150) may be configured and operable in accordance with at least some of the teachings of U.S. Pat. No. 6,939,519, the disclosure of which is incorporated by reference herein; U.S. Pat. No. 6,852,279, the disclosure of which is incorporated by reference herein; U.S. Pat. No. 6,852,277, the disclosure of which is incorporated by reference herein; and/or U.S. Pat. No. 6,447,719, the disclosure of which is incorporated by reference herein.

IV. Exemplary Biological Indicator Assembly

Figure 19:
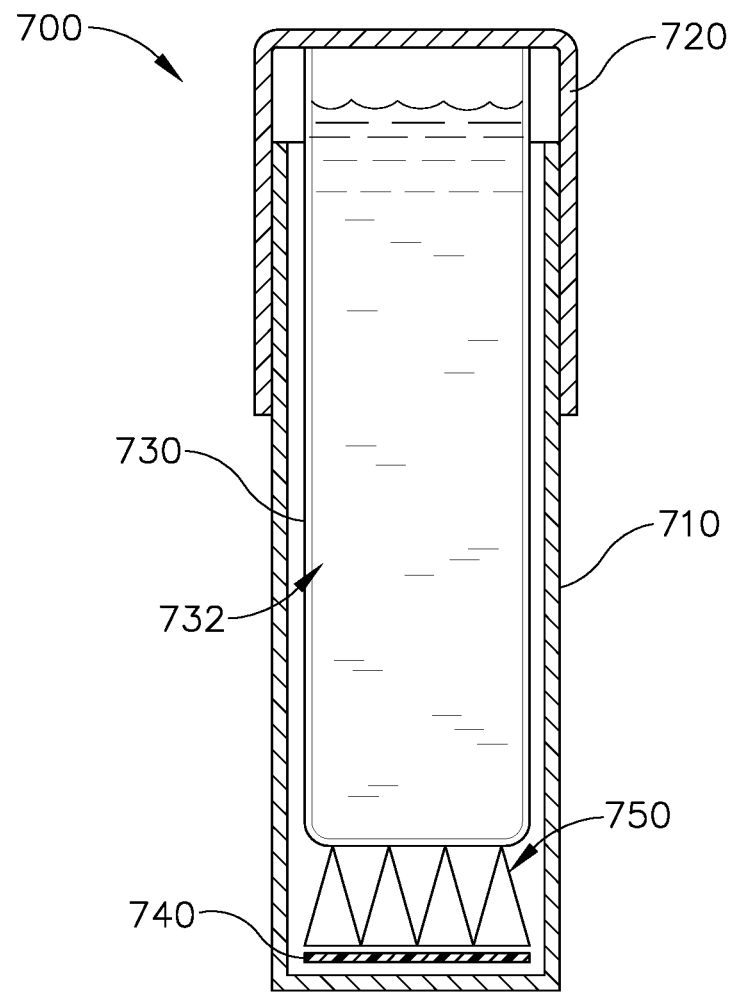
FIG. 19 depicts a schematic view of an exemplary biological indicator assembly that may be used with the system of FIG. 1.

As noted above, a biological indicator may be included in sterilizing cabinet (100, 150) along with the medical device during the sterilization process (block 208) in order to ensure that the sterilization process (block 208) was successful. FIG. 19 shows an exemplary form that such a biological indicator may take. In particular, FIG. 19 shows a biological indicator (700) that includes a housing (710), a cap (720), an ampoule (730), and a carrier (740). Housing (710) is formed of a transparent material (e.g., clear plastic, glass, etc.) and is hollow such that housing (710) insertably receives ampoule (730). Ampoule (730) is also formed of a transparent material (e.g., clear plastic, glass, etc.) and contains a fluid (732). By way of example only, fluid (732) may comprise a liquid growth medium. Such a liquid growth medium is capable of, with incubation, promoting growth of any viable microorganisms it contacts. Fluid (732) also includes a fluorophore whose fluorescence depends on the amount of microorganisms contained in the medium. Fluid (732) is sealed within ampoule (730).

Carrier (740) provides a source of microorganisms or active enzymes. By way of example only, carrier (740) may be impregnated with bacterial spores, other forms of bacteria (e.g., vegetative), and/or active enzymes. By way of example only, spores from *Bacillus, Geobacillus*, and *Clostridium* species may be used. Carrier (740) may be water-absorbent and may be formed of filter paper. Sheet-like materials such as cloth, nonwoven polypropylene, rayon or nylon, and microporous polymeric materials may also be used to form carrier (740). Non-water absorbent materials may also be used to form carrier (740), such as metals (e.g., aluminum or stainless steel), glass (e.g., glass beads or glass fibers), porcelain, or plastic. Of course, combinations of the foregoing materials may also be used to form carrier (740).

Ampoule (730) is configured as a frangible component of biological indicator (700), such that ampoule (730) may be fractured within housing to release fluid (732) in housing (710). To assist in the fracture of ampoule (730), a set of fracturing features (750) are disposed in the bottom of housing (710). While fracturing features (750) are shown as spikes in FIG. 19, it should be understood that this is merely illustrative. Fracturing features (750) may take any other suitable form. To further assist in the fracture of ampoule (730), cap (720) is configured to slide downwardly along housing (710) to press ampoule (730) against fracturing features (750). This may be done right before biological indicator (700) is inserted into indicator analyzer (102, 800) as described in greater detail below. It should be understood that ampoule (730) would remain intact while biological indicator (700) is in sterilizing cabinet (100) during a sterilization process. Cap (720) may include one or more openings that allow gasses (e.g., air or sterilant, etc.) to pass into housing (710) before cap (720) is pressed downwardly relative to housing (710) to fracture ampoule (730). These openings may thus enable the microorganisms on carrier (740) to be destroyed by the sterilization process (block 208). However, after cap (720) is pressed downwardly relative to housing (710) to fracture ampoule (730), these one or more openings may be sealed to contain the released fluid (732) in housing (710). When fluid (732) is released from ampoule (730), the released fluid eventually reaches carrier (740), thereby initiating an incubation process with any living microorganisms remaining on carrier (740), as will be described in greater detail below.

While not shown in FIG. 19, housing (710) may also include an identification tag. Such an identification tag may include a machine readable feature that is capable of being read by reader (166) of sterilizing cabinet (100, 150) and biological indicator analyzer (102). In other words, the identification tag may be read perform to the steps of indicator scanning (block 302, block 308) described above with reference to FIG. 3. By way of example only, the identification tag may comprise an optical code (e.g., a barcode, a QR code, etc.), an RFID tag, and/or any other suitable kind of machine readable identifier. In addition, the identification tag may include human readable features such as text, numbers, color coding, etc.

Cap (720) may also include a color changing feature. Such a color changing feature may serve as a chemical indicator that changes color when biological indicator (700) is exposed to the sterilant of sterilizing cabinet (100, 150). In some versions, the color changing feature simply changes between two distinctive colors, with one of the colors indicating no exposure to a sterilant and the other color indicating at least some exposure to a sterilant. In some other versions, the color changing feature changes along a range of colors based on the extent to which biological indicator (700) has been exposed to a sterilant. In other words, the color change may be proportional to the degree of sterilant exposure.

In addition to or in lieu of the foregoing, biological indicator (700) may be configured and operable in accordance with at least some of the teachings of U.S. patent application Ser. No. 15/057,768, entitled "Self-Contained Biological Indicator," filed Mar. 1, 2016, the disclosure of which is incorporated by reference herein. Other suitable forms that biological indicator (700) may take will be apparent to those of ordinary skill in the art in view of the teachings herein.

V. Exemplary Biological Indicator Analyzer

A. Exemplary Biological Indicator Analyzer Hardware

Figure 20:
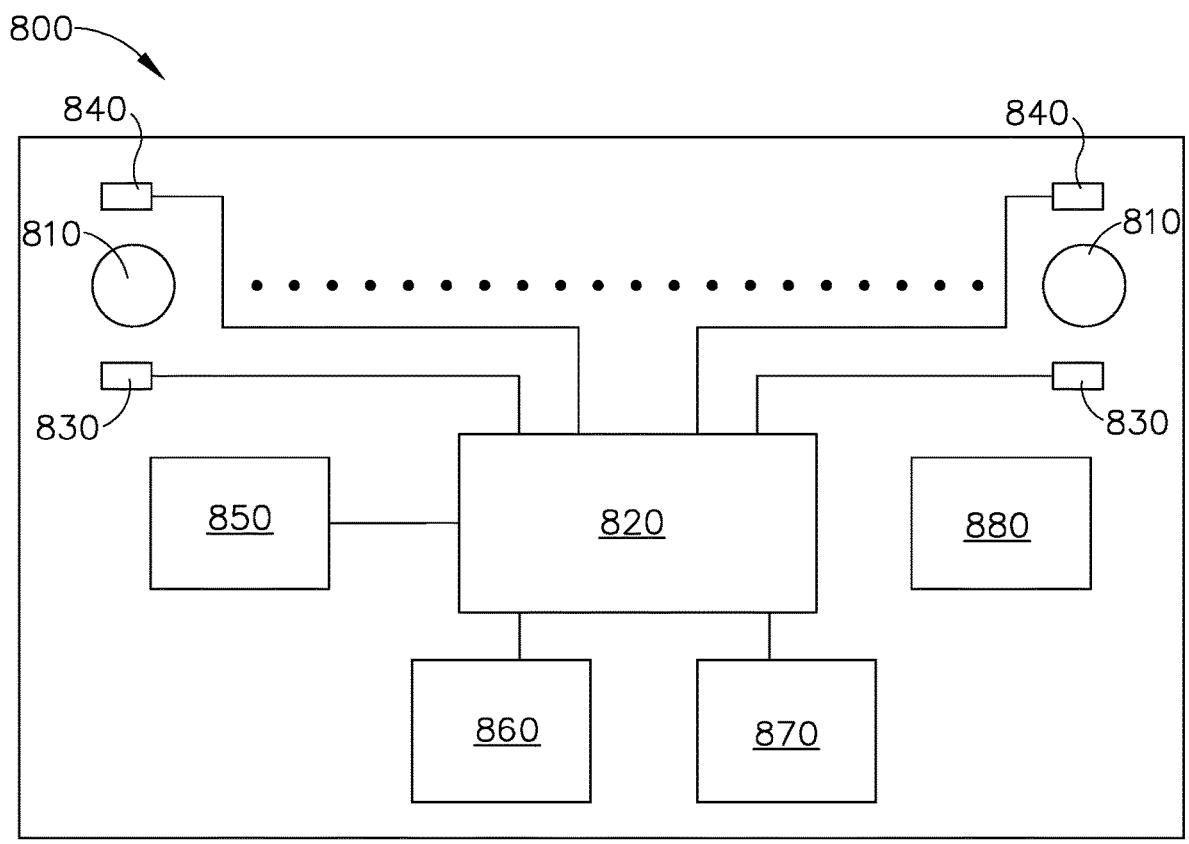
FIG. 20 depicts a schematic view of an exemplary indicator analyzer that may be used to process the biological indicator assembly of FIG. 19 as part of the system of FIG. 1.

FIG. 20 depicts an exemplary set of components that may be incorporated into biological indicator analyzer (102). In particular, FIG. 20 shows an exemplary biological indicator analyzer (800) that is operable to perform the biological indicator analysis (block 512) described above with reference to FIG. 5. Biological indicator analyzer (800) of this example comprises a plurality of wells (810), each of which is configured to insertingly receive a respective biological indicator (700). While two wells (810) are shown, it should be understood that any other suitable number of wells (810) may be provided, including eight wells (810), less than eight wells (810), or more than eight wells (810). Biological indicator analyzer (800) also includes a processor (820) that is operable to execute instructions and control algorithms, process information, etc.

Each well (810) has an associated light source (830) and sensor (840). Each light source (830) is configured to project light through housing (710) of the biological indicator (700) that is inserted in the corresponding well (810); and each sensor (840) is operable to detect light fluoresced by fluid (732) contained in housing (710). By way of example only, light source (830) may be in the form of a laser that is configured to emit ultraviolet light. Various other suitable forms that light source (830) may take will be apparent to those of ordinary skill in the art in view of the teachings herein. By way of further example only, sensor (840) may comprise a charge coupled device (CCD). Various other suitable forms that sensor (840) may take will be apparent to those of ordinary skill in the art in view of the teachings herein. As noted above, the fluorescence of fluid (732) will depend on the amount of living microorganisms contained in the medium of fluid (732). Thus, sensor (840) will be able to detect the presence of living microorganisms in fluid (732) based on the degree to which fluid (732) fluoresces in response to light from light source (830).

Biological indicator analyzer (800) of the present example further includes a touch screen display (850). Touch screen display (850) is operable to render various user interface display screens associated with operation of biological indicator analyzer (800). Touch screen display (850) is further configured to receive user input in the form of the user contacting touch screen display (850) in accordance with conventional touch screen technology. In addition or in the alternative, biological indicator analyzer (800) may include various other kinds of user input features, including but not limited to buttons, keypads, keyboards, a mouse, a trackball, etc. Displays provided through touch screen display (850) may be driven by processor (820). User inputs received through touch screen display (850) may be processed by processor (820).

Biological indicator analyzer (800) of the present example further includes a communication module (860). Communication module (860) is configured to enable bidirectional communication between biological indicator analyzer (800) and communication hub (20). In addition or in the alternative, communication module may be configured to enable bidirectional communication between biological indicator analyzer (800) and server (106). By way of example only, communication module (860) may be configured to provide wired and/or wireless communication via as Ethernet, Wi-Fi, Bluetooth, USB, infrared, NFC, and/or other technologies. Various suitable components and configurations that may be used to form communication module (860) will be apparent to those of ordinary skill in the art in view of the teachings herein. Communications that are sent from or received through communication module (860) are processed through processor (820).

Biological indicator analyzer (800) of the present example further includes a reader (870), which is operable to read an identification tag of biological indicator (700) as described herein. It should be understood that reader (870) may be used to identify biological indicator (700) before biological indicator (700) is analyzed (block 512). By way of example only, reader (870) may comprise an optical reader that is operable to read an optical identification tag (e.g., barcode, QR code, etc.) of a biological indicator. In addition or in the alternative, reader (870) may comprise RFID reader that is operable to read an RFID identification tag (e.g., barcode, QR code, etc.) of a biological indicator. Various suitable components and configurations that may be used to form reader (870) will be apparent to those of ordinary skill in the art in view of the teachings herein. Data received through reader (870) is processed through processor (820).

Biological indicator analyzer (800) of the present example further includes a memory (880), which is operable to store control logic and instructions and that are executed by processor (820) to drive components such as light source (830), touch screen display (850), communication module (860), and reader (870). Memory (880) may also be used to store results associated with performance of biological indicator analysis, and/or various other kinds of information. Various suitable forms that memory (880) may take, as well as various ways in which memory (880) may be used, will be apparent to those of ordinary skill in the art in view of the teachings herein.

Figure 21:
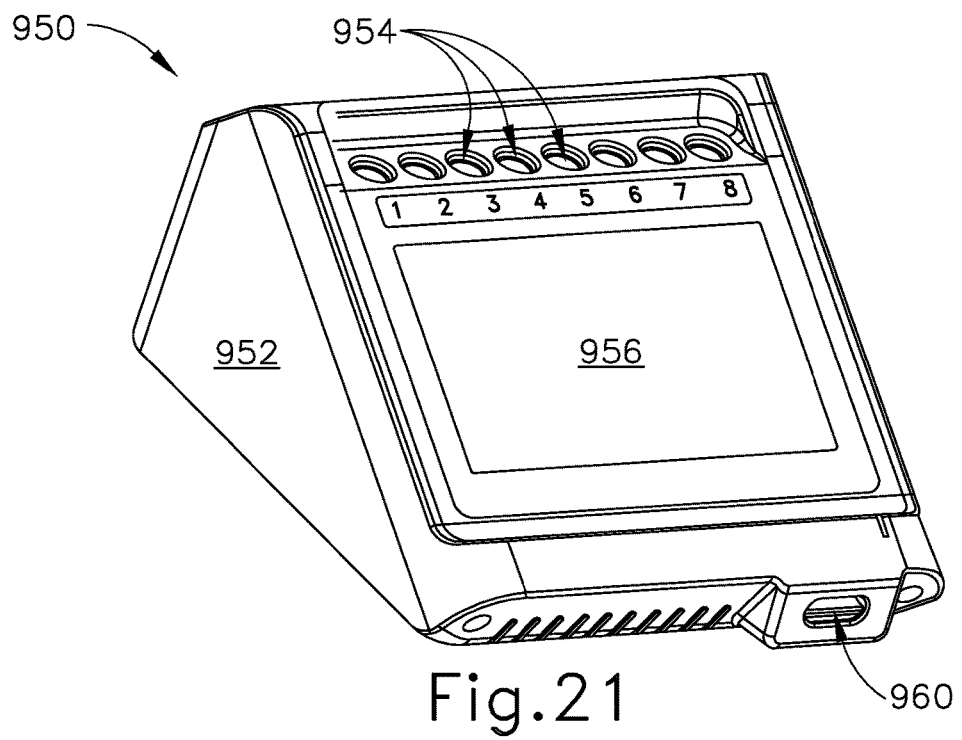
FIG. 21 depicts a perspective view of an exemplary form that the indicator analyzer of FIG. 20 may take.

FIG. 21 shows an exemplary form that indicator analyzer (800) may take. In particular, FIG. 21 shows an indicator analyzer (950) that includes a housing (952) with a set of eight wells (954), a touch screen display (956), and a reader (960). Housing (952) is configured to sit on a tabletop or other horizontal surface and present touch screen (956) at an oblique angle relative to the surface upon which housing (952) rests. Wells (954) are configured and operable like wells (810) described above. Touch screen display (956) is configured and operable like touch screen display (850) described above. Various examples of interactive screens that may be displayed via touch screen displays (850, 956) will be described in greater detail below. Reader (960) is configured and operable like reader (870) described above. It should be understood that indicator analyzer (950) may further include the other features described above with respect to indicator analyzer (800); and may further provide the same functionality and operability described above with respect to indicator analyzer (800). Other suitable forms that indicator analyzer (102, 800, 950) may take will be apparent to those of ordinary skill in the art in view of the teachings herein.

B. Exemplary Biological Indicator Processes and Interfaces

FIG. 22 shows an exemplary set of steps that may be used to initiate biological indicator (700) analysis cycle by biological indicator analyzer (102, 800, 950). As a first step, the user may observe which wells (810, 954) are vacant (block 900) and select a vacant well (block 902). In some versions, touch screen display (850, 956) presents a number next to each vacant well (810, 954), such that the operator simply touches the number associated with the selected vacant well (810, 954) in order to effect selection of that vacant well (block 902). Next, a display screen on touch screen display (850, 956) may prompt the user to place the identification tag of biological indicator (700) near reader (870, 960) to enable reader (870, 960) to read the identification tag of biological indicator (700). As part of this prompting, touch screen display (850, 956) may point to the location of reader (870, 960) to assist the user in finding reader (870, 960). The user may then use reader (870, 960) to read the identification tag of biological indicator (700) (block 904).

A display screen on touch screen display (850, 956) may then prompt the user to identify himself or herself. The user may then manipulate touch screen display (850, 956) to identify himself or herself (block 906). A display screen on touch screen display (850, 956) may then prompt the user to indicate whether the chemical indicator on cap (720) of biological indicator (700) has changed color. The user may then manipulate touch screen display (850, 956) to indicate whether the chemical indicator on cap (720) of biological indicator (700) has changed color (block 908).

A display screen on touch screen display (850, 956) may then prompt the user to prepare biological indicator (700) for loading into the selected well (810, 954) by fracturing ampoule (730) and shaking biological indicator (700). The operator may then fracture ampoule (730) by pressing on cap (720), then shake biological indicator (700) (block 910) to ensure proper mixing of fluid (732) with carrier (740). The user may then quickly place biological indicator (700) in the selected well (810, 954) (block 912). In some instances it may be desirable to insert biological indicator (700) in the selected well (810, 954) (block 912) immediately after fracturing ampoule (730) and shaking biological indicator (700) (block 910).

In some versions, indicator analyzer (102, 800, 950) is configured to determine whether the user appropriately completed the step of fracturing ampoule (730) and shaking biological indicator (700) (block 910) before inserting biological indicator (700) in the selected well (810, 954) (block 912). By way of example only, this may be determined based on how sensor (840) detects light emitted by light source (830) after biological indicator (700) is inserted in the selected well (810, 954). In the event that indicator analyzer (102, 800, 950) determines that the user failed to appropriately complete the step of fracturing ampoule (730) and shaking biological indicator (700) (block 910) before inserting biological indicator (700) in the selected well (810, 954) (block 912), touch screen display (850, 956) may prompt the user to withdraw biological indicator (700) from well (810, 954) and properly complete the step of fracturing ampoule (730) and shaking biological indicator (700) (block 910).

To the extent that the user has properly completed the step of fracturing ampoule (730) and shaking biological indicator (700) (block 910), and then inserted biological indicator (700) in the selected well (block 912), biological indicator (700) is allowed to sit in well (810, 954) for an incubation period (block 914). During the incubation period (block 914), light source (830) associated with the selected well (810, 954) is activated and sensor (840) monitors responsive fluorescence of fluid (732) in indicator (700). Well (810, 954) may also be heated (e.g., to approximately 60° C.) during the incubation period (block 914). As noted above, fluid (732) includes a fluorophore whose fluorescence depends on the amount of microorganisms contained in the medium. Thus, sensor (8400 can detect the presence of living microorganisms (from carrier (740)) in fluid (732) based on the fluorescence of fluid (732). It should therefore be understood that, after a suitable incubation period has passed, indicator analyzer (102, 800, 950) will conclude whether any of the microorganisms that were on carrier (740) (i.e., before the sterilization cycle in sterilization cabinet (100, 150)) survived the sterilization cycle in sterilization cabinet (100), based on the fluorescence of fluid (732) as sensed by sensor (840).

By way of example only, the incubation period (block 914) may be approximately 30 minutes. Alternatively, the incubation period may be substantially longer (e.g., one or more hours), shorter, or of any other suitable duration. During the incubation period (block 914), touch screen display (850, 956) may provide a graphical representation of the amount of time remaining in the incubation period. When more than one well (810, 954) is occupied by a corresponding biological indicator (700), touch screen display (850, 956) may provide a graphical representation of the amount of time remaining in the incubation period for each occupied well (810, 954).

Figure 23:
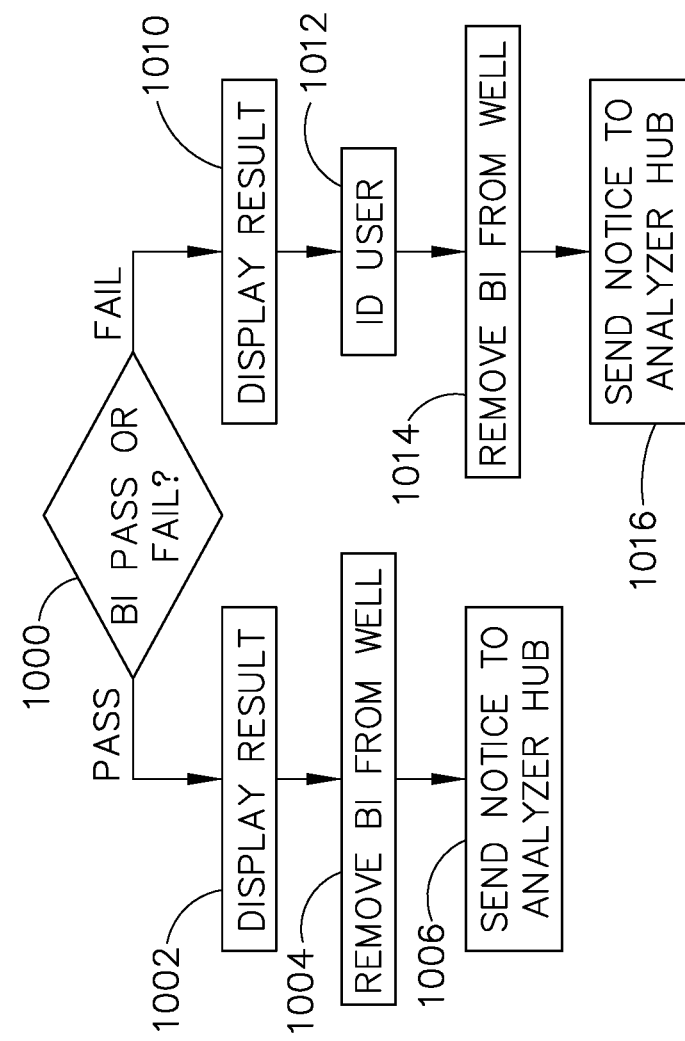
FIG. 23 depicts a flowchart of exemplary steps that may be performed by the indicator analyzer of FIG. 20 based on whether the biological indicator assembly of FIG. 19 passes or fails analysis.

FIG. 23 shows a set of exemplary steps that may be carried out once the incubation period (block 914) is complete. As noted above, biological indicator analyzer (102, 800, 950) can determine whether any of the microorganisms that were on carrier (740) (i.e., before the sterilization cycle in sterilization cabinet (100, 150)) survived the sterilization cycle in sterilization cabinet (100), based on the fluorescence of fluid (732) as sensed by sensor (840). Thus, biological indicator analyzer (102, 800, 950) can determine whether biological indicator (700) passes or fails analysis (block 1000). In this sense, a "pass" result indicates that no living microorganisms are present in biological indicator (700), which indicates that the sterilization cycle (block 208) in sterilization cabinet (100) was successful. A "fail" result indicates that living microorganisms are present in biological indicator (700), which indicates that the sterilization cycle (block 208) in sterilization cabinet (100) was unsuccessful.

In the event of a "pass" result, touch screen display (850, 956) may present a screen to the user indicating that biological indicator (700) passed the analysis (block 1002). Touch screen display (850, 956) may also prompt the user to remove biological indicator (700) from well (810, 954) (block 1004) and appropriately discard the used biological indicator (700). As described in greater detail below, biological indicator analyzer (102, 800, 950) may also transmit the "pass" result (and associated data) to communication hub (20) (block 1006) via communication module (860). In some versions, this transmission of the "pass" result (and associated data) to communication hub (20) (block 1006) is done in response to a query from communication hub (20), such that the "pass" result (and associated data) is pulled from biological indicator analyzer (102, 800, 950) by communication hub (20). In some other versions, the "pass" result (and associated data) is pushed to communication hub (20) (block 1006) by biological indicator analyzer (102, 800, 950), without requiring a query from communication hub (20).

In the event of a "fail" result, touch screen display (850, 956) may present a screen to the user indicating that biological indicator (700) failed the analysis (block 1010). Touch screen display (850, 956) may then prompt the user to identify himself or herself. The user may then manipulate touch screen display (850, 956) to identify himself or herself (block 1012). Touch screen display (850, 956) may then prompt the user to remove biological indicator (700) from well (810, 954) (block 1014) and appropriately discard the used biological indicator (700). As described in greater detail below, biological indicator analyzer (102, 800, 950) may also transmit the "fail" result (and associated data) to communication hub (20) (block 1016) via communication module (860). In some versions, this transmission of the "fail" result (and associated data) to communication hub (20) (block 1016) is done in response to a query from communication hub (20), such that the "fail" result (and associated data) is pulled from biological indicator analyzer (102, 800, 950) by communication hub (20). In some other versions, the "fail" result (and associated data) is pushed to communication hub (20) (block 1016) by biological indicator analyzer (102, 800, 950), without requiring a query from communication hub (20).

Figure 24:
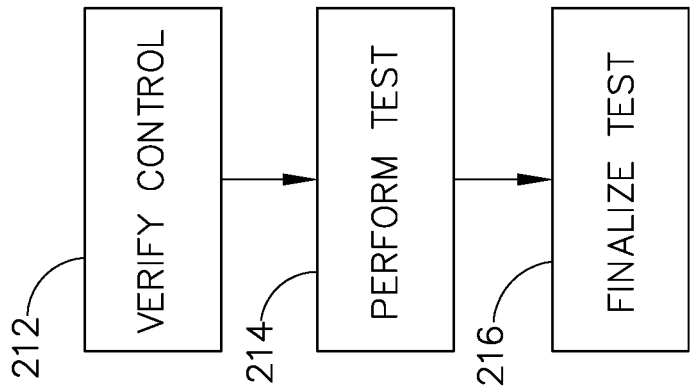
FIG. 24 depicts a high level flowchart of exemplary steps that may be performed by the indicator analyzer of FIG. 20 to provide results for a biological indicator.

FIG. 24 shows a set of exemplary high level steps that may be performed by an indicator analyzer (102, 800, 950) to employ the use of an experimental control when testing a biological indicator (700) from a previously performed sterilization cycle. When a user selects an indicator (700) to scan, indicator analyzer (102, 800, 950) will verify (block 212) that a control indicator has been analyzed from the same lot or group as the selected indicator (700) by accessing data from server (106) via communication hub (20). A control indicator (700) is a normal biological indicator (700) that has been selected from a group of associated biological indicators (700) and analyzed without first being run through a sterilization cycle and, if the group that the control has been selected from are viable indicators (700), will result in an indication of positive for contamination since it has not been sterilized. By testing a control from a group of indicators (700), a user may minimize the chance that a group of indicators (700) that have been stored or handled incorrectly will be unwittingly used with the system. By building controls to verify (block 212) that a control has been run for the selected indicator (700), the system can partially automate and enforce control testing. Once a control indicator (700) has been verified (block 212), the test indicator (700) may be analyzed (block 214) by indicator analyzer (102, 800, 950) by placing indicator (700) in a test well (810, 954) and allowing indicator analyzer (102, 800, 950) to incubate and analyze (block 214) the biological contents of indicator (700) to determine if contaminants survived a sterilization cycle. Once results are available from a test (block 214), the test may be finalized (block 216) by displaying results via touch screen display (850, 956) of the indicator analyzer (102, 800, 950), providing guidance or recommendations based upon the results; and transmitting results via the communication hub (20) to sterilizing cabinet (100, 150), to server (106), or to both.

Figure 25:
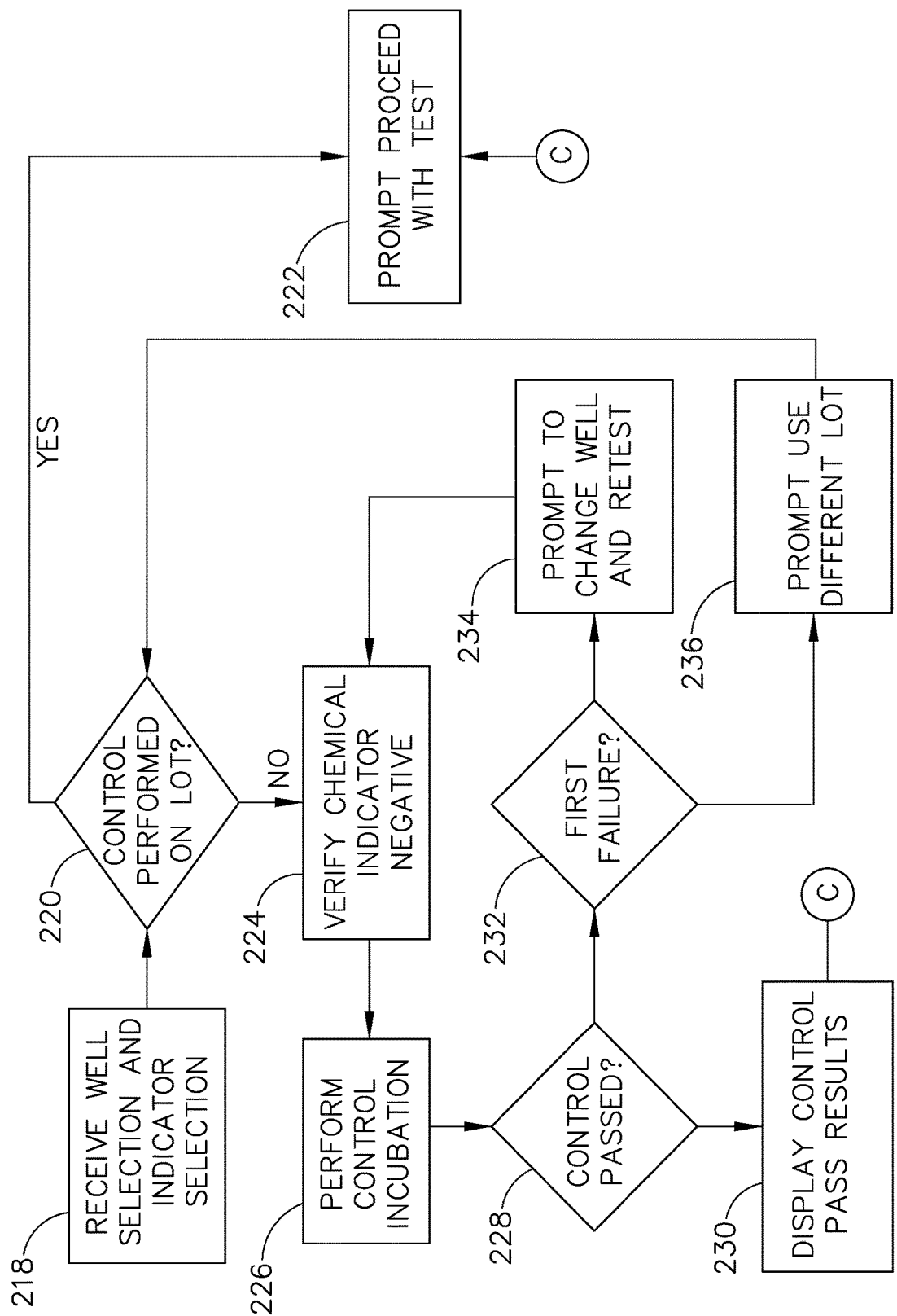
FIG. 25 depicts a flowchart of exemplary steps that may be performed by the indicator analyzer of FIG. 20 to enforce control indicator usage prior to normal testing.

FIG. 25 shows a set of exemplary steps that may be performed by indicator analyzer (102, 800, 950) to verify and enforce the use of a control indicator (700). A user may begin configuring an indicator test by making a selection via a user interface, such as touch screen display (850, 956) of indicator analyzer (102, 800, 950), resulting in a well (810, 954) selection and indicator (700) selection being received (block 218) by indicator analyzer (102, 800, 950). As noted above, indicator analyzer (102, 800, 950) may have multiple testing wells (810, 954) that can receive an indicator (700) and perform incubation and analysis such that multiple indicators (700) may be processed simultaneously. The indicator selection may be performed by scanning or reading a machine readable code or unique identifier on an indicator (700), using reader (870, 960); or by manual entry of indicator (700) information to allow indicator analyzer (102, 800, 950) to identify indicator (700). Identifying indicator (700) allows indicator analyzer (102, 800, 950) to access records on server (106) via communication hub (20) to determine whether the identified indicator (700) comes from a batch or group of indicators (700) that has been control tested; to determine if indicator (700) has already been incubated and analyzed and prevent erroneous retesting; or to identify a sterilization cycle that was performed with indicator (700).

Figure 28:
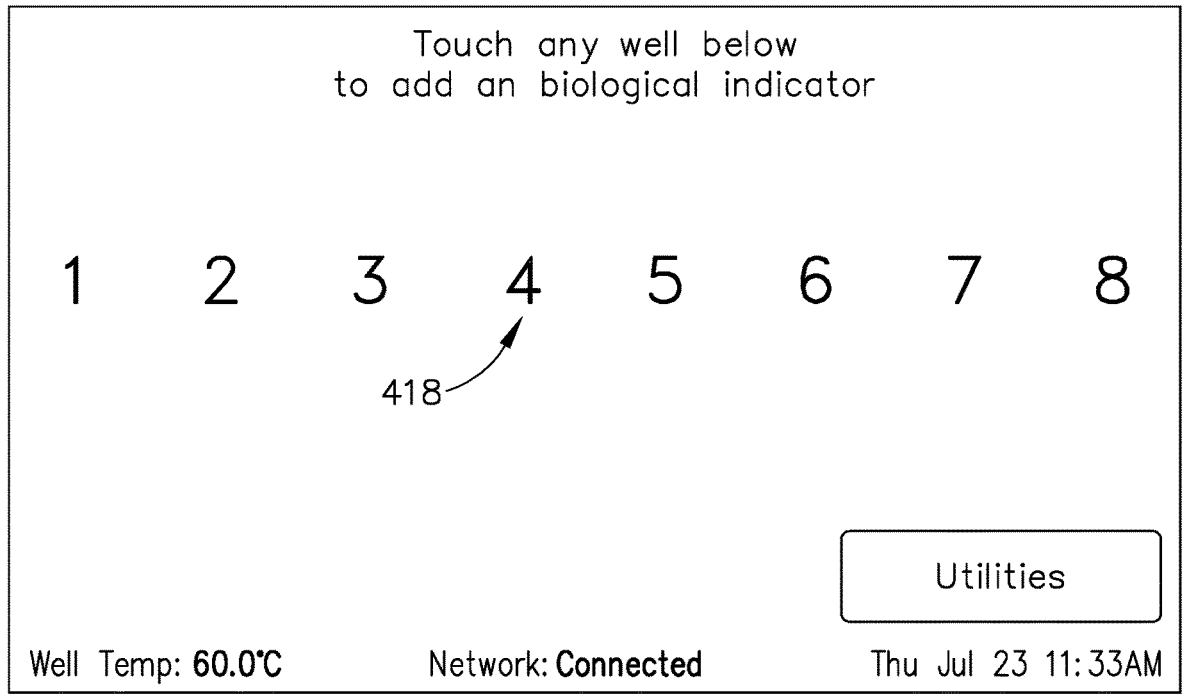
FIG. 28 depicts a screenshot of an exemplary user interface that could be presented via a display of the indicator analyzer of FIG. 20 to allow a user to select a well for analysis.

FIG. 28 shows a screenshot of an exemplary user interface for making a well (810, 954) selection. In the exemplary interface, eight different numbered wells (810, 954) are represented numerically and are selectable by interacting with the well number (418) (e.g., by tapping on the well number (418)) for the desired well (810, 954). An exemplary user interface may be displayed for selecting whether the selected well (810, 954) will receive a control indicator (700), by interacting with a "control" indicator button; or a test indicator (700), by interacting with a "test" indicator button. An exemplary user interface may be displayed for providing guidance to a user for scanning a machine identification from an indicator (700) via reader (870, 960) of indicator analyzer (102, 800, 950).

Figure 29:
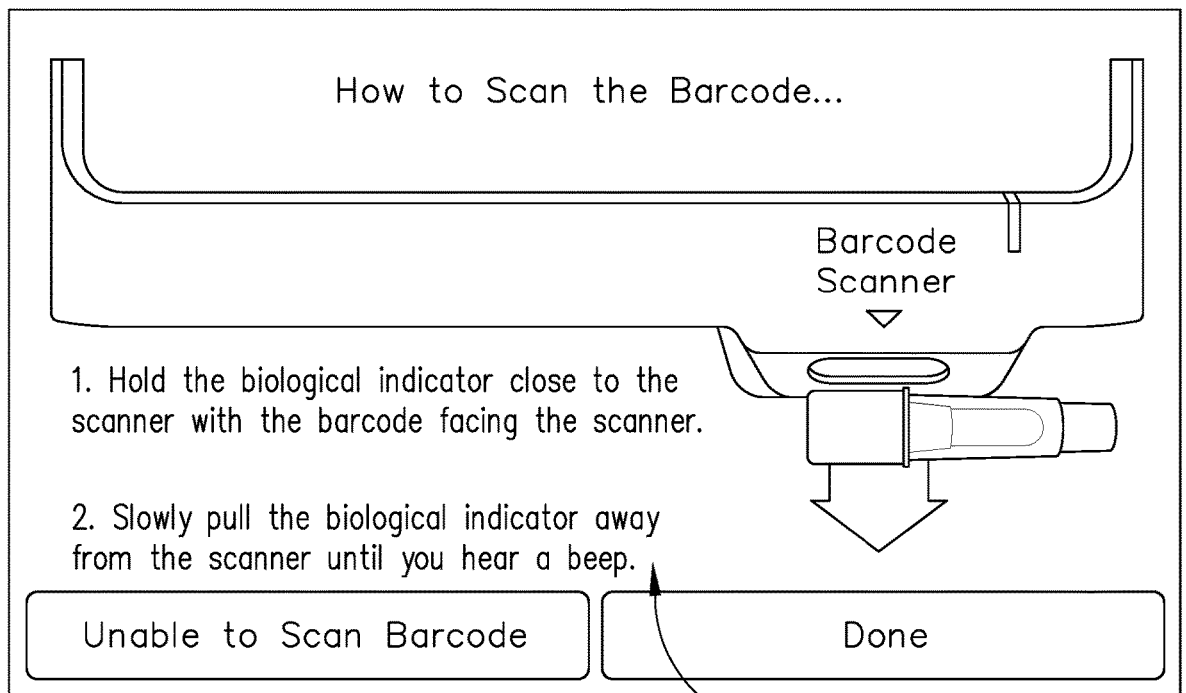
FIG. 29 depicts a screenshot of an exemplary user interface that could be presented via a display of the indicator analyzer of FIG. 20 to guide a user during barcode scanning of an indicator.

FIG. 29 shows a screenshot of an exemplary user interface for providing further guidance to a user (472) for scanning a machine identification from an indicator (700) via reader (870, 960) of indicator analyzer (102, 800, 950). This guidance may include activation of an arrow pointing to the location of reader (960) on indicator analyzer (950), with textual instructions on how to position indicator (700) in relation to reader (870, 960). In some versions, if an indicator analyzer (102, 800, 950) is being used in a setting where it cannot immediately communicate with server (106), or if reader (870, 960) is not available, identification information and sterilization cycle information may be entered manually via a user interface that has manual entry boxes for inputting indicator (700) information and cycle information (e.g., identifying the particular sterilizing cabinet (100), the sterilization cycle type, the sterilization cycle number, the sterilization cycle start time, the sterilization cycle end time, etc.). This additional information will provide a link between a particular indicator (700) and a sterilization cycle that was previously carried out using sterilizing cabinet (100, 150).

Once a well (810, 954) has been selected and an indicator (700) type has been selected (block 218), indicator analyzer (102, 800, 950) may query records from server (106) and identify a lot or group associated with the selected or scanned indicator (700) in order to determine if there has been a recent control indicator (700) analyzed from that lot or group (block 220). For example, if indicators (700) come in lots of 24, each of the 24 indicators (700) was likely manufactured at approximately the same time, from the same components, and was likely to be packaged, shipped, stored, and otherwise handled in a similar manner. Therefore, if a single indicator (700) from the lot of 24 is tested as a control indicator (700) and fails to report as positive for contamination, it may be likely that other indicators (700) from the same lot may be flawed as well, such that those indicators (700) should be discarded in order to avoid false negatives that would erroneously suggest that sterilization cycles were successful. The system may be configured so that indicator analyzer (102, 800, 950) requires a control indicator (700) to be analyzed for each lot, and the results recorded to server (106) and associated with the lot, so that the system can later verify the control (block 220). In some versions a control indicator (700) may be required once per lot, or once every 24 hours per lot, or any other variation on numbers per lot, durations of time between re-testing of control, or other similar configurable testing requirement.

If it is determined that control requirements have been met for the lot of the selected indicator (block 220), the control has been verified and the system may prompt the user to proceed with testing of selected test indicator (700). If it is determined that control requirements for the lot have not been met (block 220), the system will instead notify the user of the requirement for a control to be performed and guide the user through inserting a control indicator (700) from the selected lot into the selected well (810, 954). The system may additionally verify the chemical indicator (block 224) of the control indicator (700) via an interface screen that shows a graphic providing the difference in visual appearance between an unchanged chemical indicator and a changed chemical indicator. A chemical indicator of biological indicator (700) is initially a first color; but during a sterilization cycle a chemical reaction to temperatures or substances used during sterilization causes the chemical indicator to change to a second color, providing a visual indication as to whether a particular indicator (700) has undergone a sterilization cycle. Therefore, the interface described above allows user to verify and indicate that a control indicator (700), which has not undergone a sterilization cycle, is still showing an original color through its chemical indicator. If a user selects otherwise, the system may prompt the user to select a different control indicator (700), as the previously selected control indicator (700) is either flawed or has been used in sterilization cycle.

Once the chemical indicator has been verified by the user and system (block 224), the system will begin to incubate the control indicator (block 226) after the control indicator (700) is inserted into the selected well (810, 954). Each well (810, 954) of indicator analyzer (102, 800, 950) may be equipped with a button, photo eye, or other sensor that allows it to determine when an indicator (700) is inserted into well (810, 954) so that incubation may automatically begin. In some versions, light source (830) and sensor (840) are used to determine when an indicator (700) is inserted into well (810, 954). Various suitable ways in which the presence of an indicator (700) in a well (810, 954) may be sensed will be apparent to those of ordinary skill in the art in view of the teachings herein.

Figure 30:
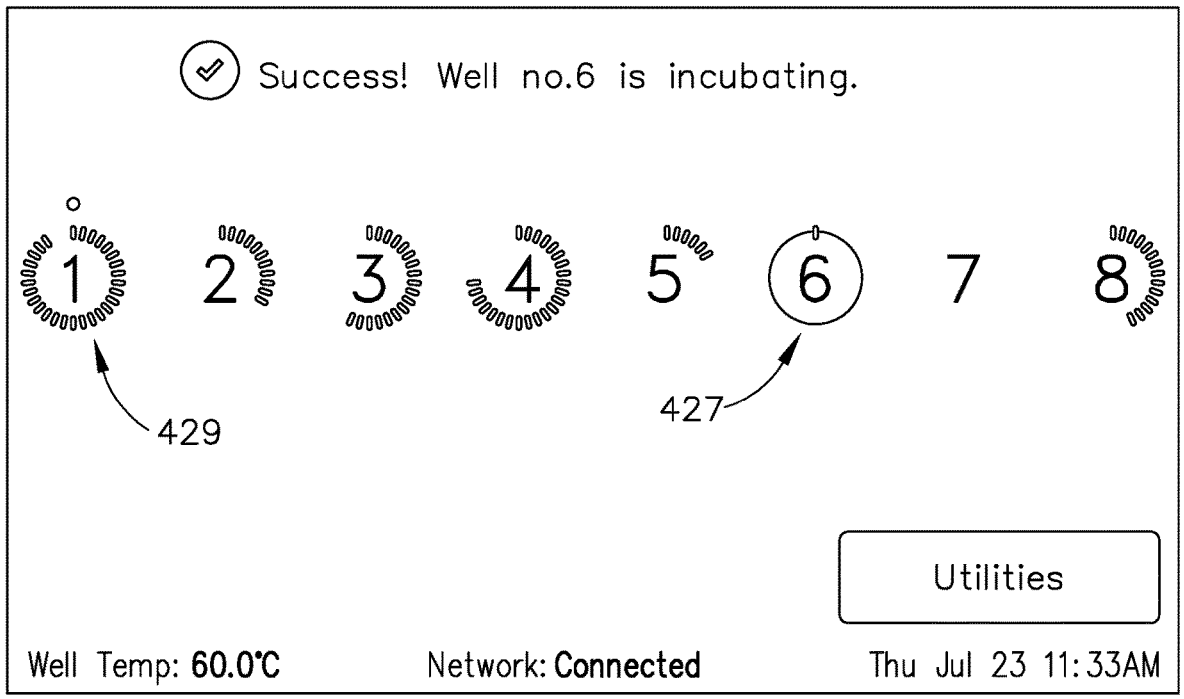
FIG. 30 depicts a screenshot of an exemplary user interface that could be presented via a display of the indicator analyzer of FIG. 20 to indicate to a user that one or more incubation and analysis are being performed.

FIG. 30 shows a user interface that could be displayed to provide updates to a user for each well (810, 954) of an indicator analyzer (102, 800, 950). In FIG. 30, eight wells (810, 954) are shown in varying states, with the incubation and analysis progress of each well (810, 954) shown by an incrementing series of dashes or other symbols (429); or with a colored circle or symbol (427) to indicate a recent change in status for a well (810, 954) that has recently started incubation or analysis, or has recently completed incubation or analysis. Selecting a particular well (810, 954) via the user interface of FIG. 30 may cause indicator analyzer (102, 800, 950) to display a more detailed status screen for the selected well (810, 954) that shows the type of test being performed (431) so that a user may determine whether well (810, 954) is running a control indicator (700) or a test indicator (700), and a more detailed time status so that a user may get a more accurate picture of the remaining time for the incubation and analysis.

Once control indicator (700) incubation and analysis is complete (block 226), indicator analyzer (102, 800, 950) will determine if control indicator (700) tests positive for contamination, which indicates that the control indicator passed. If control indicator (700) results pass (block 228), the control indicator (700) results may be displayed (block 230) via touch screen display (850, 956) of indicator analyzer (102, 800, 950) and transmitted to server (106) to be associated with the lot from which the control indicator (700) was selected so that future test indicators (700) from that lot may be analyzed without interruption. If it is determined that the control failed (block 228), the system will notify a user of the failure via a user interface that indicates the well (810, 954) where the failed control indicator (700) is placed. If it is a first control failure (block 232), the system will indicate that it is a first failure and prompt the user to change wells (810, 954) and test a second control indicator (block 234).

An interface could be shown in the event of a first control indicator (700) failure. By way of example only, such an interface may provide additional guidance to a user to identify the lot that the second control should be selected from; as well as which well (180, 954) to avoid using in a second control. Performing a second control indicator (700) test in a different well (180, 954) allows the system to isolate for a malfunctioning test well (180, 954).

As another merely illustrative example, an interface may allow for identifying a user and guiding the user through performing a second control indicator analysis. The user identification may be used by system administrators to audit the results of the control indicator (700) analysis and ensure that proper steps are taken in the event of a control indicator (700) failure. Following the provided directions, the user may select a new control indicator (700) and return to the step of verifying the chemical indicator (block 224). If proceeding through the steps results in a second control failure (block 228), the system may instead prompt the user to discard the lot from which the previous failed controls were selected from and run a control and test indicator (700) from a different lot (block 236), which may require that the user rerun a sterilization cycle for affected medical devices with a new test indicator (700) from a different lot so that a valid control can be performed for the lot (block 220).

An interface could be displayed in the event of a second control indicator (700) failure. By way of example only, such an interface may provide the user with guidance for handling the second control indicator (700) failure. An additional user interface may be used to identify a user for audit purposes and provide additional guidance in the event of a second control indicator failure.

Figure 26:
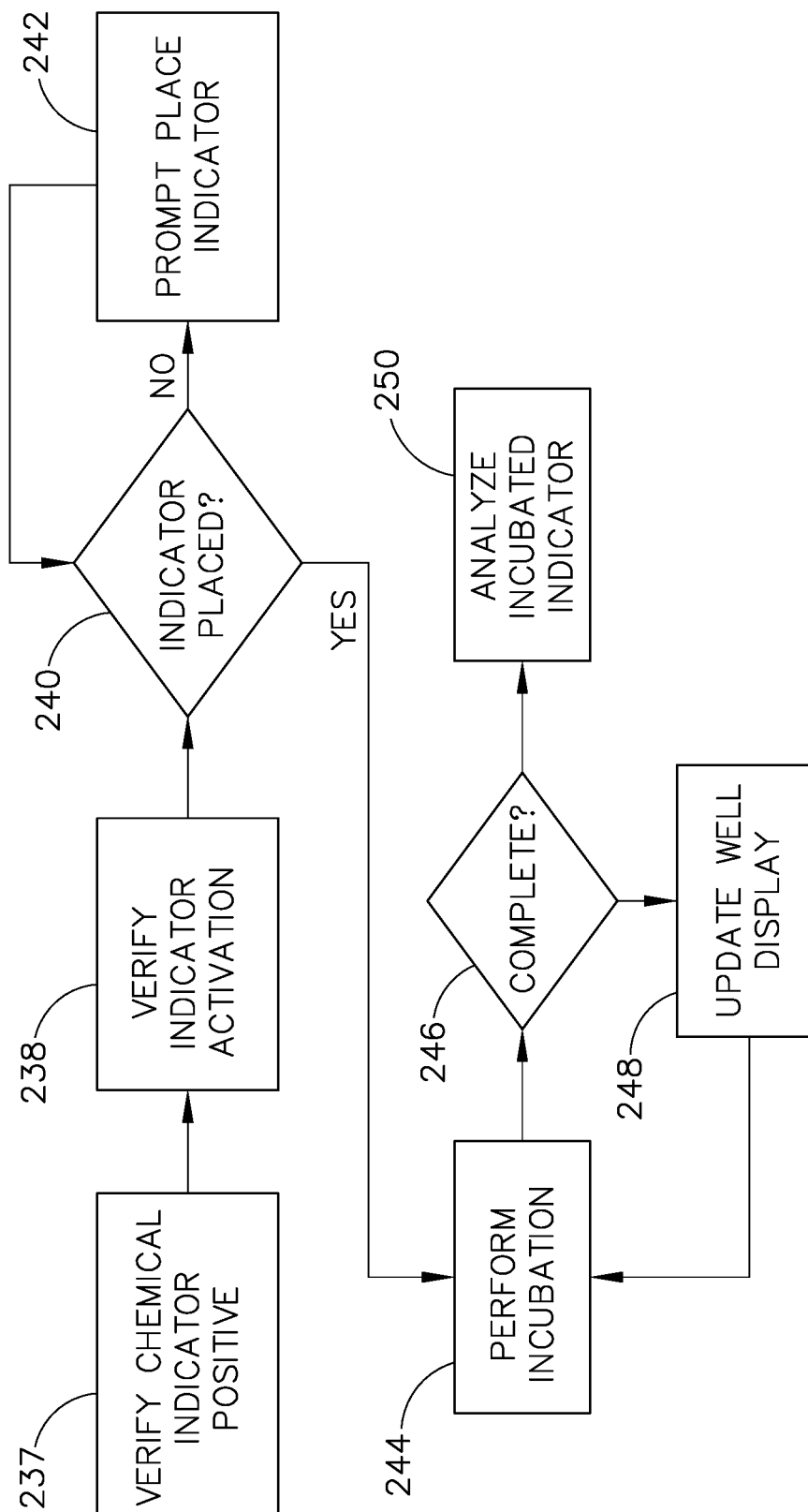
FIG. 26 depicts a flowchart of exemplary steps that may be performed by the indicator analyzer of FIG. 20 to incubate and analyze a test indicator.

FIG. 26 shows a set of exemplary steps that may be performed by indicator analyzer (102, 800, 950) to perform an incubation and test (block 214) on a test indicator (700) after a control indicator (700) has been verified (block 212). Initially, indicator analyzer (102, 800, 950) may verify that the chemical indicator of test indicator (700) shows positive for having undergone a sterilization cycle (block 237). In some instances, touch screen display (850, 956) may provide an interface screen that provides a user with guidance as to whether a chemical indicator is showing an original color or is showing a color indicative of a sterilization cycle; and to receive a selection from the user verifying that the chemical indicator shows positive (block 237) for having undergone a sterilization cycle. Such an interface screen may include graphical representations of indicator (700) with the different colors, with associated input buttons to indicate which color is being observed by the user.

Figure 31:
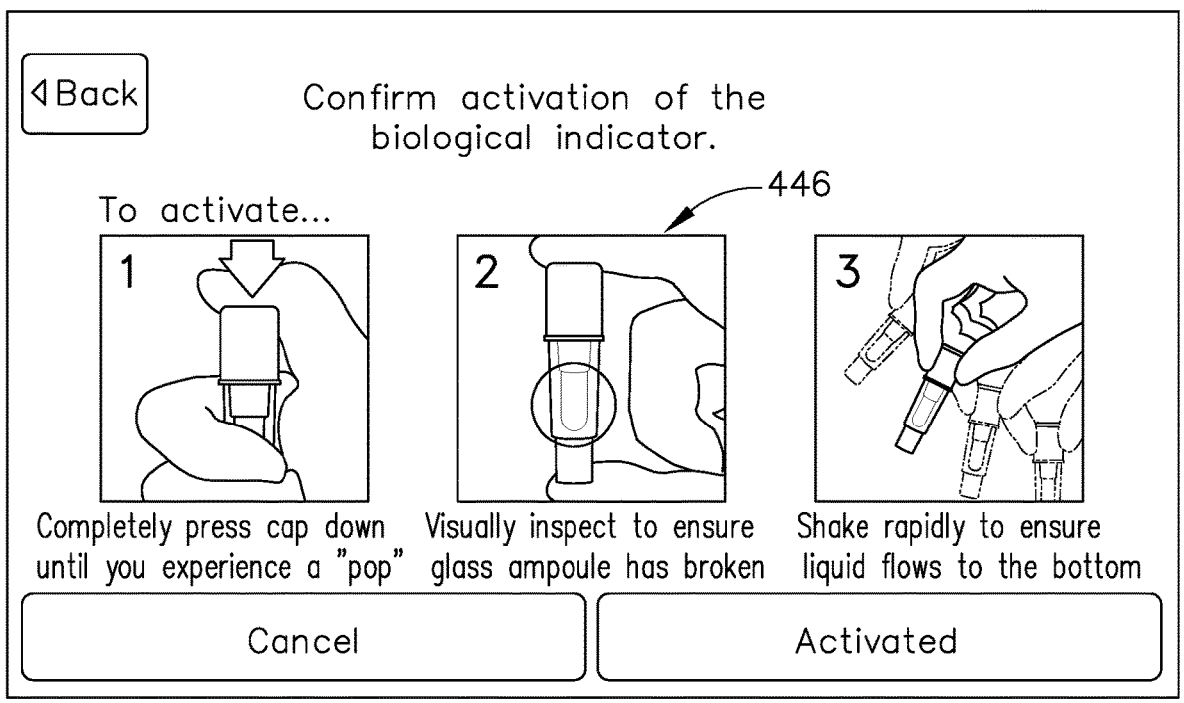
FIG. 31 depicts a screenshot of an exemplary user interface that could be presented via a display of the indicator analyzer of FIG. 20 to guide a user through activating an indicator.

Indicator analyzer (102, 800, 950) may also verify indicator (700) activation with the user (block 238) via a user interface such as that shown in FIG. 31, which provides an illustrated guide (446) for activating and verifying activation of a test indicator (700) prior to incubation and analysis, and for receiving a selection from the user verifying activation (block 238). After indicator activation has been verified (block 238), indicator (700) may be placed (block 240) into the selected test well (810, 954). An interface could be displayed to prompt (block 242) a user to place indicator (700) in the selected test well (810, 954) via a textual and/or graphic instruction, if a sensor of test well (810, 954) does not detect that indicator (700) has been placed (block 240). When a sensor of test well (810, 954), such as a button or photo eye, determines that indicator (700) has been placed (block 240), the incubation may be performed (block 244).

While waiting for the incubation to complete (block 246), indicator analyzer (102, 800, 950) will update well display screens (block 248) regularly so that users may review information on active wells (810, 954). FIG. 32 shows an example of a user interface that could be maintained and updated (block 248) to reflect current information on well (810, 954) status. In particular, FIG. 32 shows a user interface that could be displayed via touch screen display (850, 956) of indicator analyzer (102, 800, 950) to provide more verbose information (450) on an indicator (700) currently being incubated and analyzed in a well (810, 954). Such verbose information could include, for example, the type of biological indicator (700) that is being analyzed, such as a control indicator (700) or test indicator (700), lot number from which indicator (700) was selected, serial number, expiration date, user identification, time that incubation began, date of incubation, verification of chemical indicator status, temperature of incubator, result of incubation and analysis if available, sterilization cycle associated with indicator (700), cycle type, cycle number, cycle start and end time, and other information that may desirably be displayed via indicator analyzer (102, 800, 950).

When incubation is complete (block 246) indicator analyzer (102, 800, 950) may analyze the incubated indicator (700) and determine if any biological contaminants developed or remain after the incubation (block 250). As noted above, in some versions, indicator (700) will contain a liquid solution that will react to biological contaminants such that if a first color is shown there is no contamination, indicating that the sterilization cycle was successful; and if a second color is shown there is contamination, indicating that the sterilization cycle failed. In such versions, analysis of whether indicator (700) is positive or negative for contamination may be performed by use of light source (830) and sensor (840), to detect fluorescence by indicator (700), as described above.

Figure 27:
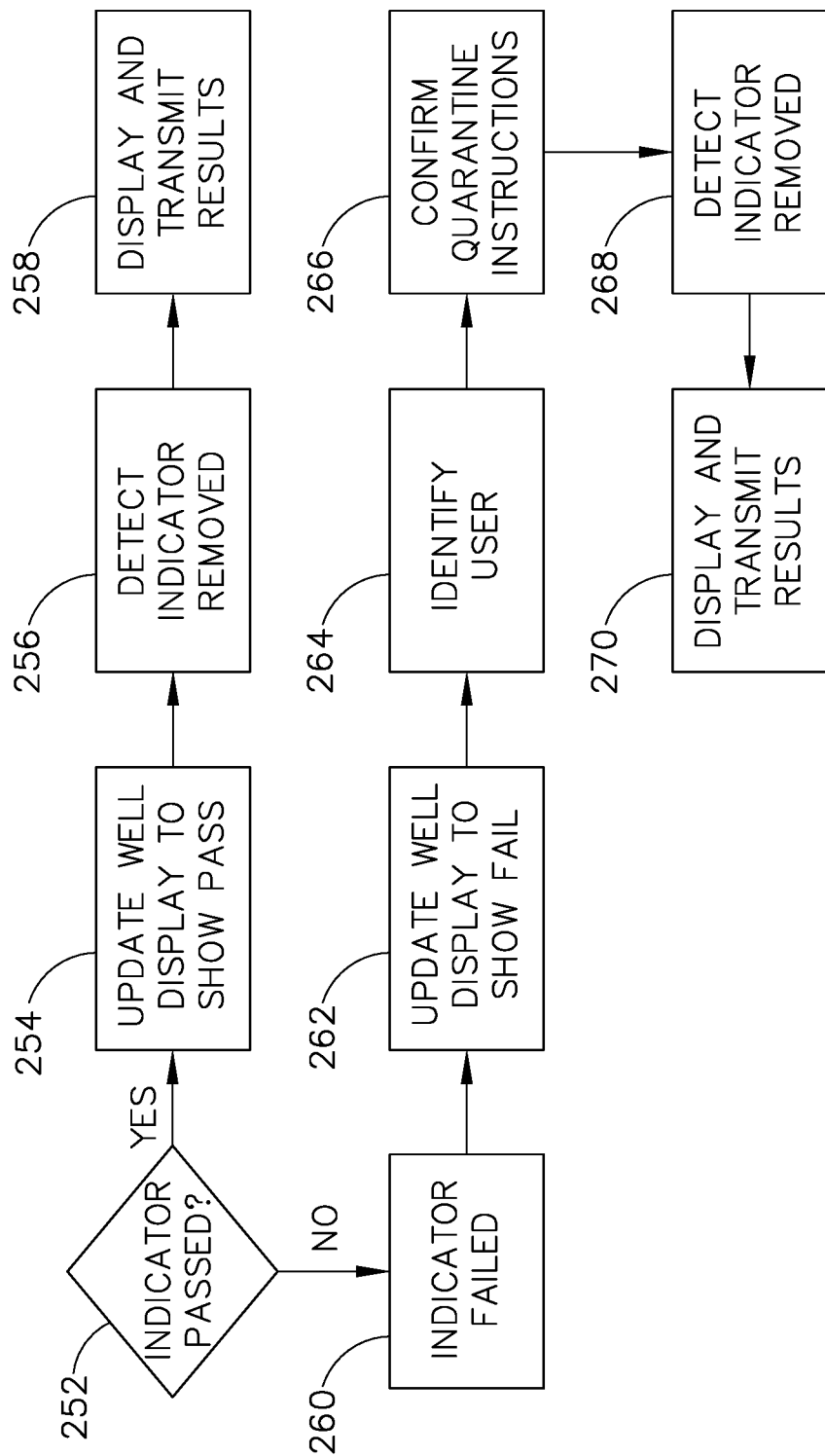
FIG. 27 depicts a flowchart of exemplary steps that may be performed by the indicator analyzer of FIG. 20 to finalize and display the results of an analysis.

FIG. 27 shows a set of exemplary steps that may be performed to display test results and finalize a test (block 216). If the indicator analysis (block 250) indicates that the test indicator (700) is negative for contamination, then indicator (700) has passed (block 252) and indicator analyzer (102, 800, 950) may update the well display interface to indicate to the user that a test indicator (700) has passed (block 254). An interface could be displayed to indicate to a user that a well of the indicator analyzer (102, 800, 950) has completed a with a negative contamination result. The well indicator may be configured with a specific color signifying success, such as green; and/or may include a particular symbol signifying success, such as a checkmark, star, or other symbol, color, or visual indicator.

An interface may be displayed to give a user a more detailed description and guidance after a passed indicator (block 252). Indicator analyzer (102, 800, 950) may then detect when indicator (700) is removed from the test well (block 256) via a sensor situated in test well (810, 954); and display and transmit results (block 258) of the test indicator analysis. In some versions, the results are transmitted (block 258) from indicator analyzer (102, 800, 950) to communication hub (20) in response to a query from communication hub (20), such that the results are pulled from biological indicator analyzer (102, 800, 950) by communication hub (20). In some other versions, the results are pushed to communication hub (20) (block 258) by biological indicator analyzer (102, 800, 950), without requiring a query from communication hub (20).

An interface may be displayed for providing a detailed summary of test results including information such as whether the completed test was for a control indicator (700) or a test indicator (700), a lot number from which indicator (700) was selected, serial number, expiration date, and other similar information as is shown and described in relation to such a status interface and other similar figures. The same interface may provide information on the sterilization cycle, including but not limited to an identification of the sterilization cabinet (100) in which the sterilization cycle was performed, the type of sterilization cycle performed, the sterilization cycle number, the sterilization cycle start time, the sterilization cycle end time, etc. Results of the test indicator analysis may additionally be printed, stored locally on indicator analyzer (102, 800, 950), transmitted to a sterilizing cabinet (100, 150) via communication hub (20), and/or transmitted to a remote server (106) via communication hub (20).

If the indicator analysis (block 250) instead indicates that indicator (700) is positive for contamination, the system determines that indicator (700) failed (block 260) and may update the well display of indicator analyzer (102, 800, 950) to reflect the failure (block 262). An interface could be displayed to indicate to a user that an indicator (700) in a specific well failed, and to receive a confirmation or acknowledgment of the failure from the user.

An interface may be displayed to a user after an indicator (700) failure (block 260) in order to provide additional information and guidance for the user. Another interface may be displayed to a user in order to receive (block 264) an identification of the user for audit and follow up purposes, and to provide (block 266) additional guidance on quarantine and re-sterilization procedures for affected equipment. Identification of the user (block 264) may be useful where an administrator later wishes to ensure that quarantine procedures were correctly followed. An interface could be displayed in order to receive a confirmation from a user that quarantine procedures or instructions were read and acknowledged. (block 266). Indicator analyzer (102, 800, 950) may then display a user interface in order to prompt a user to remove the failed indicator. Indicator analyzer (102, 800, 950) may detect the removal of the indicator (block 268) via a sensor of indicator analyzer (102, 800, 950) and display and transmit test results (block 270) in response. In some versions, the results are transmitted (block 270) from indicator analyzer (102, 800, 950) to communication hub (20) in response to a query from communication hub (20), such that the results are pulled from biological indicator analyzer (102, 800, 950) by communication hub (20). In some other versions, the results are pushed to communication hub (20) (block 270) by biological indicator analyzer (102, 800, 950), without requiring a query from communication hub (20).

Another interface could be displayed to provide a verbose summary of test results that could include information such as test type, lot number, serial number, lot expiration date, sterilization cycle information, and additional information. Information generated from the failed test may also be printed, stored locally on the indicator analyzer (102, 800, 950), or transmitted to one or more of the server (106) and sterilizing cabinet (100, 150) via the communication hub (20). Test results from a failed test may be used by sterilizing cabinet (100, 150), the server (106), or both to identify medical devices that may need to be quarantined or re-sterilized, to identify sterilizing cabinets (100, 150) that are malfunctioning, to identify users that are not following proper sterilization procedures, or to identify other associations with data stored on server (106) or sterilizing cabinet (100, 150) that may be used to improve the effectiveness of future sterilization cycles.

C. Exemplary Enzyme Analysis Methods

Figure 33:
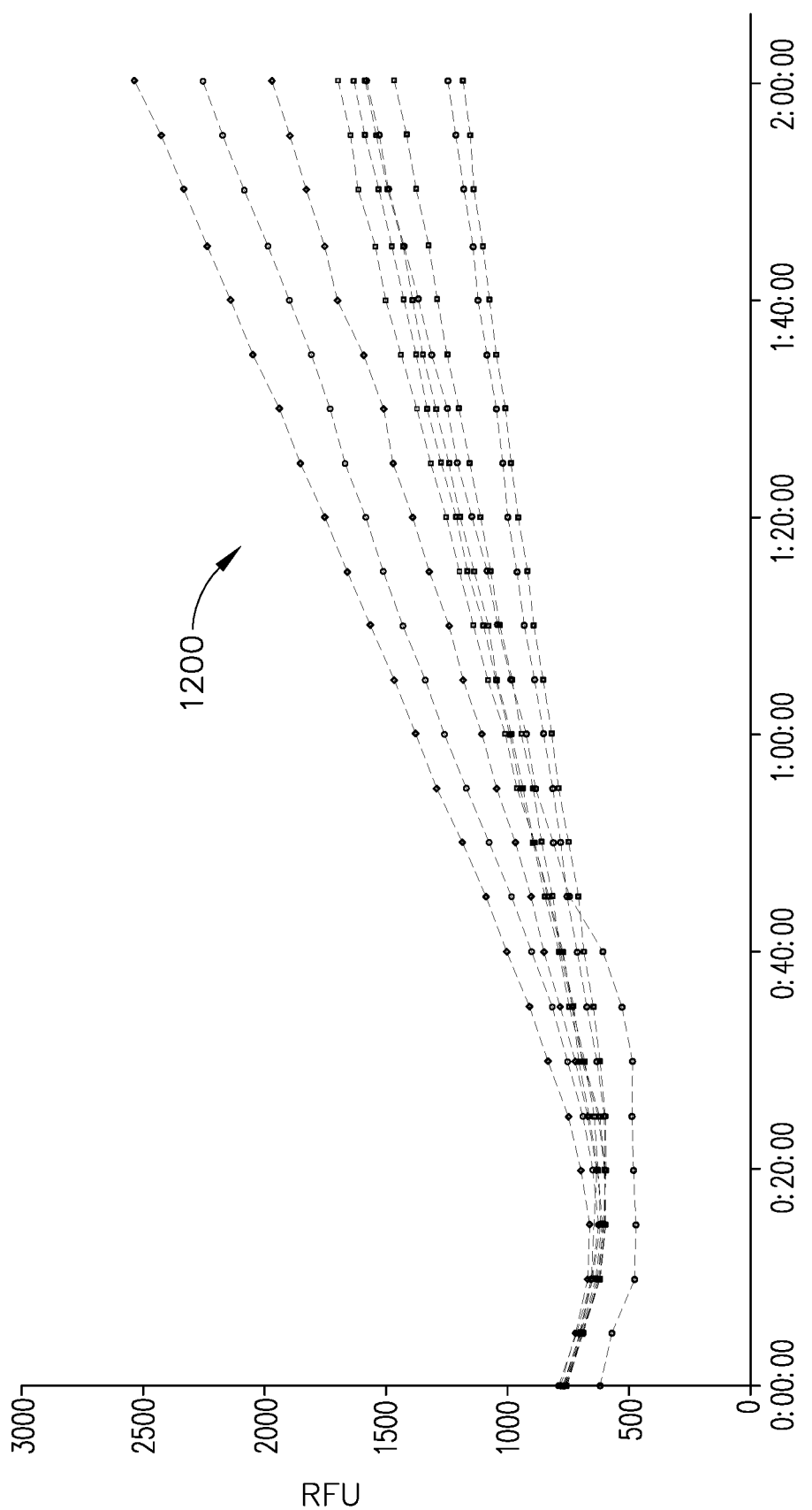
FIG. 33 depicts a graph showing a plot of relative fluorescence units over time for several biological indicators having active enzyme contained therein as detected by the indicator analyzer of FIG. 20.

As discussed above, indicator analyzer (102, 800, 950) is configured to analyze biological indicators (700) in order to determine whether active enzymes are present in fluid (732), by detecting fluorescence of fluid (732). This is accomplished by activating light source (830) and using sensor (840) to detect any fluorescence in fluid (732) in response to illumination from light source (830) during the incubation period in well (810, 954). FIG. 33 shows the fluorescence of a first group (1200) of biological indicators (700) over a period time (i.e., during an incubation period), as detected by indicator analyzer (102, 800, 950). The biological indicators (700) of first group (1200) were subject to a non-efficacious sterilization cycle in sterilization cabinet (100, 150). In FIG. 33, the fluorescence is shown in relative fluorescence units (RFUs), which are known units of measurement. As can be seen, the fluorescence value drops during the initial part of the incubation period. By way of example only, this drop in fluorescence may be due to heating of fluid (732) in well (810, 954) of indicator analyzer (102, 800, 950). After this initial drop, the fluorescence value increases over the remainder of the incubation period. This increase in fluorescence value indicates that each biological indicator (700) of the first group (1200) contains an active enzyme. Thus, the sterilization processes encountered by biological indicators (700) of the first group (1200) were failures.

Figure 34:
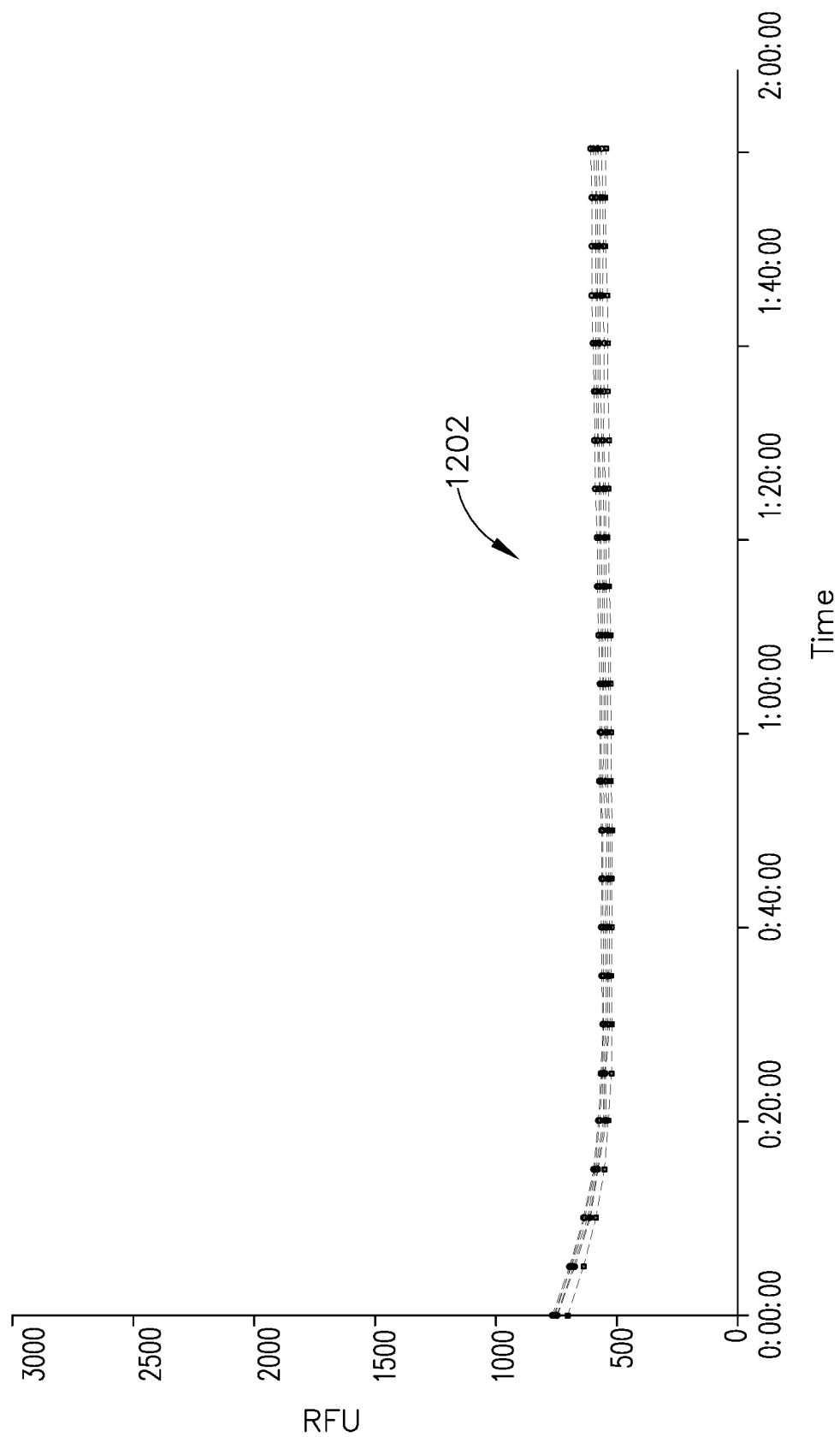
FIG. 34 depicts a graph showing a plot of relative fluorescence units over time for several biological indicators having inactive enzyme contained therein as detected by the indicator analyzer of FIG. 20.

FIG. 34 shows the fluorescence of a second group (1202) of biological indicators (700) over a period time (i.e., during an incubation period), as detected by indicator analyzer (102, 800, 950). The biological indicators (700) of second group (1202) were subject to an efficacious sterilization cycle in sterilization cabinet (100, 150). In FIG. 34, the fluorescence is again shown in relative fluorescence units (RFUs). As can be seen, the fluorescence value drops during the initial part of the incubation period. As noted above, this drop in fluorescence may be due to heating of fluid (732) in well (810, 954) of indicator analyzer (102, 800, 950). After this initial drop, the fluorescence value stays substantially constant over the remainder of the incubation period. This constancy in fluorescence value indicates that none of the biological indicators (700) of the second group (1202) contains an active enzyme. Thus, the sterilization processes encountered by biological indicators (700) of the second group (1202) were successful.

In order to determine whether the fluorescence of biological indicators (700) will increase or remain substantially constant after the initial part of the incubation period where the fluorescence value drops, it may be desirable to monitor the fluorescence value for a substantial period of time in order for the results of the analysis to be sufficiently reliable or trustworthy. In other words, it may be desirable to continue monitoring the fluorescence value for a substantial period of time after the initial part of the incubation period where the fluorescence value drops, in order to determine with sufficient certainty that the fluorescence value has increased to a point indicating that active enzyme is present (indicating failure of the sterilization process); or that the fluorescence value has remained substantially constant indicating that no active enzyme is present (indicating success of the sterilization process). There may also be a competing interest in providing the analysis as quickly as possible in order to provide a satisfactory wait time for the end user. Thus, it may be desirable to provide analysis of biological indicators (700) as quickly as possible without compromising the reliability of the results of such analysis.

In order to speed up the analysis of biological indicators (700), it may be desirable to find the point at which the rate of product creation is at its maximum, then compare the maximum rate to a critical value. With an excess of substrate relative to enzyme concentration, this maximum rate may be directly related to the amount of enzyme present and thereby to the efficaciousness of the sterilization cycle.

Figure 35:
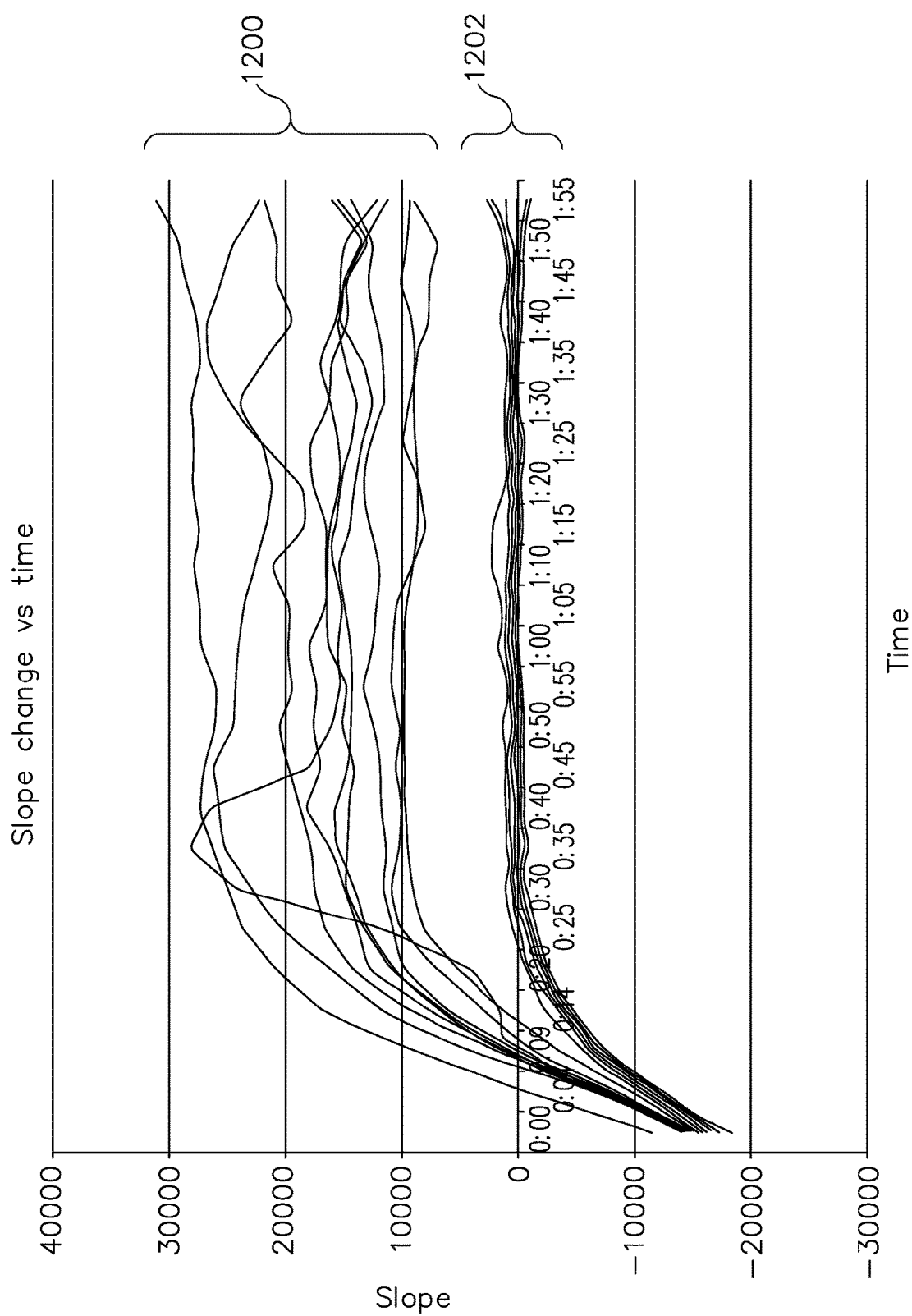
FIG. 35 depicts a graph showing a plot of the change in slope of the relative fluorescence units for the biological indicators of FIGS. 33 and 34.

As can be observed in FIGS. 33 and 34, the slopes of the curves are fairly constant after the initial drop. FIG. 35 shows the change in the slope over 15 minute increments of the data in FIGS. 33 and 34. As can be seen in FIG. 35, after about 20 minutes the slope reaches a maximum rate and then holds there for the two-hour incubation period. While there is some noise in the reading, there is not a significant increase in the slope after 20 to 30 minutes. FIG. 35 also clearly illustrates the difference in the maximum slope for the first group (1200) versus the second group (1202). In particular, the average maximum slope for the first group (1200) is greater than 10,000; while the average maximum slope for the second group (1202) is approximately 1,600. This slope discrepancy is large enough that it may be easily detected in a reliable fashion. Moreover, this slope discrepancy may be detected rather quickly (e.g., on the order of approximately 20-30 minutes).

In view of the foregoing, rather than only tracking absolute fluorescence values, it may be beneficial to track the slopes associated with changes in fluorescence values. Tracking the slopes may provide relative rapid yet reliable analysis indicating whether a biological indicator (700) was subject to an efficacious sterilization cycle or a non-efficacious sterilization cycle. To this end, after an incubation period has begun in indicator analyzer (102, 800, 950), indicator analyzer (102, 800, 950) may initially monitor the fluorescence of biological indicator (700) and calculate the slope. Indicator analyzer (102, 800, 950) may then compare the slope against a critical value (e.g., some number that is greater than 1,600, such as 2,000; 5,000; 7,500; etc.). If the slope is greater than the critical value, then indicator analyzer (102, 800, 950) may conclude that an active enzyme is present in biological indicator (700); and trigger any of the various sterilization process failure notifications described herein. If the slope is less than the critical value, then indicator analyzer (102, 800, 950) may continue to monitor the slope until the slope reaches a maximum value. By way of example only, it may take approximately 20 to 30 minutes for the slope to reach a maximum value. If the slope is still less than the critical value at this stage, then indicator analyzer (102, 800, 950) may conclude that no active enzyme is present in biological indicator (700); and trigger any of the various sterilization process success notifications described herein.

While the foregoing examples have been provided in the context of monitoring fluorescence of fluid (732) in biological indicator (700), it should be understood that the same concepts may be readily applied to other detectable parameters (e.g., iridescence, absorbance, etc.) that change based on the presence of an active enzyme in fluid (732). Similarly, while the foregoing examples have been provided in the context of biological indicators (700) that have undergone sterilization processes in sterilization cabinet (100, 150), it should be understood that the same concepts may be readily applied to any sterilization modality that uses an enzymatic reaction and/or in various other kinds of enzyme detection contexts.

Figure 36:
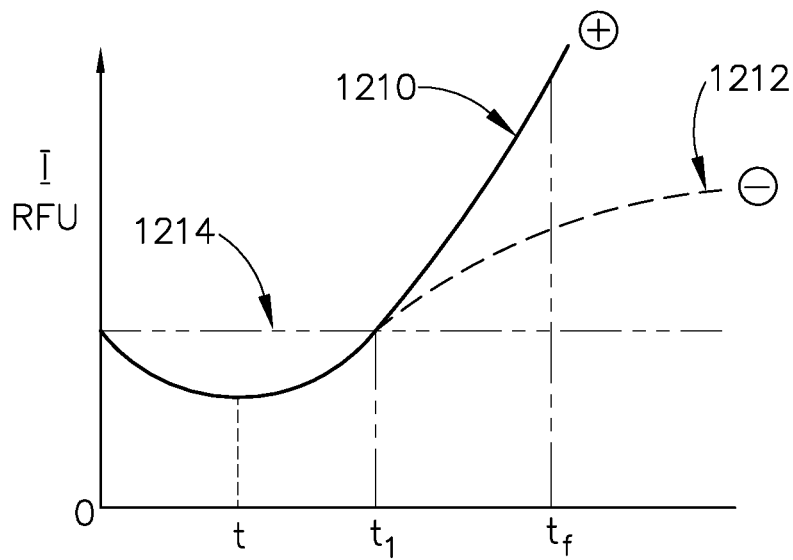
FIG. 36 depicts a graph showing a plot of relative fluorescence units over time, along with an associated formula that may be executed by the indicator analyzer of FIG. 20, associated with determining whether an active enzyme is present according to a first exemplary method.
Figure 37:
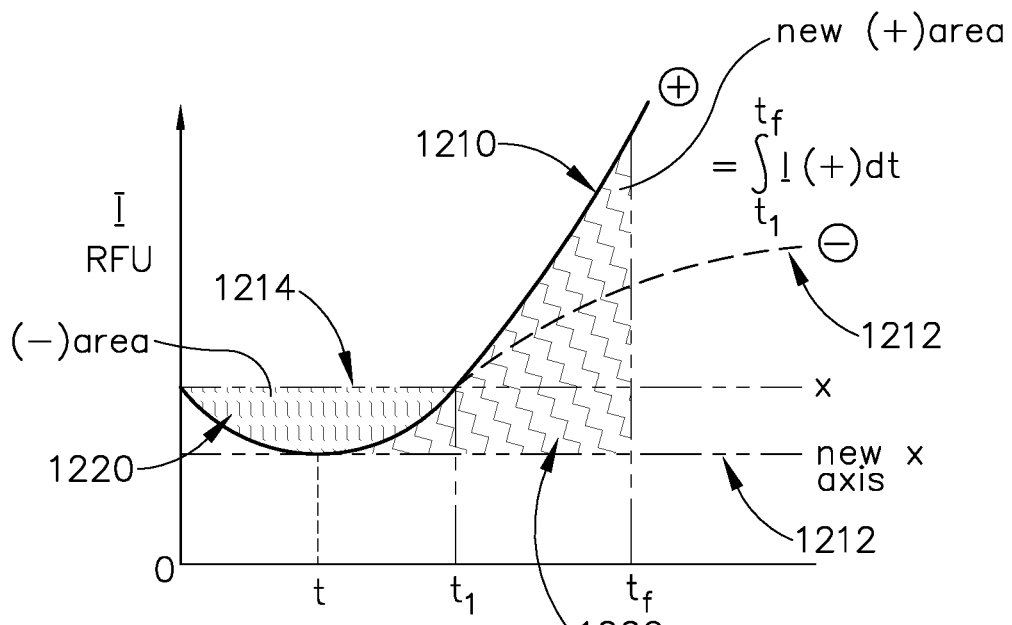
FIG. 37 depicts a graph showing a plot of relative fluorescence units over time, along with an associated formula that may be executed by the indicator analyzer of FIG. 20, associated with determining whether an active enzyme is present according to a second exemplary method.

FIGS. 36-37 show additional plots of fluorescence (in units of RFU) over time to illustrate additional exemplary methods of determining whether an active enzyme is present in fluid (732) of biological indicator (700). Just like the method described above with respect to FIGS. 33-35, the methods described below may be carried out using indicator analyzer (102, 800, 950). The methods associated with FIGS. 36-37 seek to filter out fluorescence data associated with the initial part of the incubation process where the fluorescence value encounters the initial drop (e.g., due to heating of fluid (732) in well (810, 954)). In both of the following examples, the variable t' is defined as the time at which the fluorescence value has completed the initial drop.

In the graph shown in FIG. 36, the curve (1210) is a plot associated with a biological indicator (700) having an active enzyme (indicating a non-efficacious sterilization cycle); while the curve (1212) is a plot associated with a biological indicator (700) lacking an active enzyme (indicating an efficacious sterilization cycle). The line (1214) is a horizontal line drawn parallel to the x-axis (which represents time), at the value associated with the initial fluorescence of biological indicator (700). The lower limit of the integral formula shown in FIG. 36, $t_1$, is taken at the point where line (1214) intersects curve (1210, 1212). The test statistic is given by the integral shown in FIG. 36.

In the graph shown in FIG. 37, the curve (1210) is again a plot associated with a biological indicator (700) having an active enzyme (indicating a non-efficacious sterilization cycle); while the curve (1212) is again a plot associated with a biological indicator (700) lacking an active enzyme (indicating an efficacious sterilization cycle). The line (1214) is again a horizontal line drawn parallel to the x-axis (which represents time), at the value associated with the initial fluorescence of biological indicator (700). Again, the lower limit of the integral formula shown in FIG. 37, $t_1$, is taken at the point where line (1214) intersects curve (1210, 1212). However, in this example t' is defined as the time at which the negative area (1220) (i.e., the area under line (1214) before reaching $t_1$) is halved; or alternatively at the centroid of the negative area (1220). This does not necessarily require finding the precise minimum value in curve (1210, 1212), but it still yields an integration starting point where the biologically relevant luminous intensity or fluorescence begins. The integration is then performed on the luminous intensity or fluorescence taken from $t_1$ to $t_f$, which represents the end of the incubation period analysis cycle, to generate the test statistic. As shown, this determines the area between curve (1210, 1212) and a new horizontal line (1216). This horizontal line is parallel to the x-axis and is at the value associated with the minimum fluorescence value associated with time t'.

Regardless of whether the test statistic is evaluated using the method described above with respect to FIG. 36 or the method described above with respect to FIG. 37, the test statistic may be compared to a predefined critical value. The critical value would serve as a threshold indicating whether biological indicator (700) contains an active enzyme or lacks an active enzyme. It should be understood that curve (1210) would yield a test statistic that exceeds the critical value, thereby indicating a non-efficacious sterilization cycle; while curve (1212) would yield a test statistic that falls below the critical value, thereby indicating an efficacious sterilization cycle. It should also be understood that the "trapezoidal method" may be used to perform integration in accordance with the methods described above. Various suitable ways in which a critical value may be identified for the purposes described herein will be apparent to those of ordinary skill in the art. It should also be understood that the fluorescence of biological indicators (700) may be analyzed using other techniques.

VI. Exemplary Communication Hub Device and Methods

A. Exemplary Communication Hub Device

Figure 39:
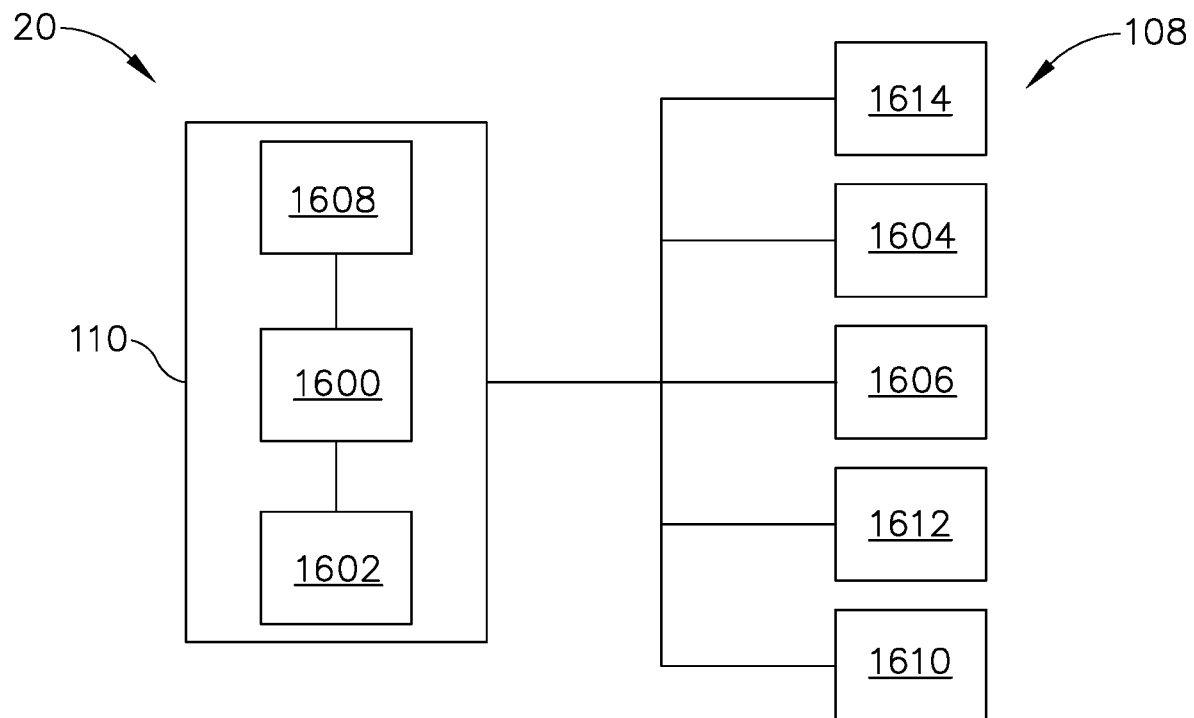
FIG. 39 depicts a schematic view of an exemplary communication hub that may be used to provide monitoring of and communications with one or more other devices within the system of FIG. 1 via a user device.

FIG. 39 shows a schematic view of an exemplary communication hub (20) that may be used within system (10) to provide monitoring of and communication with one or more other devices (100, 102, 106) via a user device (108). Communication hub (20) shown in FIG. 39 includes a housing or case (110) containing a processor (1600) and memory (1602) for storing and manipulating data, and a network interface (1608) for communicating with outside devices such as the various devices (100, 102, 106, 108) shown in FIG. 1. Memory (1602) may include one or more of a random access memory, a read only memory, a volatile memory, a non-volatile memory, an internal hard drive, an external hard drive, a USB storage device, a flash memory storage device, a network storage device, and/or other similar forms of memory. Network interface (1608) may allow a wired connection between two or more devices, such as by Ethernet, USB, fiber optic, and/or other wired data transmission medium; and/or may allow wireless connection between two or more devices, such as by Wi-Fi, Bluetooth, radio transmission, or other wireless data transmission medium.

FIG. 39 shows a version of a communication hub (20) that does not have a display, keyboard, or other interface that a user directly interacts with. Instead, that communication hub (20) may be in communication with a user device (108) via the network interface (1608), and a user may interact with the communication hub (20) via a display (1606) and user input (1604) of the user device (108). In this manner, the communication hub (20) may provide information to the user device (108), which the user device (108) may render via a display (1606) such as a computer monitor or mobile device touch screen. Communication hub (20) may further receive user input from the user device (108) via a user input (1604) such as a keyboard, mouse, or other input device. This allows a user to, for example, use a device (108) such as a laptop computer to view information and configurations of other devices in communication with hub (20), such as sterilizing cabinet (100) and biological indicator analyzer (102), on the laptop display (1606); and to navigate and modify such configurations and information via the laptop keyboard and mouse (1604).

Other devices or features that may be present in a user device (108) or connected to a user device include an alternate input (1614) such as an imaging scanner, microphone, NFC or RFID scanner, and similar input devices, a printer (1612), and an alternate output device (1610), such as a speaker, indicator light, vibration function, or similar output devices. With such additional devices or features, information and configuration from devices connected to communication hub (20) may be printed via a printer (1612) so that hard copies are available. An alternate user input (1614) such as an imaging scanner may be used to read barcodes or other image identifiers from a device to assist in identifying devices, connecting to devices, or changing configurations on devices. An alternate output (1610) may be used to provide additional forms of notification or feedback to a user, such as providing an audible alarm when a device unexpectedly loses connection to communication hub (20). Other examples of devices or features that may be present in communication hub (20) or a user device (108) in communication with hub (20) will be apparent to those of ordinary skill in the art in light of the disclosure herein.

Figure 40:
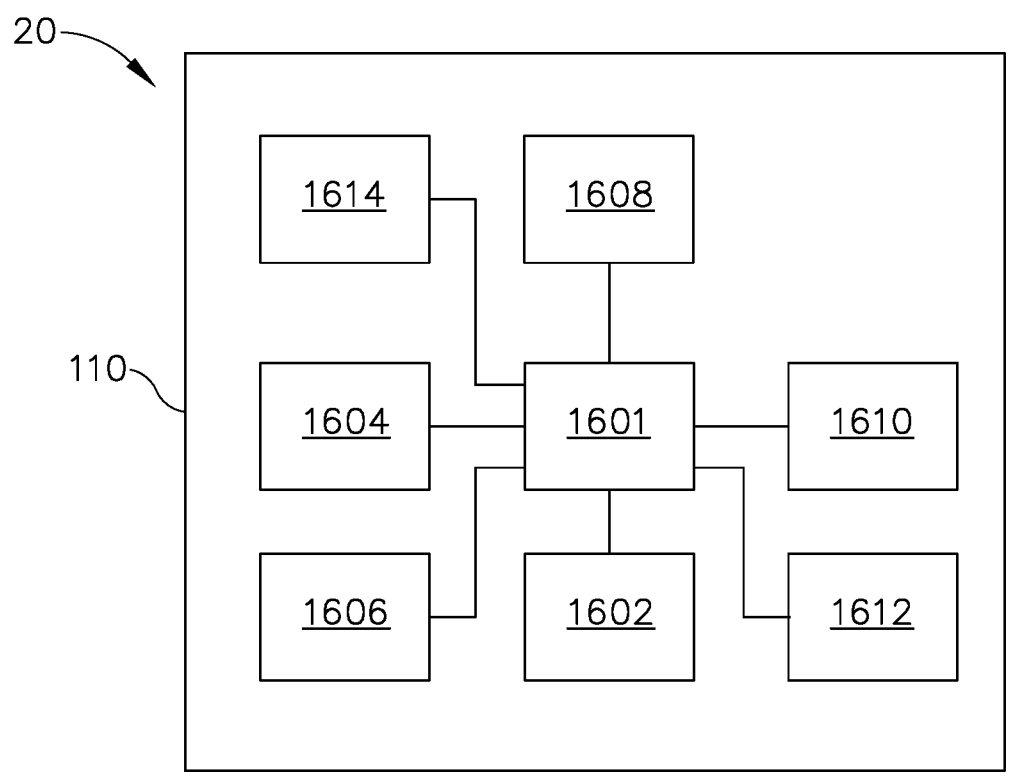
FIG. 40 depicts a schematic view of an exemplary alternative communication hub that may be used to provide monitoring of and communications with one or more other devices.

While such features and components may be spread across several devices, such as a combination of a communication hub (20) and user device (108) as shown in FIG. 39, such features and components may alternatively be integrated into a single device such as the communication hub (20) of FIG. 40. In the exemplary hub of FIG. 40, communication hub (20) may be a proprietary device such as a kiosk or other piece of specialized equipment, or may be a computer or server configured with additional components. Such a communication hub (20) may contain or be directly connected to a processor (1601), memory (1602), user interface (1604), display (1606), network interface (1608) alternate output (1610), printer (1612), and alternate input (1614) having the capabilities described above or otherwise as will be apparent to one of ordinary skill in the art in light of the disclosure herein. Such a communication hub (20) could be, for example, a specially built kiosk containing one or more of the listed components in a single case, body, or frame, but could also include, for example, a computer or server having a memory, processor, and wireless communication expansion card configured to serve as a communication router for devices it is in wireless communication with. Other variations exist, and a particular implementation of a communication hub (20) and available features will depend upon such factors as desired cost, setting, use, and other factors.

B. Exemplary Communication Hub Overview

Figure 38:
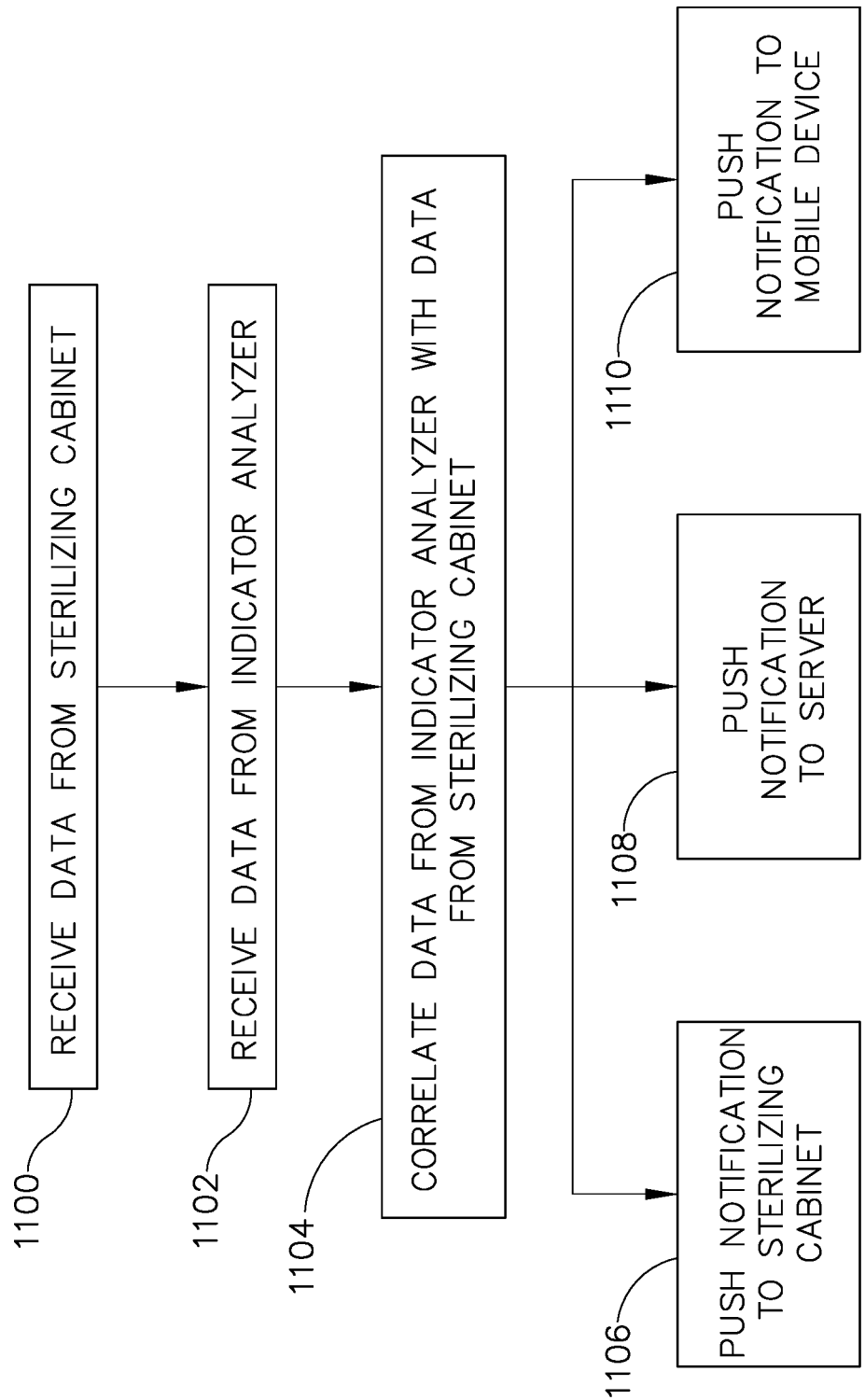
FIG. 38 depicts a flowchart of exemplary steps that may be performed by a communication hub of the system of FIG. 1.

FIG. 38 shows a set of exemplary steps that may be performed by communication hub (20). As noted above, communication hub (20) may be in communication with sterilizing cabinet (100, 150) via communication module (164). Communication hub (20) may thus receive data from sterilizing cabinet (100, 150) (block 1100). By way of example only, and as noted above, this data may include information relating to a sterilization cycle (block 210, block 504). As also noted above, communication hub (20) may be in communication with biological indicator analyzer (102, 800, 950) via communication module (860). Communication hub (20) may thus receive data from biological indicator analyzer (102, 800, 950). By way of example only, and as noted above, this data may include information relating to passage of a biological indicator analysis (block 1006) or failure of a biological indicator analysis (block 1016). While communication hub (20) is shown as only being in communication with one sterilizing cabinet (100, 150) and with one biological indicator analyzer (102, 800), it should be understood that a single communication hub (20) may be in communication with several sterilizing cabinets (100, 150) and/or several biological indicator analyzers (102, 800).

Communication hub (20) may further process the data received from sterilizing cabinet (100, 150) and biological indicator analyzer (102, 800, 950) by correlating the data (block 1104). By way of example only, when communication hub (20) receives a notification from biological indicator analyzer (102, 800, 950) that a particular biological indicator (700) failed a biological indicator analysis (block 1016), regardless of whether this information is pushed to communication hub (20) or pulled by communication hub (20), communication hub (20) may correlate the identity of that particular biological indicator (700) with a particular sterilizing cabinet (100, 150). Communication hub (20) may further correlate the identity of that particular biological indicator (700) with particular sterilization cycles performed by that particular sterilizing cabinet (100, 150, 950). With this correlated information, communication hub (20) may identify sterilization cycles whose success may be questionable, such that the sterility of the medical devices that were purportedly sterilized during such sterilization cycles is also questionable.

Having identified sterilization cycles whose success may be questionable, and thus medical devices whose sterility may be questionable, communication hub (20) may automatically send out notifications to various other devices in order to prevent such medical devices from being used before being put through another sterilization process. By way of example only, communication hub (20) may push a notification to sterilizing cabinet (100, 150) (block 1106) indicating the sterilization cycles whose success may be questionable, and thus medical devices whose sterility may be questionable. Sterilizing cabinet (100, 150) may relay this notification to a user by presenting the screen of FIG. 17 (described above) via touch screen display (160).

In addition or in the alternative, communication hub (20) may push a notification to server (106) (block 1108) indicating the sterilization cycles whose success may be questionable, and thus medical devices whose sterility may be questionable. Of course, communication hub (20) may also push a notification to server (106) indicating when a biological indicator (700) passed analysis (block 1000) and/or other information associated with operation of sterilizing cabinet (100, 150) and/or biological indicator analyzer (102, 800, 950).

In addition or in the alternative, communication hub (20) may push a notification to one or more mobile devices (block 1110), such as an operator of system (10), etc., indicating the sterilization cycles whose success may be questionable, and thus medical devices whose sterility may be questionable. In some versions, communication hub (20) pushes such notifications to a mobile device associated with a person who was identified as a user of sterilizing cabinet (100, 150) and/or a person who was identified as a user of biological indicator analyzer (102, 800, 950) (e.g., during the user identification step (block 906)). Of course, communication hub (20) may also push a notification to one or more mobile devices indicating when a biological indicator (700) passed analysis (block 1000) and/or other information associated with operation of sterilizing cabinet (100, 150) and/or biological indicator analyzer (102, 800, 950).

Other suitable ways in which communication hub (20) may push notifications to other devices will be apparent to those of ordinary skill in the art in view of the teachings herein.

It should also be understood that communication hub (20) may be used to provide software updates, firmware updates, and other information to sterilizing cabinet (100, 150) and/or biological indicator analyzer (102, 800, 950). As another merely illustrative example, communication hub (20) may be used to provide hospital policy information to sterilizing cabinet (100, 150), such as hospital policy relating to the frequency of use of biological indicators (700). Other suitable ways in which communication hub (20) may be used will be apparent to those of ordinary skill in the art in view of the teachings herein.

C. Exemplary Communication Hub Methods and Interfaces

Figure 41:
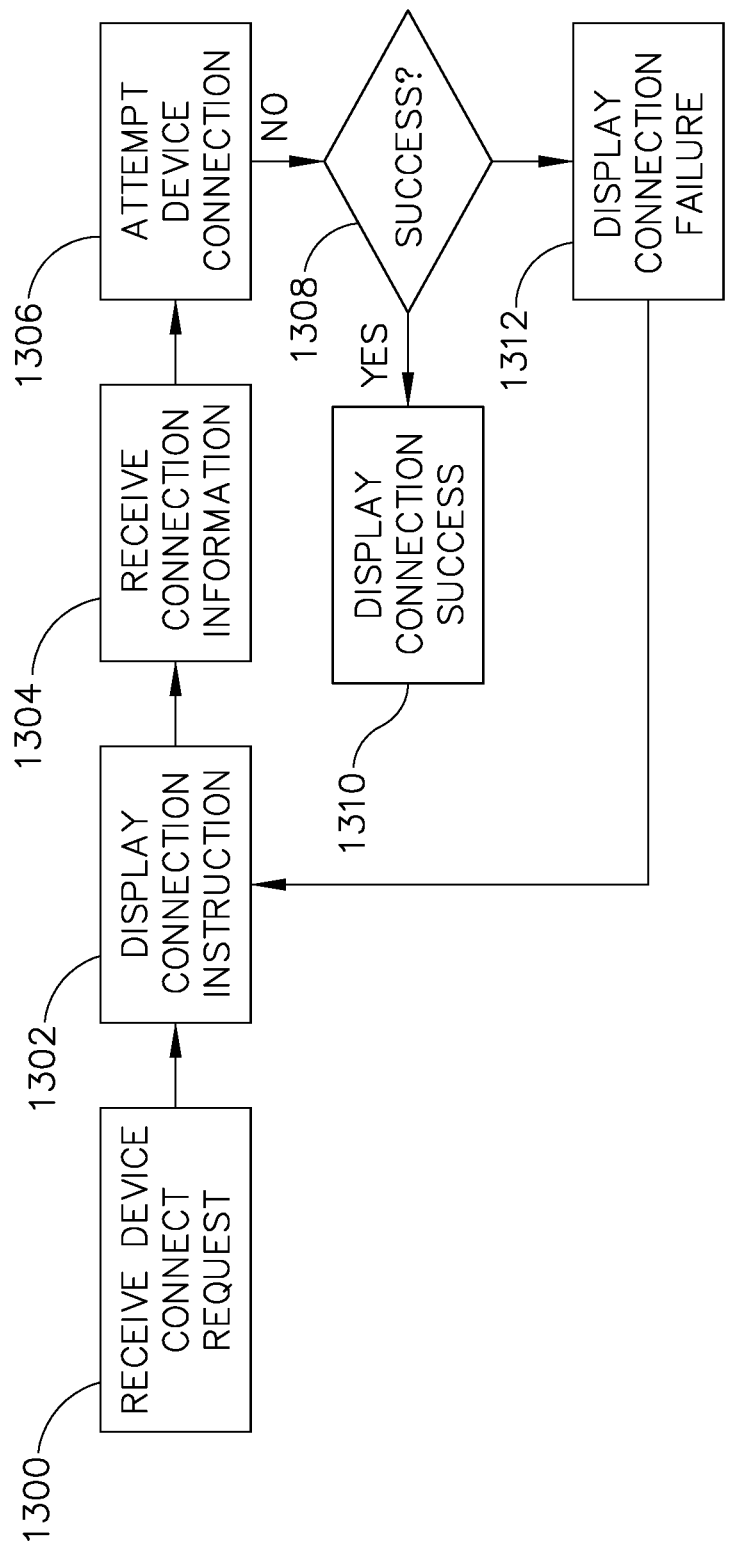
FIG. 41 shows an exemplary set of steps that may be performed using a communication hub, such as that shown in FIG. 39 or that shown in FIG. 40, to manage connections between the communication hub and one or more medical device processing components.

FIG. 41 shows an exemplary set of steps that may be performed using a communication hub (20) such as that shown in FIG. 39-40 to manage connections between the communication hub (20) and one or more processing components (100, 102, 104, 150, 800). These steps may be performed at various times, such as when a new processing component (100, 102, 104, 150, 800) is created and configured for the communication hub (20), or when an existing processing component (100, 102, 104, 150, 800) has been moved to a new physical location or a new network location.

A connection request may be received (block 1300) by the communication hub (20) from a user device (108). The connection request may identify a component (100, 102, 104, 150, 800) for which network communication needs to be established, or may identify a component (100, 102, 104, 150, 800) for which network communication has previously been established that needs to be modified or re-established. The communication hub (20) may identify the component (100, 102, 104, 150, 800) type based upon the received (block 1300) request, and display (block 1302) connection instructions and input options that are specific to that component (100, 102, 104, 150, 800) via a display (1606) of the user device (108). Information provided by a user in response to the connection instructions may be received (block 1304) by the communication hub (20) and used to attempt (block 1306) to establish a network connection between the communication hub (20) and the component (100, 102, 104, 150, 800).

If this network connection is successful, as may be indicated by a successful network ping, packet exchange, or other transmission of information, a success message may be displayed (block 1310) indicating that the component (100, 102, 104, 150, 800) connection was successful. If the network connection was not successful, perhaps due to user error or a network issue, a connection failure message may be displayed (block 1312) and the user may be returned to a step where the connection instructions are displayed (block 1302) so that further attempts may be made.

FIGS. 59-60 show several examples of interfaces that may be displayed to a user as part of the steps of FIG. 41. It should be understood that the interfaces of FIGS. 59-60 may be shown on a display of user device (108). In addition, or in the alternative, in cases where communication hub (20) has its own display (1606), the interfaces of FIGS. 59-60 may be shown on display (1606) of communication hub (20).

FIG. 59 shows an example of an interface that may be displayed to a user when displaying (block 1302) connection instructions (1501, 1504) to a user. Such an interface may also have a network identifier (1502) where a unique identifier for a device may be provided, which may include an IP address, a MAC address, a proprietary addressing identifier, or other identifier. Also included may be an interface element that may be interacted with in order to test a connection (1500) before submitting the connection information. Interacting with a test connection (1500) tool may cause the communication hub (20) to send a test ping, packet, or communication to the identified device (1502) and report whether it was successfully received. An interface may be displayed to a user when displaying (block 1310) connection success after a successful (block 1308) device connection attempt (block 1306).

FIG. 60 shows an alternate exemplary interface that may be used to display (block 1302) connection instructions to a user. The interface of FIG. 60 shows additional features that a device connection interface may have, such as a dynamically generated code (1506) that may be generated by either the communication hub (20) or the connecting component (100, 102, 104, 150, 800), and then provided to the other component (100, 102, 104, 150, 800) which may use the code to locate and connect to the component (100, 102, 104, 150, 800) via the network. For example, in some versions, the communication hub (20) is configured to generate a connection code by interacting with an interface element (1508) to cause a connection code (1506) to be displayed.

The connection code (1506) may then be entered via an interface of the target component (100, 102, 104, 150, 800), such as a sterilizing cabinet (100) or indicator analyzer (102) keyboard or touch screen, which is able to determine the communication hub (20) network identity and location based upon the code. The target component (100, 102, 104, 150, 800) may send a test communication to the communication hub (20) that, when received, may be used by the communication hub (20) to identify the network identity and location of the target device.

An alternate exemplary interface may be used to display (block 1302) connection instructions to a user, as well as a username and password requirement that may be required in addition to identifying the target component (100, 102, 104, 150, 800), which may be useful when connecting to devices (100, 102, 104, 150, 800) that store sensitive medical information and which must be protected with some level of authentication. Other alternate examples of interfaces may be used to display (block 1310) a success message after a successful (block 1308) connection attempt (block 1306).

In addition to using generated codes that may be decrypted or interpreted in order to identify a component (100, 102, 104, 150, 800) within a network for connection and unique identifiers such as IP address or MAC address, other methods exist that may be used to help connect or pair devices (100, 102, 104, 150, 800) with communication hub (20). For example, using an alternate input (1614) such as a barcode or QR code scanner, or a mobile device camera configured to capture an image of a barcode or QR code, or a wireless technology such as NFC or RFID, device connection may be completed between a communication hub (20) and a target component (100, 102, 104, 150, 800). For example, one or both devices (100, 102, 104, 150, 800) could have or display a physical tag with a visual identifier or a wireless tag with a unique identifier, and such information may be captured by a user device (108) with an alternate input (1614) and used to complete the connection. This could also include, for example, a sterilizing cabinet (100) having a QR code or NFC tag that, when scanned, automatically populates and submits network identifier information to complete the connection. Such a tag could be physically placed on the equipment, or could be displayed via a display of the equipment, or transmitted via a wireless communication transmitter of the equipment. Such a machine readable code, once read, could provide the information needed to complete the connection, or could provide instructions to retrieve the needed information from another location on the network such as a network identity server, which may contain one or more records identifying various devices on the network and what their current network location is. Variations on the steps and interfaces shown and discussed in relation to FIG. 41 exist, and will be apparent to those of ordinary skill in the art in light of the disclosure herein.

Figure 42:
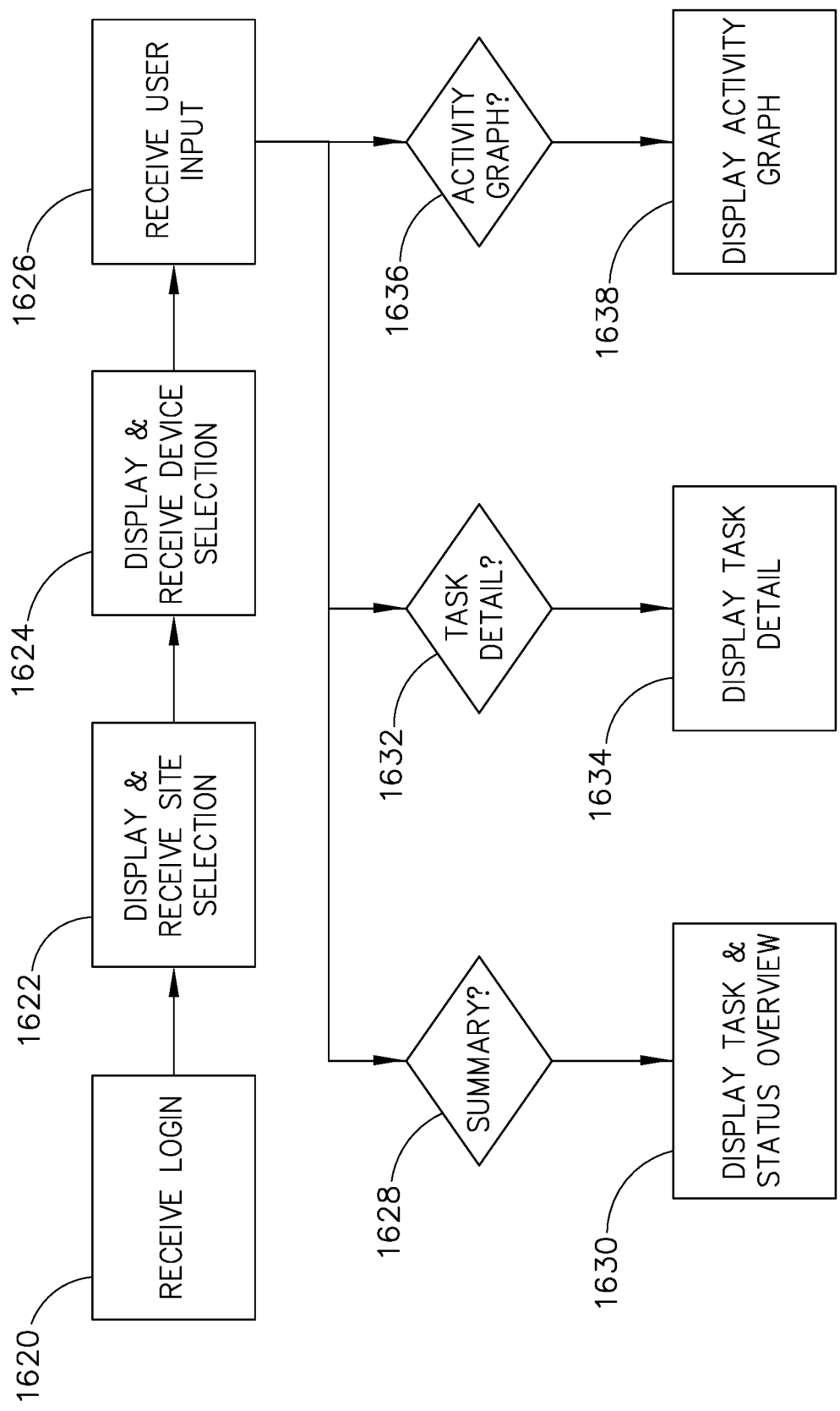
FIG. 42 shows an exemplary set of steps that may be performed using a communication hub, such as that shown in FIG. 39 or that shown in FIG. 40, to manage one or more medical device processing components.

FIG. 42 shows an exemplary set of steps that may be performed using a communication hub (20) such as that shown in FIGS. 39-40 to manage one or more processing components (100, 102, 104, 150, 800). Initially, the communication hub (20) may receive (block 1620) a user's login information such as password and username from a user device (108). While not required, a user login may provide additional security that may be desirable before allowing a user to access a system that displays medical records and information. One or more sites may also be displayed to a user, and a site selection received (block 1622) identifying a particular site or sites that a user wishes to monitor and manage processing components (100, 102, 104, 150, 800) at.

A site may be a geographical location such as a hospital, or may be a particular location within a hospital, such that a hospital may have a single site or multiple sites. A site may have one or more communication hubs (20) providing connectivity and monitoring of processing components (100, 102, 104, 150, 800) at that site.

Once a site is specified, one or more devices (100, 102, 104, 150, 800) may be displayed to a user, and a component (100, 102, 104, 150, 800) selection may be received (block 1624) identifying a particular component (100, 102, 104, 150, 800) or devices (100, 102, 104, 150, 800) that the user wishes to monitor or manage. Once one or more devices (100, 102, 104, 150, 800) have been selected to view or manage, the communication hub (20) may receive (block 1626) user input from the user device (108) requesting summary information (block 1628) for a device or devices, task details (block 1632) for one or more tasks presently or previously performed on a component (100, 102, 104, 150, 800), or an activity graph (block 1636) or other visualization of tasks presently or previously performed on a component (100, 102, 104, 150, 800). In response to received (block 1626) requests, the communication hub (20) may transmit information to the user device (108) configured to cause the user device (108) to display (block 1630) an overview of task information for one or more devices (100, 102, 104, 150, 800), display (block 1634) detailed information for a task, or display (block 1638) a visualization of task information for a component (100, 102, 104, 150, 800).

Figure 45:
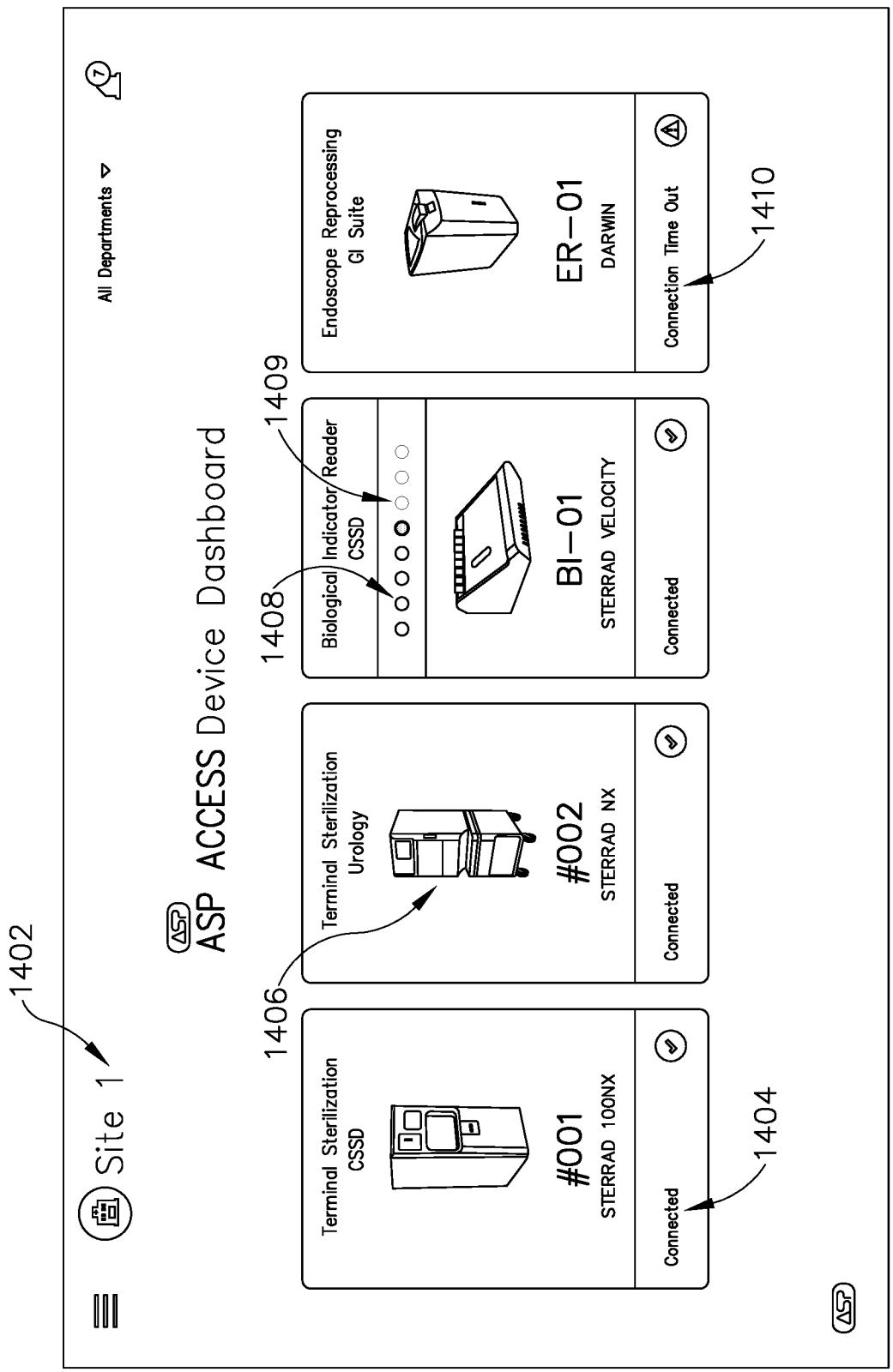
FIG. 45 shows an example of an interface that may be used to select a medical device processing component via a user device coupled with the communication hub of FIG. 39 or directly via the communication hub of FIG. 40.

FIGS. 45-57 show several examples of interfaces that may be displayed to a user during one or more of the steps shown in FIG. 42. A hospital site selection interface may be displayed as part of displaying and receiving (block 1622) a hospital site selection from a user. FIG. 45 shows a component (100, 102, 104, 150, 800) selection interface that may be displayed as part of displaying a receiving a device selection from a user. While the interface of FIG. 45 shows four devices (100, 102, 104, 150, 800), it should be understood that any number of devices may be supported by scaling the display, individual icons, or adding additional interface elements to allow scrolling or page navigation of icons.

A site identifier (1402) indicates the user's site selection. A device status indicator may show that the component (100, 102, 104, 150, 800) is connected to the communication hub (20), or that there is an issue with the device connection (1410). A device icon (1406) may show a visual representation of a device to aid in selecting a component (100, 102, 104, 150, 800). This may be helpful, for example, when a user is accessing the communication hub (20) via a user device (108) such as a mobile phone, and a user is physically present at a sterilization cabinet (100) and wishes to monitor and manage its performance. Such a visual icon (1406) may aid the user in identifying the correct component (100, 102, 104, 150, 800) to view and manage. Additional device specific status indicators may also be shown, such as a biological indicator well (810) status for an indicator analyzer (102, 800), which may show whether a particular indicator well (810) is currently in use (1408) or open for use (1409). Such a feature may allow a clinician that needs to analyze an indicator to identify and locate an indicator analyzer (102, 800) that has currently available well (810) capacity using a mobile user device (108) rather than by physically locating the indicator analyzer (102, 800) and visually confirming whether or not a well (810) is available.

Figure 46:
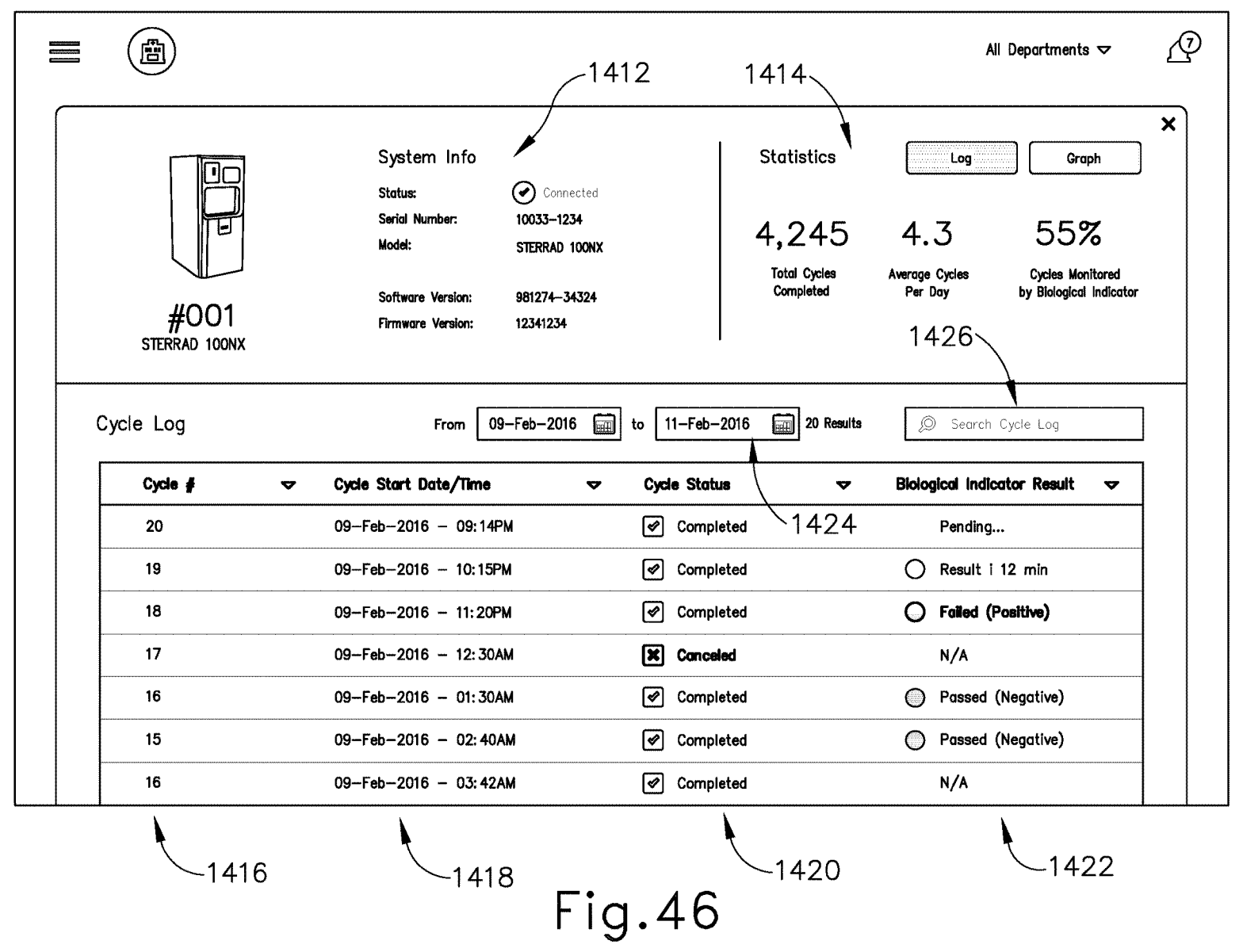

FIG. 46 shows an interface that may be displayed to a user as part of displaying (block 1630) a task and status overview (1412) for a single component (100, 102, 104, 150, 800) to a user. Information shown may include a device identifier and icon, a statistics summary (1414) showing information such as how many sterilization cycles a sterilizing cabinet (100, 150) has completed, a number of cycles run per day, and a number of sterilization cycles in which a biological indicator has been used. Also shown may be a table having a row for each sterilization cycle performed, which may include columns such as a cycle identifier (1416), a cycle start time (1418), a cycle status (1420) indicating whether the cycle completed, failed, or was canceled, and a biological indicator result (1422) indicating whether an indicator was used, and whether the indicator determined that the sterilization cycle was a success or a failure. Also present on such an interface may sorting or filtering options, allowing a table to be sorted according to one or more of the columns, a date range selection (1424) allowing cycles present in the table to be restricted to a certain date range, and a cycle search (1426) allowing for a particular cycle number, date, status, or indicator result to be searched for.

Figure 47:
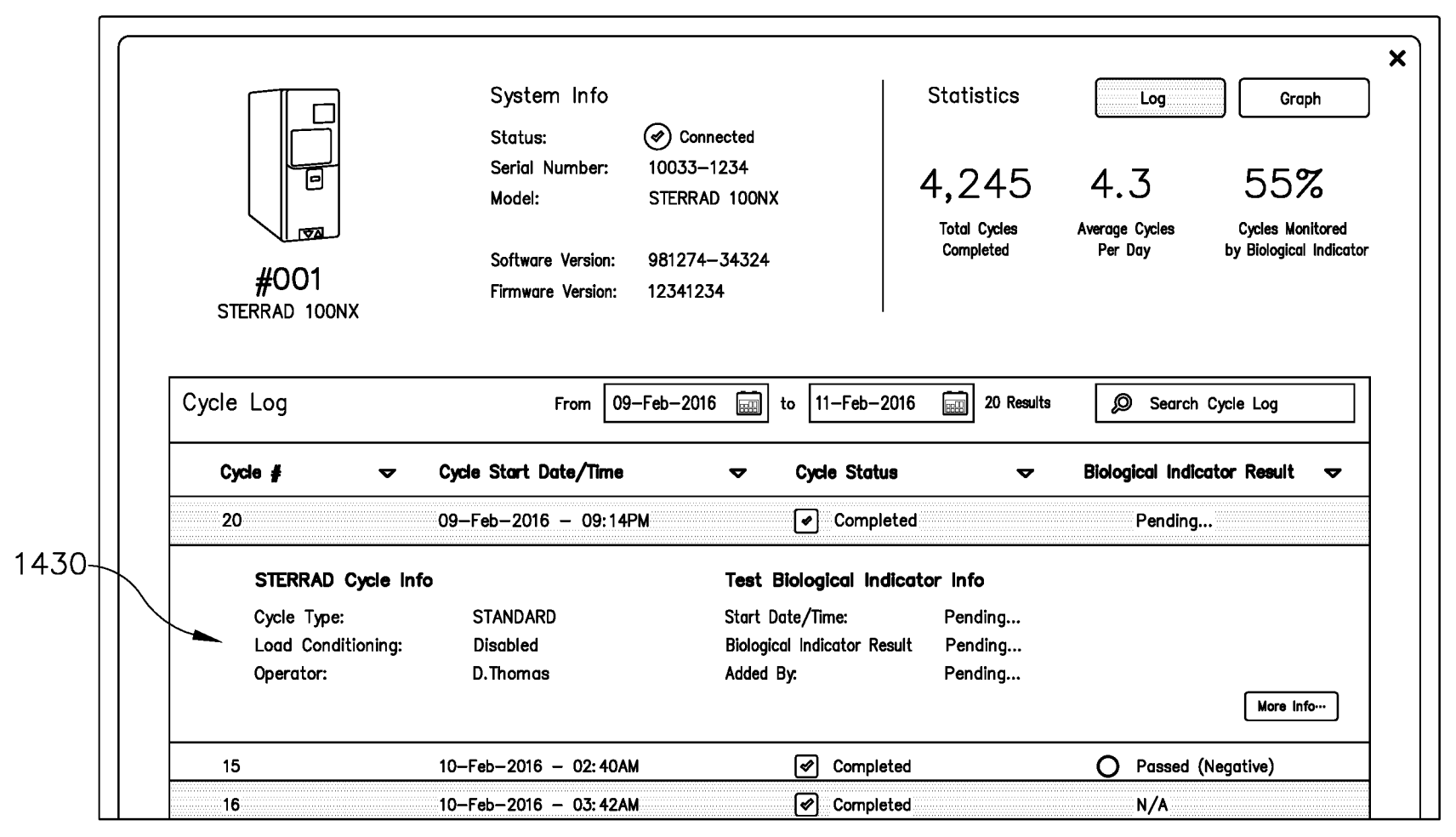

FIG. 47 shows an interface similar to that of FIG. 46, where the results of a particular task have been expanded to show additional information (1430) relating to that cycle, which may include, for example, cycle type, load conditioning, cycle operator, start time, indicator result, and indicator operator. FIG. 47 may be shown as part of displaying (block 1634) task detail for a particular task or cycle. FIG. 48 shows an additional interface that may be displayed to a user as part of displaying (block 1634) task detail for a particular task. An interface such as that of FIG. 48 may show such information as a cycle information window (1432) having such information as cycle status, device identifier, cycle identifier, cycle type, load conditioning, cycle operator, cycle date, start time, end time, duration of cycle, facility name, department name, sterilization cassette lot number, biological indicator status, and manually entered cycle notes. Information shown may also include a biological indicator window (1434), that may show such information as indicator result, indicator reader used, indicator type, indicator lot number, indicator serial number, indicator expiration date, indicator operator, indicator entry time, indicator entry date, indicator result time, indicator color change, and incubation temperature.

Another exemplary interface may be shown as part of displaying (block 1634) task detail for a particular cycle or device, which may include information such as maximum and minimum values for various physical attributes of sterilizing cabinet (100, 150) such as chamber, vapor, and conditioning pressure and temperature, delivered power, plasma time, and other attributes.

Figure 49:
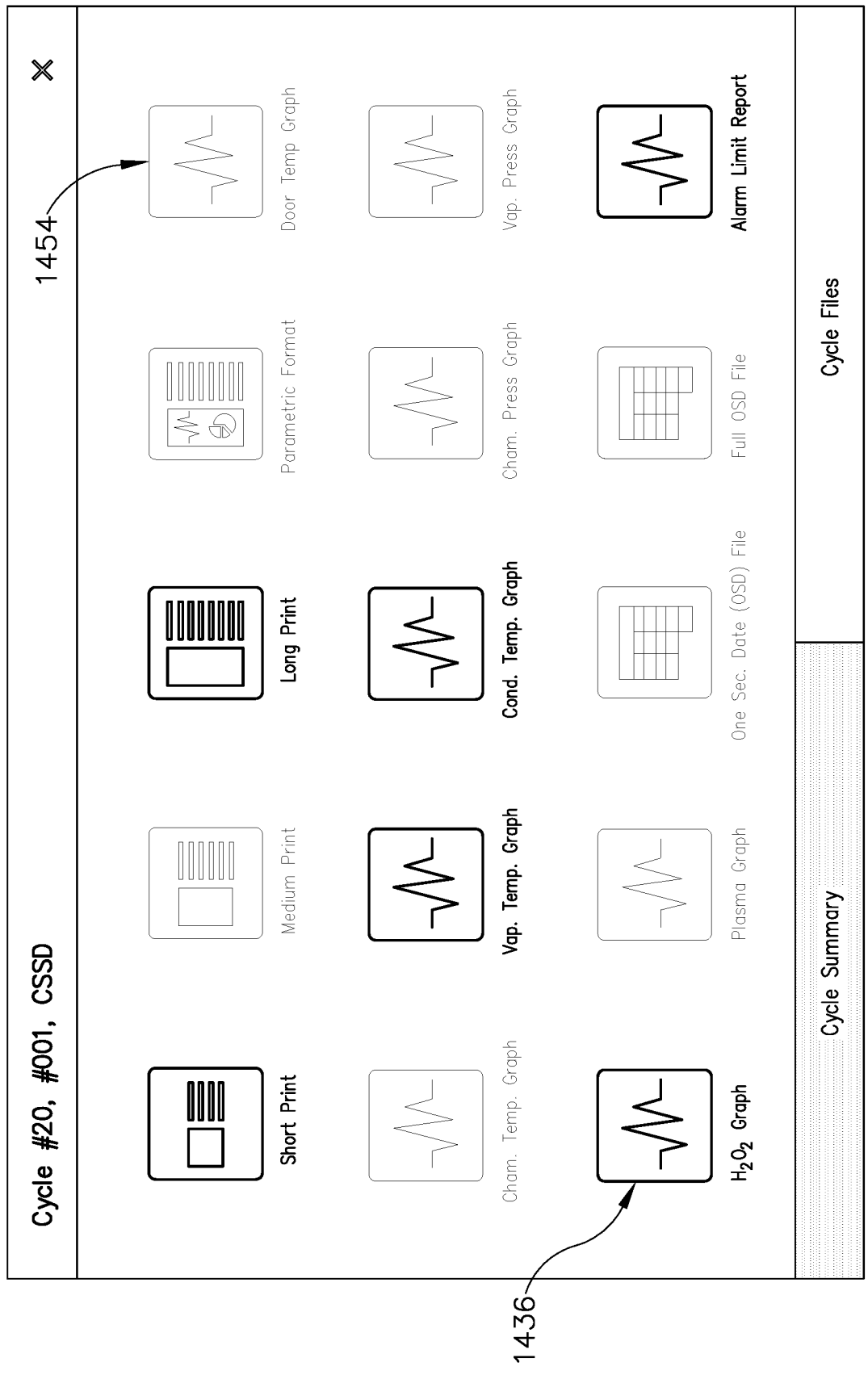
FIG. 49 shows an example of an interface that may be used to select to view information from a medical device processing component in one or more forms via a user device coupled with the communication hub of FIG. 39 or directly via the communication hub of FIG. 40.
Figure 55:
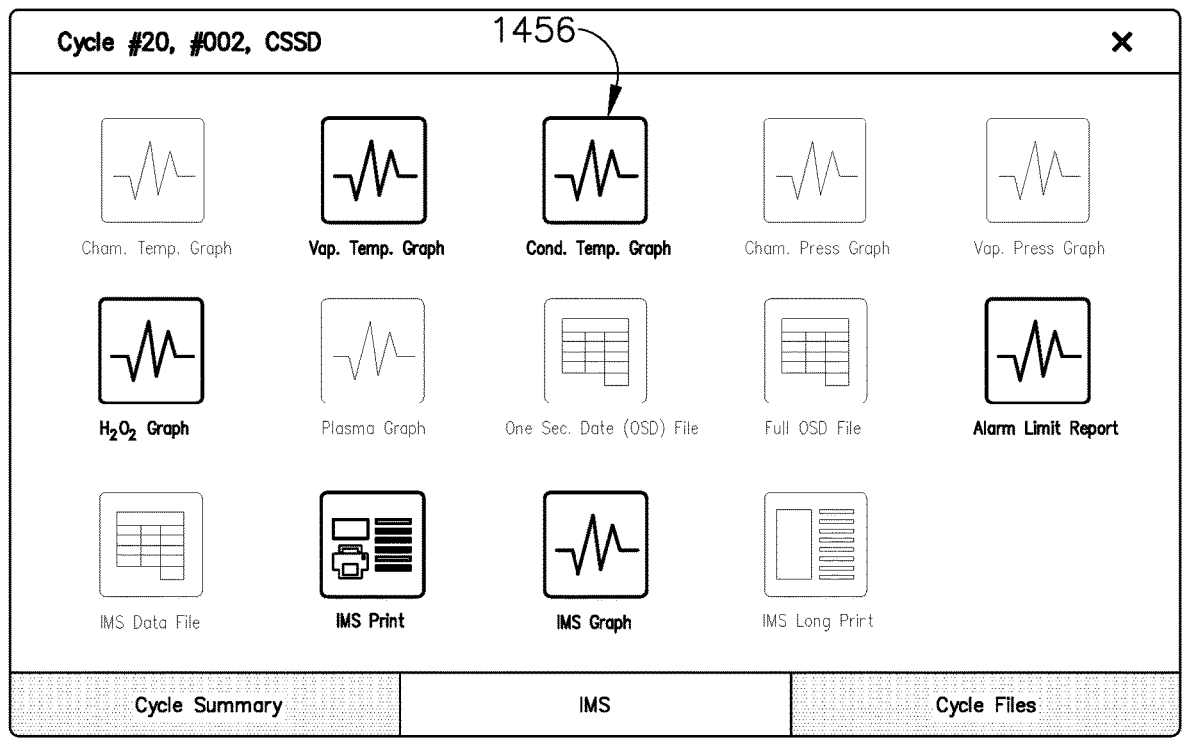
FIG. 55 shows an example of an interface that may be used to select to view information from a medical device processing component in one or more graphical views via a user device coupled with the communication hub of FIG. 39 or directly via the communication hub of FIG. 40.

FIG. 49 shows an interface that may be shown as part of displaying (block 1638) a task or activity graph selection for a selected component (100, 102, 104, 150, 800). In such an interface, some icons may be solid (1436) indicating that they are available for the selected component (100, 102, 104, 150, 800); while others may be greyed out or semi-translucent (1454) indicating that they are unavailable for the selected component (100, 102, 104, 150, 800). For example, one type of sterilizing cabinet (100) may generate information during a sterilization cycle which can be viewed in an $H_2O_2$ graph (1436), but may not generate information which can be viewed in a door temperature graph (1454). FIG. 55 shows an interface that may be displayed for a different type of sterilizing cabinet (100), which supports some additional visualization options such a load conditioning temperature graph (1456).

Visualizations options may vary depending upon the particular device selected, but may include information relating to the device or a cycle of the device as a short printable view, medium printable view, long printable view, parametric format view, door temperature graph, sterilization chamber graph, vapor temperature graph, conditioning temperature graph, chamber pressure graph, vapor pressure graph, $H_2O_2$ graph, plasma graph, partial or complete one second data file, alarm limit report view, indicator data file, indicator printable view, indicator graphs, indicator long printable view, and other views and visualizations that may be desirable.

Figure 50:
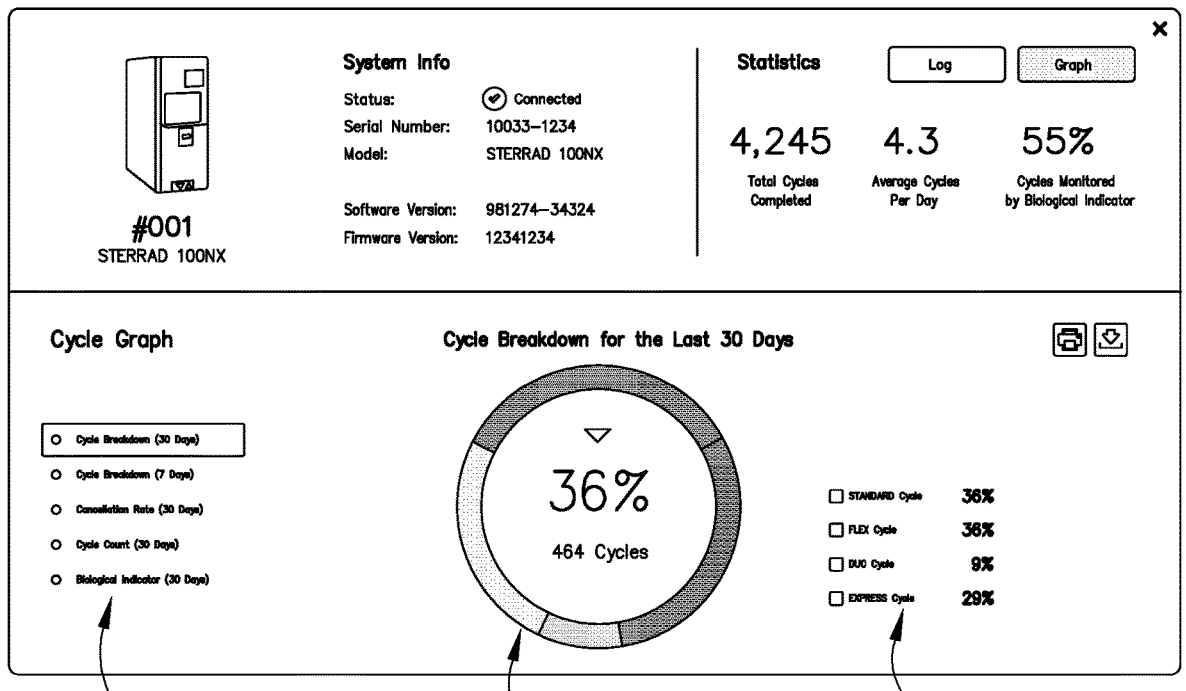
FIG. 50 shows an example of an interface that may be used to view information from a medical device processing component in a graphical form via a user device coupled with the communication hub of FIG. 39 or directly via the communication hub of FIG. 40.

FIG. 50 shows an interface that may be shown as part of displaying (block 1638) a task or activity graph for a component (100, 102, 104, 150, 800). A graph type selection (1438) may be interacted with by a user to select to see information graphed as, for example, a 30-day cycle breakdown, a 7-day cycle breakdown, a 30-day cycle cancellation rate, a 30-day cycle count, a 30-day biological indicator usage, and other graphs as may be desirable for a sterilizing cabinet (100) or indicator analyzer (102). Also included may be a graphical visualization (1440) such as a chart, graph, table, or other data model that may include one or more visible data indicators such as size, shape, color, numbers, and arrangement, and a visualization key (1442) providing further explanation for graphical visualization (1440) including an indication of what visible data indicators represent.

Figure 51:
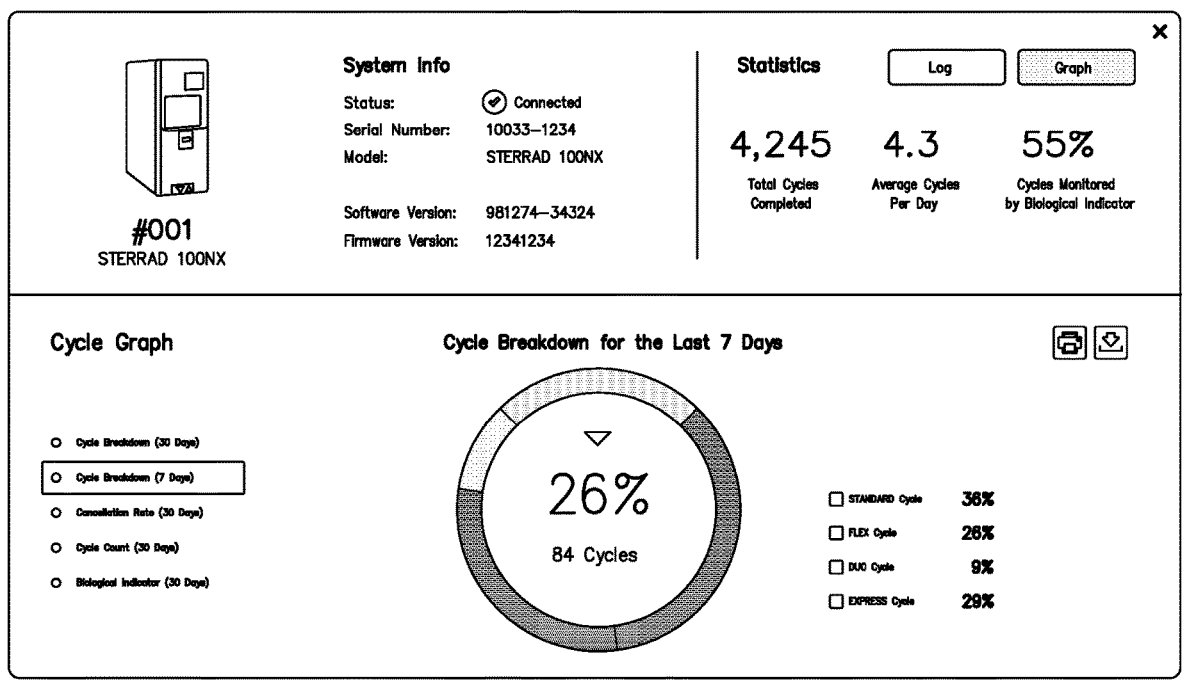
FIG. 51 shows an example of an interface that may be used to view information from a medical device processing component in an alternate graphical form via a user device coupled with the communication hub of FIG. 39 or directly via the communication hub of FIG. 40.
Figure 52:
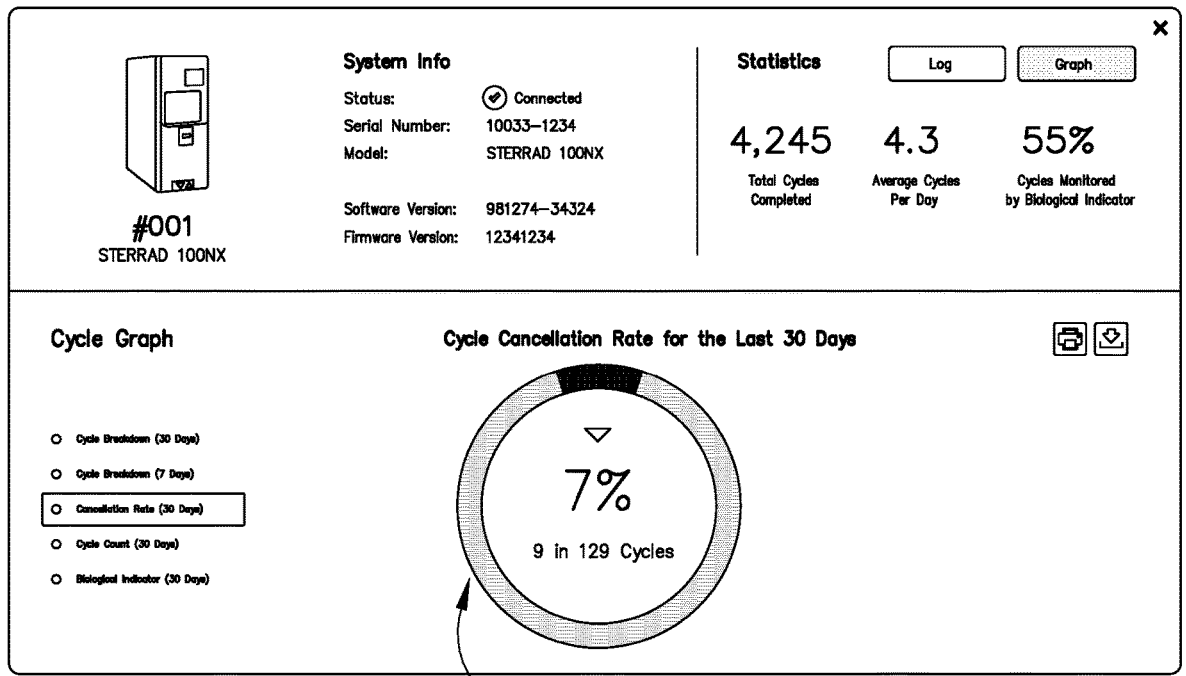
FIG. 52 shows an example of an interface that may be used to view failed task information from a medical device processing component in a graphical form via a user device coupled with the communication hub of FIG. 39 or directly via the communication hub of FIG. 40.
Figure 53:
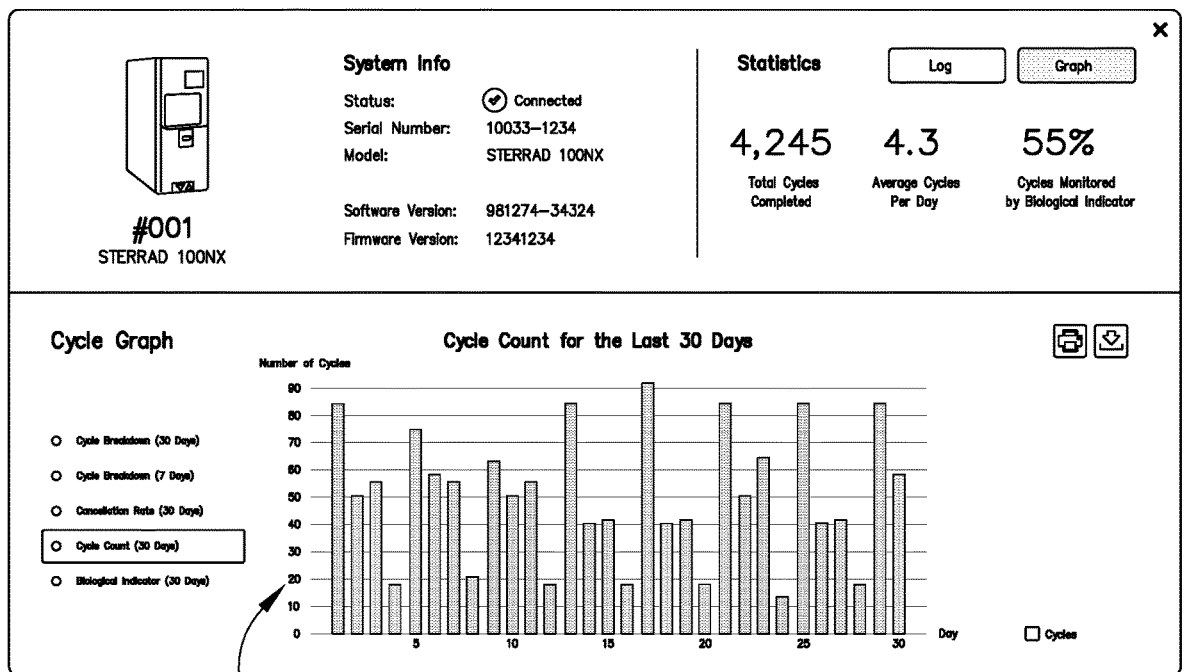
FIG. 53 shows an example of an interface that may be used to view information from a medical device processing component in yet another alternate graphical form via a user device coupled with the communication hub of FIG. 39 or directly via the communication hub of FIG. 40.
Figure 54:
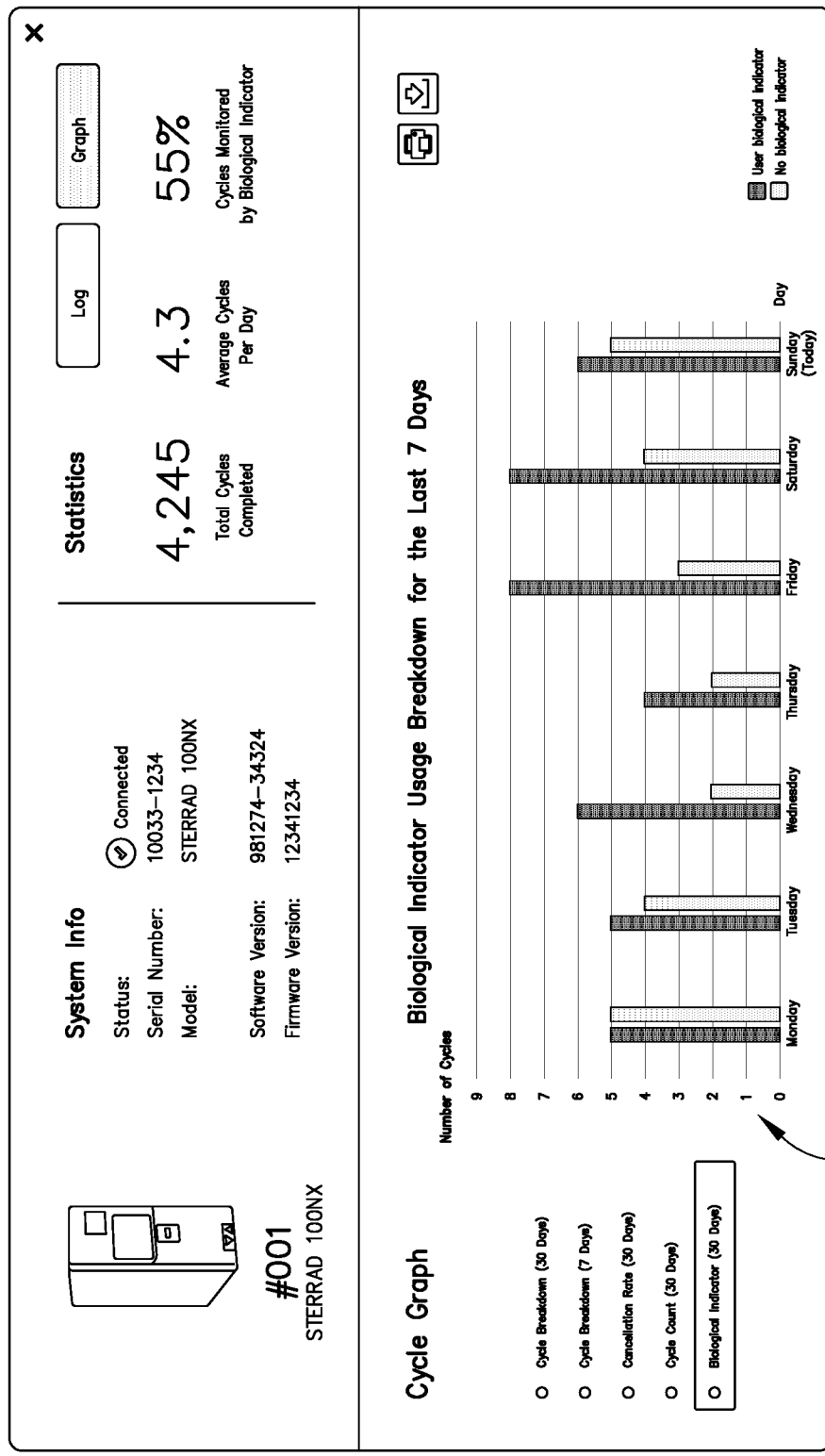
FIG. 54 shows an example of an interface that may be used to view information from a medical device processing component in yet another alternate graphical form via a user device coupled with the communication hub of FIG. 39 or directly via the communication hub of FIG. 40.

FIG. 51 shows an interface similar to that of FIG. 50, which may be shown after a user has selected to view a different cycle breakdown, such as the 7-day cycle breakdown instead of the 30-day cycle breakdown. FIG. 52 shows an interface similar to that of FIG. 50, which may be shown after a user has selected to view a cycle cancellation rate, and which may include a cancellation graph (1444) or other visualization showing a number of percentage of cycles which have been canceled or otherwise failed over the selected time period. FIG. 53 shows an interface similar to that of FIG. 50, which visualizes data as a bar chart (1446) instead of a pie chart. FIG. 54 shows an interface to that of FIG. 53, which visualizes data as a bar chart (1448) including two variables, one for cycles in which a biological indicator was used, and one for cycles which did not use a biological indicator.

Figure 56:
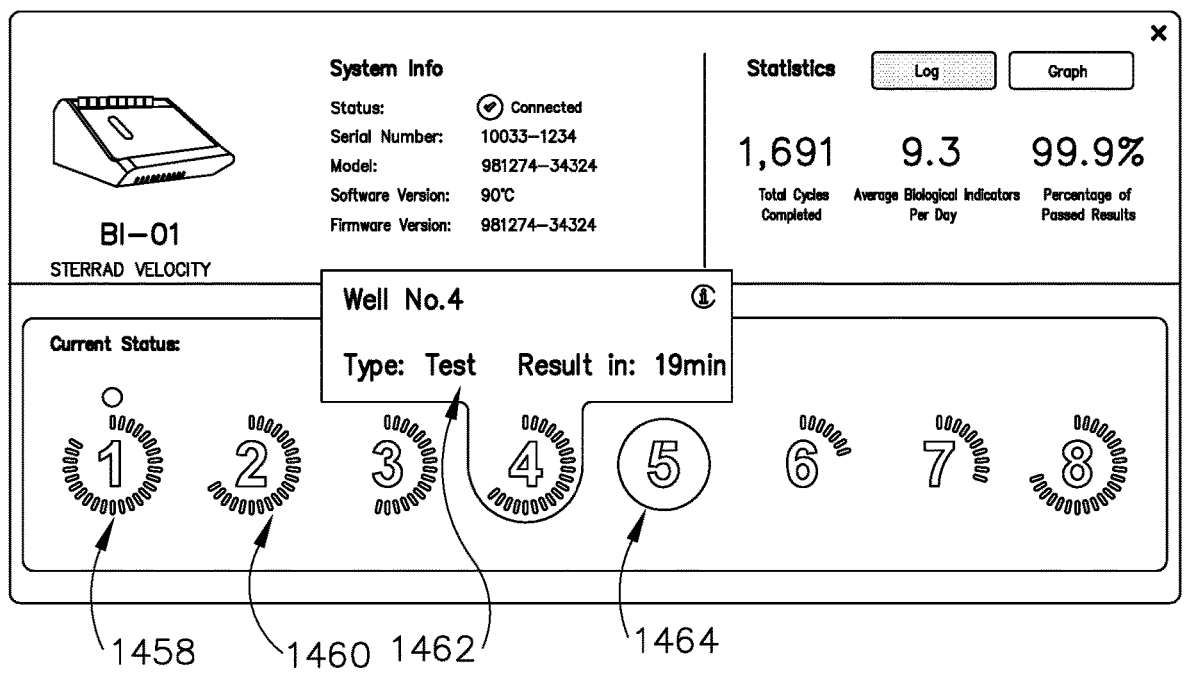
FIG. 56 shows an example of an interface that may be used to view and manage an indicator analyzer's tasks and information via a user device coupled with the communication hub of FIG. 39 or directly via the communication hub of FIG. 40.

FIG. 56 shows an interface that may be shown as part of displaying (block 1630) a task or device overview or summary which shows additional status information for the selected device. FIG. 56 shows a status overview for an indicator analyzer (102, 800) that indicates whether each indicator well (810) is in use or not. While FIG. 56 shows such features specific to a biological indicator, it should be apparent that such principles may also be applied to other processing components (100, 102, 104, 150, 800) such as a sterilizing cabinet (100). An interface such as that shown in FIG. 56 may include an indicator well identifier (1458), an indicator well progress indicator (1460), an indicator well type (1462) and result for a selected indicator well (810), an indicator well vacant indicator (1464), and other information that may be generated by the indicator analyzer (102, 800) and displayed on a status overview interface. Similar information may be shown for a sterilization cabinet (100, 150), such as how many chambers (152) the cabinet (100, 150) has, which chambers (152) are in use, what their current temperature or pressure is, a remaining time for a currently performed cycle, and other information that may be generated by a sterilizing cabinet (100, 150) and displayed on a status overview interface.

Figure 57:
FIG. 57 shows an example of an interface that may be used to view and manage additional information on an indicator analyzer task via a user device coupled with the communication hub of FIG. 39 or directly via the communication hub of FIG. 40.

Another interface may show a table of task details for an indicator analyzer (102, 800). Shown information may include an analysis start time, biological indicator type, biological indicator status, sterilization cycle number, sterilization cycle type, and sterilization cycle status. Also shown may be an indicator well status that indicates the status of each indicator well (810) of an indicator analyzer (102, 800). FIG. 57 shows an interface which may be shown when a user selects a particular task from the table in order to see additional information for that task or indicator analysis.

Another interface may be shown when a user selects to see a complete set of information for an indicator task and any related sterilization cycle task (1432). This interface may display information including but not limited to whether the biological indicator passed the analysis, the identity of the indicator analyzer (102, 800), the type of biological indicator, the lot number of the biological indicator, the serial number of the biological indicator, the expiration date of the biological indicator, the date and time of the biological indicator analysis, the identity of the operator who initiated the biological indicator analysis, the temperature at which the biological indicator analysis was carried out, the identity of the sterilizing cabinet (100, 150) in which the biological indicator encountered a sterilization cycle, the associated sterilization cycle number, the type of associated sterilization cycle, the identity of the operator of the associated sterilizing cabinet (100, 150), the time and location of the associated sterilization cycle, etc.

Another interface may be shown as part of displaying (block 1630) a task or device overview, specifically, when there is a history of notifications for the task or component (100, 102, 104, 150, 800). Such an interface may show a notification table having a notification type, which may include notification types such as cancelled cycle, failed (positive) biological indicator, passed (negative) biological indicator, and other notifications. Such a table may additionally show a details column which may provide details relating to the notification, such as any error messages or status reports generated as part of the notification.

Another interface may be shown as part of displaying (block 1630) a task or device overview, specifically, when there may be user entered notes associated with the component (100, 102, 104, 150, 800) or task. Information shown may include a date of note entry, note author, and note text. An interface may be shown as part of displaying (block 1630) a task or device overview for an indicator analyzer (102) that includes information on biological indicator lots. Information shown may include a lot identifier, a control result for that lot, a previous control end time, and a number of controls performed for that lot. Such an interface may be helpful in providing information to a user to identify biological indicator lots from which to select an indicator for a test, and may also aid in selecting an indicator from a let for a control so that others may use indicators from that lot for tests.

Figure 43:
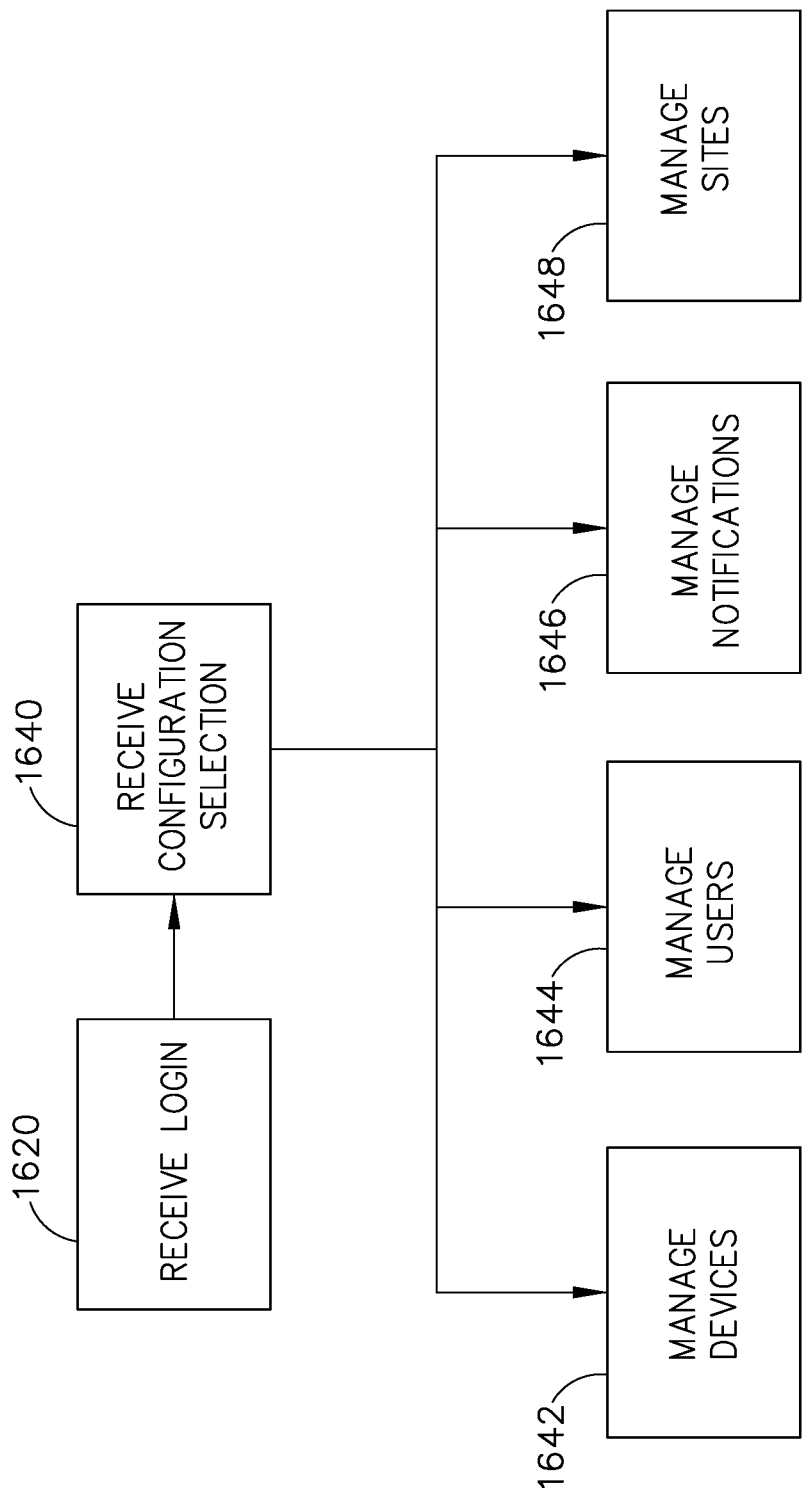
FIG. 43 shows an exemplary set of steps that may be performed using a communication hub, such as that shown in FIG. 39 or that shown in FIG. 40, to manage configurations of a network of medical device processing components.

FIG. 43 shows an exemplary set of steps that may be performed using a communication hub (20) such as that shown in FIGS. 39-40 to manage configurations of a network of processing components (100, 102, 104, 150, 800). After a login attempt is received (block 1620) and validated, one or more configuration selections may be received (block 1640) from a user of the user device (108). Received configuration selections may include selections to manage devices (block 1642) that are configured to be monitored or managed by the communication hub (20), selections to manage users (block 1644) that are configured to access or interact with the communication hub (20), selections to manage notification settings (block 1646), settings to manage sites that are monitored and managed by the communication hub (20), and other similar configurations. Managing devices (block 1642) may include adding, removing, or modifying configured devices (100, 102, 104, 150, 800), and may also include connecting to devices (100, 102, 104, 150, 800) over a network as described in FIG. 41. Managing users (block 1644) may include adding, removing, or modifying users. Managing notifications may include configuring and modifying notification settings, such as determining which users will receive certain notification types and over what method of communication they will be received. Managing sites may include adding, removing, or modifying sites, and determining what users and devices (100, 102, 104, 150, 800) are associated with sites.

Figure 58:
FIG. 58 shows an example of an interface that may be used to view and manage additional information for a medical device processing component connected to a network via a user device coupled with the communication hub of FIG. 39 or directly via the communication hub of FIG. 40.

Another interface may be shown when a user manages devices (block 1642). Information shown may include a table having one or more of a device identifier, a device category, a device department, and a device connection status. FIG. 58 shows an interface that may be shown when a user manages devices (block 1642) and selects a particular component (100, 102, 104, 150, 800) to manage, modify, or review. Shown information may include additional device information (1498) such as serial number, model number, software version, firmware version, and cycle types or other tasks supported by the component (100, 102, 104, 150, 800). Another interface may be shown when a user selects to modify a component (100, 102, 104, 150, 800). Information that is displayed and modifiable by a user interacting with such an interface may include device identifier, device category, device model, cycle types, tasks, or other features supported by the device, device department, serial number, software version, firmware version, and language.

Another interface may be shown when a user selects to disable a component (100, 102, 104, 150, 800) during device management (block 1642), requesting the user to explicitly confirm their intent to disable component (100, 102, 104, 150, 800). Another interface may also be shown when a user selects to add a component (100, 102, 104, 150, 800) during device management (block 1642). Information that is shown and modifiable by a user when adding a component (100, 102, 104, 150, 800) may include device identification, device category, device model, cycle, tasks, or features supported by the device, department, serial number, software version, firmware version, and device language. One or more pieces of device information may be automatically populated or updated by connecting the communication hub (20) to a component (100, 102, 104, 150, 800), which may then provide information over the network. Another interface may be shown to a user during device management (block 1642) when a component (100, 102, 104, 150, 800) is created but not yet connected to the communication hub (20), which may allow a user to proceed to the steps of FIG. 41 and the interfaces of FIGS. 59-60 with a single interaction.

Another interface may be shown to a user as part of user management (block 1644). Such an interface may show and allow modifications to a user information table (1510) that may include such information as first and last names of users, user types, usernames, and email addresses for one or more users that have been configured within the system.

Another interface may be shown to a user as part of site management (block 1648). Such an interface may show and allow modifications to a site information table (1512) that may include such information as customer identifier, site name, country, states, and city. An interface may be shown to a user as part of site management (block 1648). Such an interface may show information on one or more sites, and allow a user to select sites (1514) to activate or deactivate. An interface may be shown to a user as part of site management (block 1648) when a user selects to add a new site. Information that is shown and modifiable by a user may include customer identifier, site name, stress address, city, state, country, zip code, global region, cluster, biomed, phone number, and primary, secondary, and tertiary FSE.

Another interface may be shown to a user as part of notification management (block 1646). Such an interface may show a notification configuration window (1516) which allows a user to select, for each notification type, whether notifications should be generated through one or more communication types such as email, SMS, web portal, phone, or other similar communications. Another interface may be shown to a user as part of notification management (block 1646) when a user selects to view a summary of many notifications for a particular site or communication hub (20). Such an interface may show notifications from a variety of devices (100, 102, 104, 150, 800) for that site or hub (20), and information may include notification type and description (1518), origin device identifier (1520), and date and time of notification receipt (1522).

Figure 44:
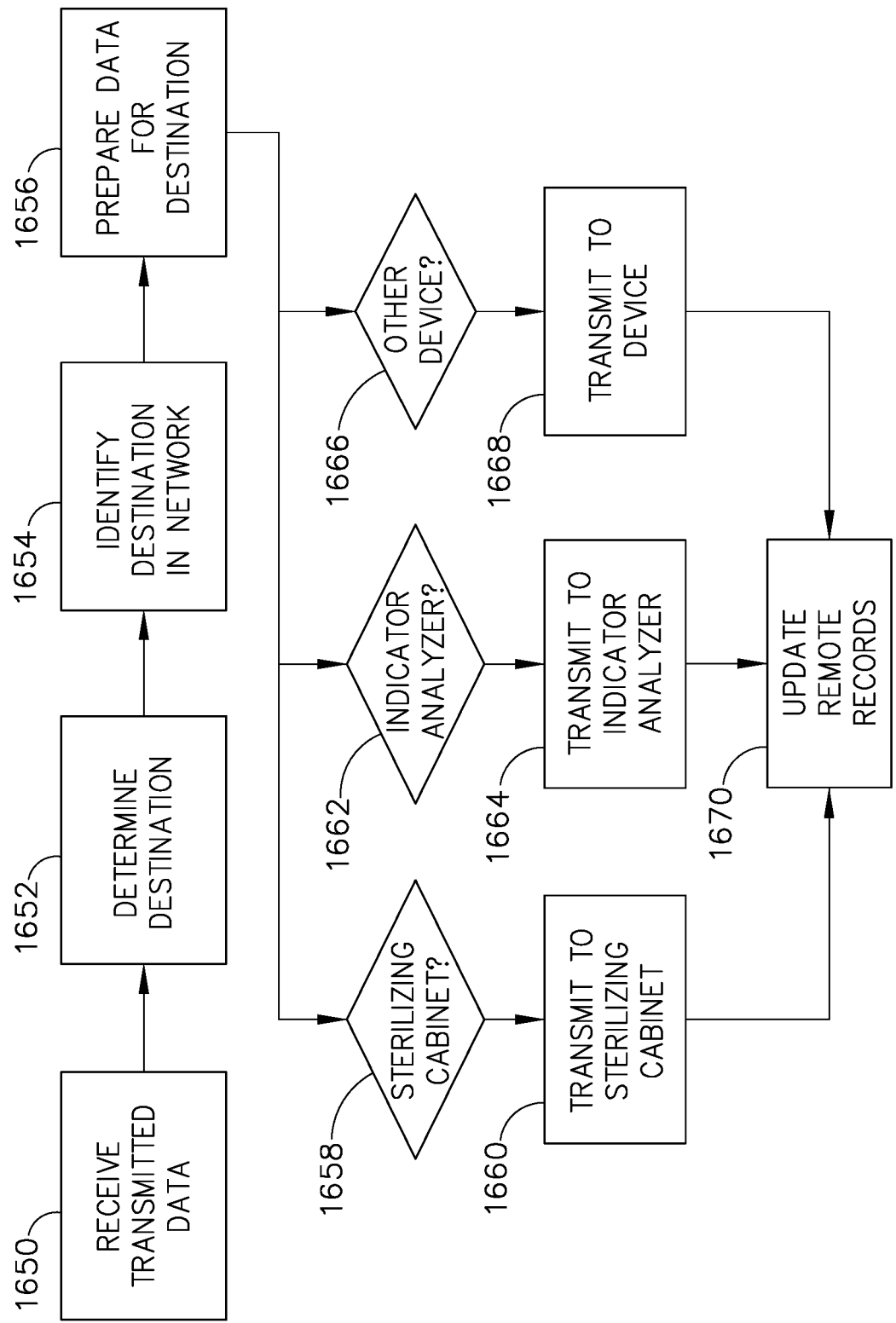
FIG. 44 shows an exemplary set of steps that may be performed using a communication hub, such as that shown in FIG. 39 or that shown in FIG. 40, to manage communications within a network of medical device processing components.

Another interface may be shown to a user as part of notification management (block 1646) when a user selects to view additional information for a single notification. Such additional information may include, for example, indicator test result, indicator test type, lot number, time indicator added, device identifier, cycle type, cycle identifier, cycle start time, and cycle end time. Additional information shown may include, for example, device last connection time, device last connection site, device current connection status, and other similar information FIG. 44 shows an exemplary set of steps that may be performed using a communication hub (20) such as that shown in FIG. 39-40 to manage communications between devices (100, 102, 104, 150, 800) of a network of processing components (100, 102, 104, 150, 800). In some cases, devices present in a network of processing components (100, 102, 104, 150, 800) may exchange information with each other through communication hub (20). As has been disclosed above in some detail, this may include situations where an indicator analyzer (102) or sterilizing cabinet (100) generates information which is passed to communication hub (20) and then accessed and displayed on a user device (108). However, this could also include a sterilizing cabinet (100) generating a record of a sterilization cycle, and transmitting that record to an indicator analyzer (102) so that a biological indicator analysis performed on the analyzer (102) may be associated with a sterilization cycle performed on the sterilizing cabinet (100). This could also include information generated by one or more devices (100, 102, 108, 150, 800) being transmitted to server (106) via the communication hub (20), such as medical records being generated at a device (100, 102, 108, 150, 800) and then sent to a server (106) for long term medical record storage. This could also include the opposite, such as software updates, firmware updates, user configurations, site configurations, device configurations, and other information being prepared on server (106) and distributed to one or more devices (100, 102, 108, 150, 800) where they can be used to update software, firmware, or configurations. Other communications and communication types enabled by a communication hub (20) connecting one or more processing components (100, 102, 104, 150, 800) will be apparent to those of ordinary skill in the art in light of the disclosure herein.

When a communication is received (block 1650) by the hub (20), it may be determined (block 1652) what the communications destination is based upon the type, form, or contents of data included in the communication. For example, if hub (20) receives a software patch bundled with data indicating it is intended for sterilization cabinets (100), the hub (20) will be able to determine the destination for the software patch. The hub (20) may also identify (block 1654) one or more destinations within its network. Following the above example, this could include identifying each sterilization cabinet (100, 150) that the hub (20) is connected to across one or more configured sites. The hub (20) may also prepare (block 1656) or modify the data in order to prepare it for transmission to the destination. This could include changing the form of the communication to a format that is expected or acceptable by the destination device, could include removing unnecessary information from the communication, such as destination identifying information which may no longer be necessary, could include encrypting the information, pairing it with authentication information, or modifying it in other ways to ensure security of the transmission to the destination, and other types of data preparation activities. The hub (20) may also then transmit data to one or more destinations depending upon whether the destination has been identified as a sterilizing cabinet (block 1658, 100), indicator analyzer (block 1662, 102), or another device (block 1666) such as a user device (108) or server (106).

If the destination is identified as one or more sterilizing cabinets (block 1658), the hub (20) may transmit the prepared data to the destination where it may be received and used to update software, update firmware, display a message via a display of the cabinet (100, 150), update one or more records stored locally on the cabinet (100, 150) such as user configurations or device configurations, or similar actions. In cases where data is sent to a sterilizing cabinet (block 1660), it may also be sent to a server (106) where a remote record of the data may be maintained (block 1670) in case of data loss or device failure. Similarly, if the target destination is determined to be one or more indicator analyzers (block 1662) or other device (block 1666), the prepared data may be sent to the analyzer (block 1664) or other device (block 1668) and also maintained as a remote record (block 1670).

VII. Exemplary Medical Device Reprocessor

Reprocessor (104) of the present example is configured to reprocess (i.e., decontaminate) medical devices (e.g., used or otherwise non-sterile medical devices) such as endoscopes. In particular, reprocessor (104) is configured to enclose an endoscope in a sealed chamber; flush the internal lumen(s) of the endoscope with detergent, water, alcohol, and/or various other liquids; spray the exterior of the endoscope with detergent, water, alcohol, and/or various other liquids; and dry the interior and exterior of the endoscope. In some instances, while the endoscope has not necessarily been sterilized, the endoscope may nevertheless be ready for use in another medical procedure after having been reprocessed through reprocessor (104).

By way of example only, reprocessor (104) may be configured and operable in accordance with at least some of the teachings of U.S. Pat. No. 6,986,736, entitled "Automated Endoscope Reprocessor Connection with Integrity Testing," issued Jan. 17, 2006, the disclosure of which is incorporated by reference herein; U.S. Pat. No. 7,479,257, entitled "Automated Endoscope Reprocessor Solution Testing," issued Jan. 20, 2009, the disclosure of which is incorporated by reference herein; U.S. Pat. No. 7,686,761, entitled "Method of Detecting Proper Connection of an Endoscope to an Endoscope Reprocessor," issued Mar. 30, 2010, the disclosure of which is incorporated by reference herein; U.S. Pat. No. 8,246,909, entitled "Automated Endoscope Reprocessor Germicide Concentration Monitoring System and Method," issued Aug. 21, 2012, the disclosure of which is incorporated by reference herein; and/or U.S. patent application Ser. No. 15/157,800, entitled "Apparatus and Method for Reprocessing a Medical Device," filed May 20, 2016, the disclosure of which is incorporated by reference herein. An example of a commercially available reprocessor (104) is the EVOTECH® Endoscope Cleaner and Reprocessor (ECR) by Advanced Sterilization Products of Irvine, Calif. Other suitable ways in which reprocessor (104) may be configured and operable will be apparent to those of ordinary skill in the art in view of the teachings herein.

It should also be understood that some medical devices (e.g., endoscopes) may be processed in reprocessor (104) without also being processed in sterilizing cabinet (100, 150). Likewise, some medical devices (e.g., endoscopes) may be processed in sterilizing cabinet (100, 150) without also being processed in reprocessor (104). The decision on whether to process a medical device such as an endoscope through sterilizing cabinet (100, 150) or reprocessor (104) may be based on the kind of endoscope at hand and/or based on the location(s) within the patient anatomy in which the endoscope is typically used.

VIII. Exemplary User Device

User device (108) may comprise a device such as a laptop computer, a desktop computer, a mobile device such as a smartphone, tablet, or other mobile computing device, or a proprietary device having similar capabilities, such capabilities including wired or wireless communication with devices such as communication hub (20), a processor and memory, a display, a user interface, and other capabilities as may be described in further detail below. User device (108) may be used to access and view information associated with one or more processing components (100, 102, 104, 150, 800) via communication hub (20), and may also be used to create or modify configurations and settings of communication hub (20) and connected devices. A user of user device (108) may view information and configure devices via, for example, a desktop software application, a mobile device software application, a web browser, or another software interface that may allow user device (108) to exchange information with communication hub (20). While only one user device (108) is shown in FIG. 1 and in FIG. 39 as being in communication with communication hub (20), it should be understood that several user devices (108) may be in communication with communication hub (20). Similarly, several sterilizing cabinets (100), several biological indicator analyzers (102), and/or several servers (106) may be in communication with communication hub (20).

IX. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system comprising: (a) a sterilizing cabinet, wherein the sterilizing cabinet includes a sterilization chamber, wherein the sterilizing cabinet is operable to sterilize a medical device disposed in the sterilization chamber; (b) a biological indicator analyzer, wherein the biological indicator analyzer is operable to detect the presence of a living organism in a biological indicator assembly; and (c) a communication hub, wherein the sterilizing cabinet is in communication with the communication hub, wherein the biological indicator analyzer is also in communication with the communication hub, wherein the communication hub is operable to transmit information from the biological indicator analyzer to the sterilizing cabinet.

Example 2

The system of Example 1, further comprising a server, wherein the server is in communication with the communication hub.

Example 3

The system of Example 2, wherein the communication hub is operable to transmit information from the biological indicator analyzer to the server.

Example 4

The system of any one or more of Examples 2 through 3, wherein the communication hub is operable to transmit information from the sterilizing cabinet to the server.

Example 5

The system of any one or more of Examples 2 through 4, wherein the communication hub is operable to transmit information from the server to the sterilizing cabinet.

Example 6

The system of any one or more of Examples 2 through 4, wherein the communication hub is operable to transmit information from the server to the biological indicator analyzer.

Example 7

A sterilizing cabinet, wherein the sterilizing cabinet includes a sterilization chamber, wherein the sterilizing cabinet is operable to sterilize a medical device disposed in the sterilization chamber, wherein the sterilizing cabinet is further operable to condition the medical device before sterilizing the medical device.

Example 8

The sterilizing cabinet of Example 7, wherein the sterilizing cabinet is operable to condition the medical device before sterilizing the medical device by detecting moisture on the medical device and removing the moisture from the medical device.

Example 9

A sterilizing cabinet, comprising: (a) a sterilization chamber, wherein the sterilizing cabinet is operable to sterilize a medical device disposed in the sterilization chamber; and (b) a reader, wherein the reader is operable read an identification tag of a biological indicator.

Example 10

The sterilizing cabinet of Example 9, wherein the reader is operable to scan an optical code on the biological indicator.

Example 11

The sterilizing cabinet of any one or more of Examples 9 through 10, further comprising a graphical user interface, wherein the graphical user interface is configured to prompt a user to operate the reader to read an identification tag of a biological indicator.

Example 12

The sterilizing cabinet of Example 11, wherein the graphical user interface is further configured to prompt a user to select a sterilization cycle from a plurality of available sterilization cycles.

Example 13

The sterilizing cabinet of Example 12, wherein the sterilizing cabinet is configured to identify a particular kind of biological indicator associated with a particular sterilization cycle selected by the user, wherein the graphical user interface is further configured to prompt a user to operate the reader to read an identification tag of the particular kind of biological indicator associated with a particular sterilization cycle selected by the user.

Example 14

A method of processing a medical device, the method comprising: (a) receiving input from a user selecting a particular sterilization cycle from a plurality of available sterilization cycles; (b) identifying a particular kind of biological indicator associated with the selected sterilization cycle; (c) prompting the user to place the medical device and the identified biological indicator into a sterilization chamber of a sterilizing cabinet; (d) performing load conditioning on the medical device in the sterilization chamber, wherein the act of performing load conditioning comprises removing moisture from the medical device; and (e) performing the selected sterilization cycle on the medical device in the sterilization chamber after completing the act of load conditioning.

Example 15

The method of Example 14, further comprising prompting the user to scan an identification tag of the identified biological indicator before prompting the user to place the medical device and the identified biological indicator into the sterilization chamber.

Example 16

The method of Example 15, further comprising evaluating a facility policy regarding use of biological indicators, wherein the act of prompting the user to scan an identification tag of the identified biological indicator is performed based on the evaluation of the facility policy regarding the user of biological indicators.

Example 17

The method of any one or more of Examples 15 through 16, wherein the sterilizing cabinet has a graphical user interface, wherein the act of prompting the user to scan an identification tag of the identified biological indicator is performed through the graphical user interface.

Example 18

The method of any one or more of Examples 14 through 17, wherein the sterilizing cabinet has a touch screen.

Example 19

The method of Example 18, wherein the input from the user selecting the particular sterilization cycle is received via the touch screen.

Example 20

The method of any one or more of Examples 18 through 19, wherein the act of prompting the user to place the medical device and the identified biological indicator into a sterilization chamber of a sterilizing cabinet is performed via the touch screen.

Example 21

The method of any one or more of Examples 18 through 20, further comprising presenting the user with information regarding each of the available sterilization cycles via the touch screen.

Example 22

The method of any one or more of Examples 18 through 21, further comprising presenting the user with information regarding the completed sterilization cycle after performing the selected sterilization cycle on the medical device, wherein the act of presenting the user with information regarding the completed sterilization cycle is performed via the touch screen.

Example 23

A method of processing a medical device, the method comprising: (a) receiving input from a user selecting a particular sterilization cycle from a plurality of available sterilization cycles; (b) identifying a particular kind of biological indicator associated with the selected sterilization cycle; (c) prompting the user to use a reader of a sterilizing cabinet to read an identification tag of the identified kind of biological indicator; (d) receiving information from the reader based on the user's use of the reader to read an identification tag of a biological indicator; (e) prompting the user to place the medical device and the identified biological indicator into a sterilization chamber of the sterilizing cabinet; and (f) performing the selected sterilization cycle on the medical device in the sterilization chamber.

Example 24

The method of Example 23, further comprising performing load conditioning on the medical device in the sterilization chamber, wherein the act of performing load conditioning comprises removing moisture from the medical device.

Example 25

The method of Example 24, wherein the act of performing the selected sterilization cycle is performed after completing the act of load conditioning.

Example 26

The method of any one or more of Examples 23 through 25, further comprising determining whether the information received from the reader indicates that the user has selected the particular kind of biological indicator associated with the selected sterilization cycle.

Example 27

The method of Example 26, wherein the act of determining indicates that the user has not selected the particular kind of biological indicator associated with the selected sterilization cycle, the method further comprising informing the user that the user has not selected the particular kind of biological indicator associated with the selected sterilization cycle.

Example 28

A method of processing a medical device, the method comprising: (a) receiving input from a user selecting a particular sterilization cycle from a plurality of available sterilization cycles; (b) identifying a particular kind of biological indicator associated with the selected sterilization cycle; (c) prompting the user to place the medical device and the identified biological indicator into a sterilization chamber of the sterilizing cabinet; (d) performing the selected sterilization cycle on the medical device in the sterilization chamber; and (e) determining whether the identified biological indicator contains any living organisms after performing the selected sterilization cycle.

Example 29

The method of Example 28, wherein the act of determining whether the identified biological indicator contains any living organisms comprises evaluating fluorescence associated with the identified biological indicator.

Example 30

The method of any one or more of Examples 28 through 29, wherein the act of determining whether the identified biological indicator contains any living organisms indicates that the identified biological indicator contains a living organism, the method further comprising informing the user that the identified biological indicator contains a living organism.

Example 31

The method of Example 30, wherein the act of informing the user that the identified biological indicator contains a living organism is performed via the sterilizing cabinet.

Example 32

The method of any one or more of Examples 28 through 31, wherein the act of determining whether the identified biological indicator contains any living organisms is performed using a biological indicator analyzer, wherein the biological indicator analyzer is separate from the sterilizing cabinet.

Example 33

A biological indicator analyzer, comprising: (a) a plurality of wells, wherein each well is configured to receive a respective biological indicator; (b) a plurality of organism detector features, wherein each organism detector feature is configured to detect whether a biological indicator disposed in a corresponding well of the plurality of wells contains a living organism; and (c) a touch screen, wherein the touch screen is configured to receive user input and provide information to the user indicating a status of biological indicator analysis.

Example 34

The biological indicator analyzer of Example 33, wherein the organism detector features comprise: (i) light sources configured to emit light toward biological indicators disposed in the wells, and (ii) sensors configured to detect fluorescence from biological indicators disposed in the wells.

Example 35

The biological indicator analyzer of any one or more of Examples 33 through 34, further comprising a communication port, wherein the communication port is configured to communicate results of biological indicator analysis to a device located remotely from the biological indicator analyzer.

Example 36

The biological indicator analyzer of any one or more of Examples 33 through 35, further comprising a plurality of indicator sensors, wherein each indicator sensor is configured to determine whether an indicator is placed in the well.

Example 37

The biological indicator analyzer of any one or more of Examples 33 through 36, further comprising a processor and a memory, wherein the processor is configured to receive a well selection and an indicator selection from a user and, in response, query a remote server to determine whether a control indicator has been tested for an indicator lot associated with the indicator selection and, where a control indicator has not been tested, display a control notification to the user via the touch screen.

Example 38

The biological indicator analyzer of Example 37, wherein the processor is further configured to detect that a control indicator has been placed in a well, incubate the control indicator, and analyze the control indicator to determine if biological contamination is present, and, where biological contamination is present, display a notification via the touch screen indicating that the control indicator test was successful and associating the control indicator with the indicator selection.

Example 39

The biological indicator analyzer of Example 38, wherein the processor is further configured to, where biological contamination is not present in the control indicator, display a notification that a second control indicator must be run from the indicator lot in a different well.

Example 40

The biological indicator analyzer of any one or more of Examples 33 through 39, further comprising a processor and a memory, wherein the processor is further configured to, in response to receiving a signal indicating that a user intends to place an indicator in a well, display a chemical indicator guide via the touch screen; wherein the chemical indicator guide is configured to display an original chemical indicator and a post-sterilization chemical indicator; wherein the processor is further configured to receive a selection from a user indicating whether the chemical indicator of the indicator matches the original chemical indicator or the post-sterilization chemical indicator.

Example 41

The biological indicator analyzer of any one or more of Examples 33 through 40, further comprising a processor and a memory, wherein the processor is further configured to, in response to receiving a signal indicating that a user intends to place an indicator in a well, display a indicator activation guide via the touch screen; wherein the indicator activation guide is configured to display a set of instructions for breaking a glass ampoule of the indicator, and mixing a chemical solution of the ampoule with the biological material; wherein the processor is further configured to receive a selection from a user indicating whether the glass ampoule is broken and whether the chemical solution has been mixed.

Example 42

The biological indicator analyzer of any one or more of Examples 33 through 41, further comprising a processor and a memory, wherein the processor is configured to drive a display a graphical representation of each well via the touch screen, wherein the graphical representation is configured to indicate whether an indicator is present in the well, the time remaining for a test being performed on an indicator in a well, and whether a test being performed in a well was a success or failure.

Example 43

The biological indicator analyzer of any one or more of Examples 33 through 42, further comprising a processor and a memory, wherein the processor is configured to, in response to a failed indicator test, receive an identification from a user of the indicator analyzer, receive an acknowledgment of the failure from the user, display a set of quarantine instructions to the user via the touch screen, access a remote server in order to identify one or more surgical instruments associated with the failed indicator, and generate a notification comprising a description of the one or more surgical instruments associated with the failed indicator.

Example 44

A processing component network comprising: (a) a communication hub comprising: (i) a processor, (ii) a memory, and (iii) a network interface; (b) a set of medical device processing components; and (c) a user device; wherein the processor is configured to execute instructions to cause the communication hub to: (i) receive a first set of device configurations from the user device, (ii) create a device record for a first medical device processing component of the set of medical device processing components based upon the first set of device configurations, (iii) establish a network connection to the first medical device processing component via the network interface, (iv) provide a first set of device information to the user device, wherein the first set of device information is received from the first medical device processing component, and (v) provide a task record to a second medical device processing component of the set of medical device processing components, wherein the task record describes a first task performed by the first medical device processing component; wherein the first set of device information is configured to cause the user device to display at least a portion of the first set of device information via a display of the user device, and wherein the task record is required by the second medical device processing component in order to perform a second task.

Example 45

The processing component network of Example 44, wherein the first medical device processing component comprises a sterilization chamber; wherein the second medical device processing component comprises a biological indicator analyzer; wherein the first task comprises a sterilization cycle performed in the sterilization chamber; and wherein the second task comprises an analysis of a biological indicator used in the first task.

Example 46

The processing component network of any one or more of Examples 44 through 45, wherein the network interface comprises a Wi-Fi transceiver; wherein the user device is selected from the group consisting of: a smartphone, a computer, a tablet, and a laptop; wherein the first set of device configurations comprises: (i) a site configuration, (ii) a device configuration, and (iii) a user configuration; wherein the first set of device information comprises five or more of: (i) a cycle identifier (ii) a device identifier, (iii) a cycle status, (iv) a biological indicator result, (v) a number of total cycles, (vi) a number of average cycles per day, (vii) a number of cycles including a biological indicator, (viii) a number of completed cycles, (ix) a number of total indicator analyses, (x) a number of indicator analyses per day, (xi) a number of indicators having a pass result, (xii) an indicator analyzer well status, (xiii) a biological indicator identifier, (xiv) a biological indicator lot number, and (xv) a biological indicator color change.

Example 47

The processing component network of any one or more of Examples 44 through 46, wherein the instructions to cause the communication hub to create a device record comprise instructions to: (i) determine a device identifier, a device model, and a device serial number based upon the first set of device configurations, (ii) associate the first medical device processing component with a site, wherein the site is associated with a geographic location, and (iii) associate a user with the site; and wherein the communication hub is further configured to only provide the first set of device information to the user device when the user device is associated with the user that is associated with the site.

Example 48

The processing component network of Example 47, wherein the processor is further configured to execute instructions to cause the communication hub to: (i) receive a notification from the first medical device processing component, (ii) determine a set of users that are associated with the site, the set of users including the user, and (iii) provide the notification to a set of user devices that are associated with the set of users.

Example 49

The processing component network of any one or more of Examples 44 through 48, wherein the instructions to cause the communication hub to establish a connection to the first medical device processing component comprise instructions to: (i) receive a device connection request from the user device, (ii) provide a connection interface to the user device, (iii) receive a set of device connection information from the user device, the set of device connection information received via the connection interface, and (iv) attempt a connection to the first medical device processing component using the set of device connection information; wherein the connection interface comprises a set of connection instructions.

Example 50

The processing component network of Example 49, wherein the connection interface is configured to receive, from the user device: (i) a network location identifier, a username, and a password, or (ii) a network pairing code.

Example 51

The processing component network of any one or more of Examples 44 through 50, wherein the first medical device processing component comprises a sterilizing cabinet, and wherein the instructions to provide the set of device information comprise instructions to provide a device overview interface to the user device, wherein the device overview interface comprises two or more of: (i) a device identifier, (ii) a sterilization cycle summary, (iii) a sterilization cycle table, or (iv) a sterilization cycle visualization.

Example 52

The processing component network of Example 51, wherein the sterilization cycle summary comprises a total number of cycles, an average cycles per day, and a number of cycles including a biological indicator; wherein the sterilization cycle table comprises a set of rows, each row corresponding to a single sterilization cycle performed by the sterilizing cabinet; and wherein the sterilization cycle visualization comprises one or more of a pie chart, a bar chart, or a graph.

Example 53

The processing component network of any one or more of Examples 44 through 52, wherein the first medical device processing component comprises a biological indicator analyzer, and wherein the instructions to provide the set of device information comprise instructions to provide a device overview interface to the user device, wherein the device overview interface comprises two or more of: (i) a device identifier, (ii) a biological indicator analysis summary, (iii) an indicator well status, or (iv) an indicator analysis table.

Example 54

The processing component network of Example 53, wherein the biological indicator analysis summary comprises a total number of analyses, a number of analyses per day, and a number of analyses indicating cycle success; wherein the indicator well status comprises a plurality of well indicators, each well descriptor comprising a vacancy indicator and an analyses duration indicator; and wherein the indicator analysis table comprises a set of rows, each row corresponding to a single biological indicator analysis performed by the biological indicator analyzer.

Example 55

A method for monitoring and managing a network of medical device processing components comprising the steps: (a) creating a site record; (b) creating a device record for a first medical device processing component and associating the device record with the site record; (c) connecting the first medical device processing component to a communication hub via a network interface of the communication hub; (d) receiving a site selection identifying the site record from a user device and, in response, providing a list of devices associated with the site record to the user device; (e) receiving a device selection identifying the device record from the user device and, in response, providing a set of device information associated with the first medical device processing component to the user device; (f) receiving, at the communication hub, a task record from the first medical device processing component, the task record describing a first task performed by the first medical device processing component; and (g) providing the task record to a second medical device processing component, wherein the second medical device processing component is configured to perform a second a second task based upon the task record.

Example 56

The method of Example 55, wherein the act of connecting the first medical device processing component to the communication hub comprises: (i) receiving a device connection request from the user device, (ii) causing the user device to display a connection interface, (iii) receiving a set of device connection information from the user device, and (iv) attempting a connection to the first medical device processing component using the set of device connection information; and wherein the connection interface comprises a set of connection instructions.

Example 57

The method of Example 56, wherein the connection interface is configured to provide to the communication hub: (i) a network location identifier, a username, and a password, or (ii) a network pairing code.

Example 58

The method of any one or more of Examples 55 through 57, wherein the first medical device processing component comprises a sterilizing cabinet, wherein providing the set of device information comprises causing a device overview interface to display on the user device, wherein the device overview interface comprises two or more of: (i) a device identifier, (ii) a sterilization cycle summary, (iii) a sterilization cycle table, and (iv) a sterilization cycle visualization.

Example 59

The method of Example 58, wherein the sterilization cycle summary comprises a total number of cycles, an average cycles per day, and a number cycles including a biological indicator; wherein the sterilization cycle table comprises a set of rows, each row corresponding to a single sterilization cycle performed by the first medical device processing component; and wherein the sterilization cycle visualization comprises one or more of a pie chart, a bar chart, or a graph.

Example 60

The method of any one or more of Examples 55 through 59, wherein the first medical device processing component comprises a biological indicator analyzer; wherein providing the set of device information comprises causing a device overview interface to display on the user device; wherein the device overview interface comprises two or more of: (i) a device identifier, (ii) a biological indicator analysis summary, (iii) an indicator well status, and (iv) an indicator analysis table.

Example 61

The method of Example 60, wherein the biological indicator analysis summary comprises a total number of analyses, a number of analyses per day, and a number of analyses indicating cycle success; wherein the indicator well status comprises a plurality of well indicators, each well descriptor comprising a vacancy indicator and an analyses duration indicator; and wherein the indicator analysis table comprises a set of rows, each row corresponding to a single biological indicator analysis performed by the indicator analyzer.

Example 62

A processing component network comprising: (a) a set of medical device processing components comprising: (i) a sterilizing cabinet, and (ii) a biological indicator analyzer; and (b) a means for configuring a network and monitoring medical device processing components; wherein the means for monitoring the set of medical device processing components is configured to: (i) connect to the set of medical device processing components, and (ii) display a set of device information generated by at least one device of the set of medical device processing components.

Example 63

The processing component network of Example 62, further comprising a means for providing communication between the set of medical device processing components.

Example 64

A method of processing a medical device, the method comprising: (a) receiving input from a user selecting a sterilization cycle from a plurality of available sterilization cycles; (b) identifying a biological indicator associated with the selected sterilization cycle; (c) prompting the user via a touch screen display to place the medical device and the biological indicator into a sterilization chamber of a sterilizing cabinet; (d) performing load conditioning on the medical device in the sterilization chamber; and (e) performing the selected sterilization cycle on the medical device in the sterilization chamber after completing the act of load conditioning.

Example 65

The method of Example 64, further comprising presenting the user with information regarding each of the available sterilization cycles via the touch screen.

Example 66

The method of any one or more of Examples 64 through 65, further comprising receiving an indicator data set from a reader of the sterilizing cabinet based on the user's use of the reader to read an identification tag of the biological indicator.

Example 67

The method of Example 66, wherein the indicator data set comprises an indicator type, further comprising restricting the plurality of available sterilization cycles based upon the indicator type.

Example 68

The method of any one or more of Examples 66 through 67, wherein the indicator data set comprises an indicator expiration date, the method further comprising prompting the user to obtain a new biological indicator when the indicator expiration date indicates that the biological indicator has expired.

Example 69

The method of any one or more of Examples 66 through 68, wherein the indicator data set comprises an indicator recall status, the method further comprising prompting the user to obtain a new biological indicator when the indicator recall status indicates that the biological indicator has been recalled by a provider.

Example 70

The method of any one or more of Examples 66 through 69, wherein the indicator data set comprises an indicator source, the method further comprising prompting the user to obtain a new biological indicator when the indicator source is not within a set of approved indicator sources.

Example 71

The method of any one or more of Examples 64 through 70, further comprising prompting the user via the touch screen display to use a reader of the sterilizing cabinet to read an identification tag of the biological indicator.

Example 72

The method of Example 71, further comprising displaying a soft indicator requirement on the touch screen display when: (i) the sterilizing cabinet has not read the identification tag of the biological indicator, and (ii) the sterilizing cabinet has received an indication from the user that the sterilization cycle should begin.

Example 73

The method of any one or more of Examples 71 through 72, further comprising displaying a hard indicator requirement on the touch screen display when: (i) the sterilizing cabinet has not read the identification tag of the biological indicator, and (ii) the sterilizing cabinet has received an indication from the user that the sterilization cycle should begin, wherein the hard indicator requirement prevents the sterilization cycle from being performed.

Example 74

The method of Example 73, further comprising removing the hard indicator requirement when: (i) the sterilizing cabinet reads the identification tag of the biological indicator, or (ii) the sterilizing cabinet receives a bypass code from the user.

Example 75

The method of any one or more of Examples 64 through 74, further comprising displaying via the touch screen display a load placement image, wherein the load placement image comprises: (i) a location for one or more surgical instruments, and (ii) a location for the biological indicator.

Example 76

The method of any one or more of Examples 64 through 75, wherein the act of performing load conditioning comprises one or more of: (i) removing moisture from the medical device, and (ii) raising the temperature within the sterilizing chamber.

Example 77

The method of any one or more of Examples 64 through 76, further comprising:
(a) receiving a set of placement data from a placement sensor of the sterilizing cabinet, wherein the set of placement data indicates the location of the medical device and the biological indicator; and (b) determining whether to perform the sterilization cycle based upon the set of placement data.

Example 78

A sterilizing cabinet for sterilizing a medical device comprising a processor, a sterilization chamber, and a touch screen display, wherein the processor is configured to execute instructions to: (a) display a set of sterilization cycles; (b) receive a sterilization cycle selection; (c) display a biological indicator type based upon the sterilization cycle selection, wherein the biological indicator type indicates a biological indicator associated with the sterilization cycle selection; (d) display a set of placement instructions, wherein the set of placement instructions comprises a location for the medical device and a location for a biological indicator; (e) perform a load conditioning process on the medical device in the sterilization chamber; and (f) perform a sterilization cycle on the medical device in the sterilization chamber based upon the sterilization cycle selection.

Example 79

The sterilizing cabinet of Example 78, further comprising a reader, wherein the processor is further configured to receive an indicator data set from the reader when a user uses the reader to read an identification tag of the biological indicator.

Example 80

The sterilizing cabinet of Example 79, wherein the indicator data set comprises an indicator expiration date, wherein the processor is further configured to execute instructions to display information indicating that the biological indicator has expired when the indicator expiration date indicates that the biological indicator has expired.

Example 81

The sterilizing cabinet of any one or more of Examples 79 through 80, wherein the indicator data set comprises an indicator recall status, wherein the processor is further configured to execute instructions to display information indicating that the biological indicator is defective when the indicator recall status indicates that the biological indicator has been recalled by a provider.

Example 82

The sterilizing cabinet of any one or more of Examples 79 through 81, wherein the indicator data set comprises an indicator source, wherein the processor is further configured to execute instructions to display information indicating that the biological indicator is incompatible when the indicator source is not within a set of approved indicator sources.

Example 83

A sterilizing cabinet comprising: (a) a sterilization chamber; (b) a touch screen display; (c) a biological indicator reader; and (d) a means for guiding a user through the process of selecting a sterilization cycle, selecting a verified biological indicator, placing a medical device in the sterilization chamber, placing the biological indicator in the sterilization chamber, and initiating the sterilization cycle.

Example 84

A method for analyzing a biological indicator with an indicator analyzer, the method comprising: (a) presenting instructions to a user via a touch screen of the indicator analyzer; (b) receiving a biological indicator in a well selected from a plurality of wells in the indicator analyzer;

(c) analyzing the biological indicator in the selected well, wherein the act of analyzing comprises evaluating fluorescence associated with the biological indicator in the selected well; (d) displaying results of the analysis via the touch screen; and (e) if the results of the analysis indicate that the biological indicator is not sterile, initiating a quarantine procedure.

Example 85

The method of Example 84, wherein verifying the control status of a biological indicator analysis comprises: (i) identifying a lot associated with the biological indicator, (ii) determining whether a control has been performed on the lot, and (iii) if the control has not been performed on the lot, then perform the following: (A) display an instruction for a user to place a control indicator in a well of the biological indicator analyzer, (B) perform a control analysis on the control, (C) if the control analysis fails the first time, then display an instruction for the user to repeat verifying the control status of the biological indicator using a different well, and (D) if the control analysis fails for the second time, then display an instruction for the user to repeat verifying the control status of the biological indicator using a different lot.

Example 86

The method of any one or more of Examples 84 through 85, wherein performing the biological indicator analysis comprises: (i) displaying an instruction for a user to verify that the biological indicator has undergone a sterilization cycle, (ii) displaying an instruction for a user to verify chemical activation of the biological indicator, (iii) determining whether the biological indicator has been placed in a well of the indicator analyzer, (iv) incubating the biological indicator, (v) emitting light towards the biological indicator from a light source of the indicator analyzer, and (vi) detecting fluorescence from the biological indicator using a sensor of the indicator analyzer.

Example 87

The method of any one or more of Examples 84 through 86, wherein the quarantine procedure comprises: (i) identifying a set of potentially contaminated medical devices, and (ii) for each potentially contaminated medical device of the set of the potentially contaminated medical devices, provide a notification to a responsible party for that potentially contaminated medical device.

Example 88

The method of claim 84, further comprising: (a) displaying an instruction for a user to scan the biological indicator using an indicator scanner of the indicator analyzer; (b) receiving an indicator identification from the biological indicator; and (c) determining an indicator data set based upon the indicator identification, wherein the indicator data set comprises a unique identifier and an indicator history.

Example 89

A method for analyzing a biological indicator with an indicator analyzer, the method comprising: (a) verifying a control status of a biological indicator analysis by: (i) identifying a lot associated with the biological indicator, (ii) determining whether a control has been performed on the lot, and (iii) if the control has not been performed on the lot, the performing the following: (A) display an instruction for a user to place a control indicator in a well of the biological indicator analyzer, (B) perform a control analysis on the control, (C) if the control analysis fails the first time, then display an instruction for the user to repeat verifying the control status of the biological indicator using a different well, and (D) if the control analysis fails for the second time, then display an instruction for the user to repeat verifying the control status of the biological indicator using a different lot; (b) performing the biological indicator analysis by: (i) displaying an instruction for a user to verify that the biological indicator has undergone a sterilization cycle, (ii) displaying an instruction for a user to verify chemical activation of the biological indicator, (iii) determining whether the biological indicator has been placed in a well of the indicator analyzer, (iv) incubating the biological indicator, (v) emitting light toward the biological indicator from a light source of the indicator analyzer, and (vi) detecting fluorescence from the biological indicator using a sensor of the indicator analyzer; (c) distributing results of the biological indicator analysis; and (d) if the results of the biological indicator analysis indicate that the biological indicator is not sterile, then initiating a quarantine procedure.

Example 90

A biological indicator analyzer, comprising: (a) a plurality of wells, wherein each well is configured to receive a respective biological indicator; (b) a plurality of organism detector features, wherein each organism detector feature is configured to detect whether a biological indicator disposed in a corresponding well of the plurality of wells contains a living organism; and (c) a touch screen, wherein the touch screen is configured to receive user input and provide information to the user indicating a status of biological indicator analysis.

Example 91

The biological indicator analyzer of Example 90, further comprising an indicator scanner, wherein the indicator scanner is operable to read an indicator identification from the biological indicator and determine an indicator data set based upon the indicator identification, wherein the indicator data set comprises a unique identifier and an indicator history.

Example 92

The biological indicator analyzer of Example 91, wherein indicator scanner is selected from the group consisting of an optical reader and a wireless radio reader.

Example 93

The biological indicator analyzer of any one or more of Examples 90 through 92, further comprising a processor and a communication port, wherein the processor is configured to provide an analysis result set to a server via the communication port, wherein the analysis result comprises a set of results data and the unique identifier.

Example 94

The biological indicator analyzer of any one or more of Examples 90 through 93, further comprising a housing defining the wells and containing the organism detector features, wherein the housing provides base configured to support the housing on a surface, wherein the touch screen is oriented obliquely relative to the base.

X. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system for processing medical devices, the system comprising:
   (a) a sterilizing cabinet having a sterilizing compartment, a processor, a display, and an identification tag reader, wherein the sterilizing cabinet is operable to perform a sterilization cycle on a medical device and a biological indicator contained within the sterilizing compartment, wherein the processor is configured to:
      (i) display a prompt via the display for a user to scan the biological indicator with the identification tag reader,
      (ii) receive a set of biological indicator data from the identification tag reader,
      (iii) display a set of compatible sterilization cycles via the display based upon the set of biological indicator data, and
      (iv) receive a sterilization cycle selection from a user, wherein the sterilization cycle selection is selected from the set of compatible sterilization cycles;
   (b) a biological indicator analyzer, wherein the indicator analyzer is operable to perform an indicator analysis on the biological indicator to thereby determine efficacy of a sterilization cycle performed by the sterilizing cabinet; and
   (c) an external medium, wherein the external medium is operable to convey information between the sterilizing cabinet and the biological indicator analyzer, wherein the biological indicator analyzer is further configured to receive information from the external medium from the sterilizing cabinet.

2. The system of claim 1, wherein the external medium comprises a USB memory.

3. The system of claim 1, wherein the external medium is comprised by a communication hub, and wherein the communication hub further comprises a network interface.

4. The system of claim 3, wherein the communication hub is configured to communicate with at least one of the biological indicator analyzer and the sterilizing cabinet using a USB memory.

5. The system of claim 1, wherein the biological indicator analyzer comprises an optical reader configured to read a visual indicator from the sterilizing cabinet.

6. The system of claim 5, wherein the visual indicator includes an identification of the biological indicator, and is selected from a group consisting of a barcode and a QR code.

7. The system of claim 1, further comprising a server, wherein the server is configured to store a medical device database, wherein the medical device database comprises information describing the history and use of a plurality of medical devices, wherein the sterilizing cabinet and the server are configured to exchange data with each other directly without requiring use of the external medium.

8. A system for processing medical devices, the system comprising:
   (a) a sterilizing cabinet having a sterilizing compartment, a processor, a display, and an identification tag reader, wherein the sterilizing cabinet is operable to perform a sterilization cycle on a medical device and a biological indicator contained within the sterilizing compartment, wherein the processor is configured to:
      (i) display a prompt via the display for a user to scan the biological indicator with the identification tag reader,
      (ii) receive a set of biological indicator data from the identification tag reader,
      (iii) display a set of compatible sterilization cycles via the display based upon the set of biological indicator data, and
      (iv) receive a sterilization cycle selection from a user, wherein the sterilization cycle selection is selected from the set of compatible sterilization cycles;
   (b) a biological indicator analyzer, wherein the indicator analyzer is operable to perform an indicator analysis on the biological indicator to thereby determine efficacy of a sterilization cycle performed by the sterilizing cabinet;
   (c) a server configured to store a medical device database, wherein the medical device database comprises information describing the history and use of a plurality of medical devices; and
   (d) a communication hub comprising a network interface, wherein the communication hub is configured to process information from the sterilizing cabinet, the indicator analyzer, and the server.

9. The system of claim 8, wherein the communication hub is configured to process analysis data generated by the indicator analyzer to determine presence of contamination in the biological indicator after completion of the sterilization cycle.

10. The system of claim 9, wherein:
   (a) the biological indicator analyzer is configured to generate the analysis data by performing steps comprising:
      (i) emitting a light from a light source toward the biological indicator disposed in a well of the biological indicator analyzer; and
      (ii) using a sensor to detect fluorescence from the biological indicator disposed in the well;

(b) the communication hub is configured to process the analysis data by performing steps comprising:
  (i) identifying a drop in fluorescence from the biological indicator during a first time period;
  (ii) determining whether fluorescence from the biological indicator increases or remains substantially constant during a second period of time following the first period of time;
  (iii) in the event that fluorescence from the biological indicator is determined to increase during the second period of time, determining that contamination is present in the biological indicator; and
  (iv) in the event that fluorescence from the biological indicator is determined to remain substantially constant during the second period of time, determining that contamination is not present in the biological indicator.

11. The system of claim 10, wherein the communication hub is configured to determine whether fluorescence from the biological indicator increases or remains substantially constant during the second period of time based on comparing a slope of fluorescence detected over time from the biological indicator disposed in the well with a predefined critical value.

12. The system of claim 10 wherein the communication hub is configured to determine whether fluorescence form the biological indicator increases or remains substantially constant during the second period of time based on measurements from a first thirty minutes of incubation.

13. The system of claim 10 wherein the communication hub is configured to determine whether fluorescence form the biological indicator increases or remains substantially constant during the second period of time based on measurements from a first twenty minutes of incubation.

14. The system of claim 8, wherein the communication hub is configured to:
  (a) perform a correlation of analysis data generated from the biological indicator analyzer with sterilization cycles of the sterilizing cabinet;
  (b) based on the correlation, identify medical devices whose sterility may be questionable; and
  (c) send out one or more notifications preventing medical devices whose sterility may be questionable from being used before being put through an additional sterilization process.

15. The system of claim 8, wherein the communication hub is configured to manage a set of device configurations, wherein the set of device configurations comprises a sterilizing cabinet configuration and a biological indicator analyzer configuration, and wherein the communication hub is configured to exchange information based upon the set of device configurations.

16. The system of claim 15, wherein the communication hub is configured to define the sterilizing cabinet configuration by performing steps comprising:
  (a) receiving an identification of the biological indicator;
  (b) identifying the sterilization cycle as compatible with the biological indicator; and
  (c) defining the sterilization cabinet configuration as performing the sterilization cycle based on the identification of the sterilization cycle as being compatible with the biological indicator.

17. The system of claim 8, wherein the communication hub is configured to communicate with at least one of the biological indicator analyzer and the sterilizing cabinet using a USB memory.

18. A system for processing medical devices, the system comprising:
  (a) a non-transitory computer readable medium storing instructions to determine a set of compatible sterilization cycles from a set of potential sterilization cycles based on a biological indicator identification;
  (b) a sterilizing cabinet having a sterilizing compartment, a processor, a display, and an identification tag reader, wherein the sterilizing cabinet is operable to sterilize a medical device and a biological indicator contained within the sterilizing compartment, wherein the processor is configured to:
    (i) display a prompt via the display for a user to scan the biological indicator with the identification tag reader,
    (ii) receive a set of biological indicator data from the identification tag reader,
    (iii) display the set of compatible sterilization cycles via the display based upon the set of biological indicator data, and
    (iv) receive a sterilization cycle selection from a user, wherein the sterilization cycle selection is selected from the set of compatible sterilization cycles;
  (c) a biological indicator analyzer comprising a well, a light source, and sensor, wherein the indicator analyzer is operable to perform an indicator analysis on the biological indicator, using the light source and the sensor, when the biological indicator is placed in the well; and
  (d) a communication hub, wherein the communication hub is configured to exchange information between the sterilizing cabinet, and the indicator analyzer.

19. The system of claim 18, wherein the non-transitory computer readable medium is incorporated as a component within a device selected from a group consisting of:
  (a) the sterilizing cabinet; and
  (b) the communication hub.

20. The system of claim 18, wherein the biological indicator identification is a type for the biological indicator.

21. The system of claim 18, wherein the non-transitory computer readable medium stores instructions to determine that the set of compatible sterilization cycles has a cardinality of zero when (i) the biological indicator identification cannot be determined for the biological indicator; and/or (ii) compatibility of the biological indicator with the sterilizing cabinet and/or other devices in the system has not been validated.

22. The system of claim 21, wherein the system comprises a processor configured to, when the cardinality of the set of compatible sterilization cycles is zero, display a warning message to the user.

* * * * *